United States Patent
Miller-Jones et al.

(10) Patent No.: US 11,391,744 B2
(45) Date of Patent: *Jul. 19, 2022

(54) METHODS AND KITS

(71) Applicant: ARQUER DIAGNOSTICS LIMITED, Sunderland (GB)

(72) Inventors: David Nicholas Miller-Jones, Sunderland (GB); Cheryl Nyberg, Sunderland (GB); Ronald Alfred Laskey, Cambridge (GB); Kai Stoeber, Cambridge (GB)

(73) Assignee: ARQUER DIAGNOSTIC LIMITED, Sunderland (GB)

(*) Notice: Subject to any disclaimer, the term of this patent is extended or adjusted under 35 U.S.C. 154(b) by 667 days.

This patent is subject to a terminal disclaimer.

(21) Appl. No.: 15/580,663

(22) PCT Filed: Jun. 1, 2016

(86) PCT No.: PCT/GB2016/051611
§ 371 (c)(1),
(2) Date: Dec. 7, 2017

(87) PCT Pub. No.: WO2016/198835
PCT Pub. Date: Dec. 15, 2016

(65) Prior Publication Data
US 2019/0079102 A1  Mar. 14, 2019

(30) Foreign Application Priority Data

Jun. 8, 2015 (GB) .................... 1509908
Mar. 1, 2016 (GB) .................... 1603567

(51) Int. Cl.
*G01N 31/00* (2006.01)
*G01N 33/53* (2006.01)
*G01N 33/68* (2006.01)
*G01N 33/574* (2006.01)
*G01N 33/577* (2006.01)

(52) U.S. Cl.
CPC ....... *G01N 33/6893* (2013.01); *G01N 33/577* (2013.01); *G01N 33/57434* (2013.01)

(58) Field of Classification Search
None
See application file for complete search history.

(56) References Cited

U.S. PATENT DOCUMENTS

| | | |
|---|---|---|
| 4,022,576 A | 5/1977 | Parker |
| 4,868,108 A | 9/1989 | Bahar et al. |
| 5,016,644 A | 5/1991 | Guirguis |
| 5,087,556 A | 2/1992 | Ertinghausen |
| 6,008,003 A | 12/1999 | Haak-Frendscho et al. |
| 6,812,339 B1 | 11/2004 | Venter et al. |
| 7,498,145 B2 | 3/2009 | Uchiyama et al. |
| 7,842,467 B1 | 11/2010 | Heidbrink et al. |
| 7,932,047 B2 | 4/2011 | Ridder et al. |
| 8,062,892 B2 | 11/2011 | Schlegel et al. |
| 8,158,360 B2 | 4/2012 | Heise et al. |
| 8,193,332 B2 | 6/2012 | Takagi et al. |
| 8,344,211 B2 | 1/2013 | Alexandrov et al. |
| 8,470,798 B2 | 6/2013 | Takagi et al. |
| 8,497,101 B2 | 7/2013 | Mechali et al. |
| 8,652,416 B2 | 2/2014 | Kim et al. |
| 2004/0241876 A1 | 12/2004 | Fannes |
| 2005/0069900 A1 | 3/2005 | Lentrichia |
| 2005/0208558 A1 | 9/2005 | Venter et al. |
| 2006/0088840 A1 | 4/2006 | Giesing et al. |
| 2007/0037165 A1 | 2/2007 | Venter et al. |
| 2007/0184460 A1 | 8/2007 | Ching et al. |
| 2007/0184505 A1 | 8/2007 | Schmitt et al. |
| 2007/0237770 A1 | 10/2007 | Lai et al. |
| 2009/0088336 A1 | 4/2009 | Burd et al. |
| 2009/0226957 A1 | 9/2009 | Paterlini-Brechot |
| 2010/0015625 A1 | 1/2010 | Indra et al. |
| 2010/0094560 A1 | 4/2010 | Lois et al. |
| 2010/0240546 A1 | 9/2010 | Lo et al. |
| 2010/0240665 A1 | 9/2010 | Eckhardt et al. |
| 2011/0093962 A1 | 4/2011 | Heidbrink et al. |
| 2012/0039811 A1* | 2/2012 | Admon .............. A61K 39/0011 424/9.1 |

(Continued)

FOREIGN PATENT DOCUMENTS

| | | |
|---|---|---|
| AU | 2011236061 A1 | 11/2011 |
| CA | 2040088 A1 | 10/1992 |

(Continued)

OTHER PUBLICATIONS

Stoeber et al. Journal of The National Cancer Institute, vol. 94, No. 14, Jul. 17, 2002, pp. 1071-1079. (Year: 2002).*
Dudderidge et al. British Journal of Cancer, vol. 103, No. 5, Aug. 24, 2010, pp. 701-707. (Year: 2010).*
SEE651Hu 96 Tests Enzyme-linked Immunosorbent Assay Kit for Minichromosome Maintenance Deficient 5 (MCM5); Organism Species: *Homo sapiens* (Human); Instruction manual; Jul. 2013. (Year: 2013).*
Stoeber.et al., (Diagnosis of Genito-Urinary Tract Cancer by Detection of Minichromosome Maintenance 5 Protein in Urine Sediments, J Natl Cancer Inst. Jul. 17, 2002;94(14):1071-9). (Year: 2002).*

(Continued)

*Primary Examiner* — Lisa V Cook
(74) *Attorney, Agent, or Firm* — Kilpatrick Townsend & Stockton LLP

(57) ABSTRACT

The present invention relates to methods for detecting the presence of Mcm5 in a subject, the method comprising preparing a sample from said subject by exposing the sample to a lysis buffer and performing an assay to determine the concentration of Mcm5 by exposing the sample to a first monoclonal antibody and/or a second monoclonal antibody and measuring the amount of Mcm5 that binds to the first monoclonal antibody and/or the second monoclonal antibody. The invention further relates to kits that can be used in the methods.

21 Claims, 18 Drawing Sheets

Specification includes a Sequence Listing.

(56) References Cited

U.S. PATENT DOCUMENTS

| | | |
|---|---|---|
| 2012/0070837 A1 | 3/2012 | Huang et al. |
| 2012/0190046 A1 | 7/2012 | Datta et al. |
| 2013/0034869 A1 | 2/2013 | Whitesides et al. |
| 2013/0115599 A1 | 5/2013 | Huang et al. |
| 2013/0237453 A1 | 9/2013 | Chander |

FOREIGN PATENT DOCUMENTS

| | | |
|---|---|---|
| CN | 101358976 A | 2/2009 |
| CN | 101738469 A | 6/2010 |
| CN | 101993926 A | 3/2011 |
| CN | 102375061 A | 3/2012 |
| CN | 102707063 A | 10/2012 |
| CN | 103558384 A | 2/2014 |
| DE | 10316701 A1 | 11/2004 |
| DE | 10054632 A1 | 7/2007 |
| EP | 0217583 B1 | 4/1987 |
| EP | 0225054 B1 | 6/1987 |
| EP | 0509158 A1 | 10/1992 |
| EP | 0763738 A1 | 3/1997 |
| EP | 1388734 A1 | 2/2004 |
| EP | 1510820 A1 | 3/2005 |
| EP | 1628135 A1 | 2/2006 |
| EP | 1816460 A1 | 8/2007 |
| EP | 1916301 A1 | 4/2008 |
| EP | 1980856 A1 | 10/2008 |
| EP | 2138848 A1 | 12/2009 |
| EP | 2196803 A1 | 6/2010 |
| EP | 2434023 A1 | 3/2012 |
| EP | 2574400 A1 | 4/2013 |
| JP | 200580524 A | 3/2005 |
| JP | 2005315772 A2 | 11/2005 |
| JP | 20095655 A | 1/2009 |
| JP | 201088376 A | 4/2010 |
| JP | 2012196211 A | 10/2012 |
| KR | 1020150105167 A | 9/2015 |
| RU | 2456607 C1 | 7/2012 |
| RU | 2470301 C2 | 9/2012 |
| RU | 2463354 C1 | 10/2012 |
| WO | WO 9921014 A1 | 4/1999 |
| WO | WO 0026242 A2 | 5/2000 |
| WO | WO 0029852 A1 | 5/2000 |
| WO | WO 0039586 A2 | 7/2000 |
| WO | WO 0059943 A2 | 10/2000 |
| WO | WO 0102599 A2 | 1/2001 |
| WO | WO 0111361 A2 | 2/2001 |
| WO | WO 0171042 A2 | 9/2001 |
| WO | WO 02087641 A1 | 11/2002 |
| WO | WO 03024993 A2 | 3/2003 |
| WO | WO 03072035 A2 | 9/2003 |
| WO | WO 04023973 A2 | 3/2004 |
| WO | WO 04030615 A2 | 4/2004 |
| WO | WO 04035783 A2 | 4/2004 |
| WO | WO 04038418 A1 | 5/2004 |
| WO | WO 04039956 A2 | 5/2004 |
| WO | WO 04043361 A2 | 5/2004 |
| WO | WO 04092734 A2 | 10/2004 |
| WO | WO 05026211 A2 | 3/2005 |
| WO | WO 05084283 A2 | 9/2005 |
| WO | WO 05085860 A2 | 9/2005 |
| WO | WO 05095964 A2 | 10/2005 |
| WO | WO 05097189 A1 | 10/2005 |
| WO | WO 06039582 A2 | 4/2006 |
| WO | WO 06052822 A2 | 5/2006 |
| WO | WO 06071970 A2 | 7/2006 |
| WO | WO 06086573 A2 | 8/2006 |
| WO | WO 06116442 A2 | 11/2006 |
| WO | WO 06126821 A1 | 11/2006 |
| WO | WO 07031789 A1 | 3/2007 |
| WO | WO 07042256 A1 | 4/2007 |
| WO | WO 07045896 A1 | 4/2007 |
| WO | WO 07110314 A2 | 10/2007 |
| WO | WO 08021290 A2 | 2/2008 |
| WO | WO 08043566 A2 | 4/2008 |
| WO | WO 08085007 A1 | 7/2008 |
| WO | WO 08132453 A1 | 11/2008 |
| WO | WO 09002849 A2 | 12/2008 |
| WO | WO 09020596 A2 | 2/2009 |
| WO | WO 09050461 A1 | 4/2009 |
| WO | WO 09138392 A1 | 11/2009 |
| WO | WO 09145815 A2 | 12/2009 |
| WO | WO 09156711 A1 | 12/2009 |
| WO | WO 10025928 A1 | 3/2010 |
| WO | WO 10042228 A2 | 4/2010 |
| WO | WO 10107654 A2 | 9/2010 |
| WO | WO 11073619 A1 | 6/2011 |
| WO | WO 11082345 A2 | 7/2011 |
| WO | WO 11109705 A2 | 9/2011 |
| WO | WO 11126482 A1 | 10/2011 |
| WO | WO 11129762 A1 | 10/2011 |
| WO | WO 11133981 A1 | 10/2011 |
| WO | WO 12065117 A2 | 5/2012 |
| WO | WO 12090479 A1 | 7/2012 |
| WO | WO 12093251 A1 | 7/2012 |
| WO | WO 12109466 A2 | 8/2012 |
| WO | WO 12151465 A1 | 11/2012 |
| WO | WO 13071247 A1 | 5/2013 |
| WO | WO 13102757 A1 | 7/2013 |
| WO | WO 13120394 A1 | 8/2013 |
| WO | WO 13121368 A2 | 8/2013 |
| WO | WO 13151672 A2 | 10/2013 |
| WO | WO 13181418 A2 | 12/2013 |
| WO | WO 13190075 A2 | 12/2013 |
| WO | WO 14012176 A1 | 1/2014 |
| WO | WO 14025961 A1 | 2/2014 |
| WO | WO 14032899 A1 | 3/2014 |
| WO | WO 14065889 A2 | 5/2014 |
| WO | WO 14071029 A1 | 5/2014 |
| WO | WO 14077725 A1 | 5/2014 |
| WO | WO 14081278 A1 | 5/2014 |
| WO | WO 16112501 A1 | 7/2015 |

OTHER PUBLICATIONS

Abcam (1999;retrieved from url://www.abcam.com/protocols/sample-preparation-for-western-blot) (Year: 1999).*

Gutierez et al.(2012, retrieved from url.emdmillipore.com). (Year: 2012).*

Kelly et al., Bladder Cancer Diagnosis and Identification of Clinically Significant Disease by Combined Urinary Detection of Mcm5 and Nuclear Matrix Protein 22, PLOS ONE, 2012, 7(7), e40305, pp. 1-9.

PerkinElmer product brochure, "Applications of time-resolved fluorometry with the DELFIA® method," Feb. 2006, 24 pages.

Wollenschlaeger Dissertation, The DNA Replication Initiation Machinery as a Target for Cancer Diagnosis and Therapy, 2011, pp. 1-148.

International Search Report issued in connection with corresponding International Application No. PCT/GB2016/051611, dated Sep. 23, 2016, 2 pages.

Altschul et al., "Basic local alignment search tool", Oct. 1990; 215(3): 403-410.

Ayaru L et al., "Diagnosis of pancreaticobiliary malignancy by detection of minichromosome maintenance protein 5 in bile aspirates," British Journal of Cancer (2008) 98, 1548-1554.

Bauminger S et al., "The use of carbodiimides in the preparation of immunizing conjugates", Methods Enzymol. 1980; 70(A): 151-9.

Burger M, "MCM2 and MCM5 as prognostic markers in colon cancer: a worthwhile approach", Dig Dis Sci. Feb. 2009; 54(2): 197-8.

Chun FK et al., "Prostate cancer gene 3 (PCA3): development and internal validation of a novel biopsy nomogram", Eur Urol. Oct. 2009; 56(4): 659-67.

Devereux et al., "A comprehensive set of sequence analysis programs for the VAX", Nucleic Acids Research Jan. 1984; 12(1): 387-395.

Dudderidge TJ et al., "Diagnosis of prostate cancer by detection of minichromosome maintenance 5 protein urine sediments", Br J Cancer. Aug. 2010; 103(5): 701-7.

(56) References Cited

OTHER PUBLICATIONS

Going JJ et al., "Aberrant expression of minichromosome maintenance proteins 2 and 5, and Ki-67 in dysplastic squamous oesophageal epithelium and Barrett's mucosa," Gut 2002;50:373-377.

Gonzalez MA et al., "New Minimally Invasive Approaches to Early Cancer Detection", European Oncological Disease. 2007; 1(2): 122-4.

Herr HW, "The natural history of a T1 bladder cancer: life-long tumour diathesis", BJU Int. 1999; 84: 1102-1103.

Hessels D & Schalken JA, "The use of PCA3 in the diagnosis of prostate cancer", Nat Rev Urol. May 2009; 6(5): 255-61.

Jemal A et al., "Cancer statistics, 2007", CA Cancer J Clin. Jan.-Feb. 2007; 57(1): 43-66.

Karakiewizc et al., "Critical evaluation of urinary markers for bladder cancer detection and monitoring", Rev Urol, 2008 Spring; 10(2): 120-135.

Kelly JD et al., "Bladder cancer diagnosis and identification of clinically significant disease by combined urinary detection of Mcm6 and nuclear matrix protein 22", PLoS ONE. 2012; 7(7): e40305.

Kilpelainen TP et al., "False-positive screening results in the Finnish prostate cancer screening trial", Br J Cancer. Feb. 2010; 102(3): 469-74.

Scarpini Cinzia et al., "Improved Screening for Anal Neoplasia by Immunocytochemical Detection of Minichromosome Maintenance Proteins," Cancer Epidemiol Biomarkers Prev2008;17(10). Oct. 2008.

Stoeber K et al., "Diagnosis of Genito-Urinary Tract Cancer by Detection of Minichromosome Maintenance 5 Protein in Urine Sediments", J of the Nat Cancer Inst. Jul. 2002; 94(14): 1071-79.

Stoeber K et al., "Immunoassay for urothelial cancers that detects DNA replication protein Mcm5 in urine", The Lancet, vol. 354, Oct. 30, 1999, 1524-1525.

Swinn RA. "Immunoassay for minichromosome maintenance protein Mcm5 in cancer detection", MPhil Thesis submitted to Anglia Polytechnic University in Nov. 2004.

Thompson IM et al., "Operating characteristics of prostate-specific antigen in men with an initial PSA level of 3.0 ng.ml or lower", JAMA. Jul. 2005; 294(1): 66-71.

Thomson JD et al. "Clustal W: improving the sensitivity of progressive multiple sequence alignment through sequence weighting, position-specific gap penalties and weight matrix choice", Nucleic Acids Res. 1994; 22:4673-4680.

Van Der Poel HG & Debruyne FB, "Can biological markers replace cystoscopy? An update", Curr Opin Urol. Oct. 2001; 11(5): 503-9.

Watkins JL, "An investigation into minichromosomal maintenance proteins (MCMs) for the diagnosis of prostate cancer, as a possible alternative to prostate specific antigen (PSA)", Feb. 2005. Retrieved from the Internet <URL:https://dspace.lib.cranfield.ac.uk/bitstream/1826/1643/1/JaneWatkinsPhDThesis.pdf> [retrieved on Jan. 27, 2015] 200 pages.

Wiener HG et al., "Accuracy of urinary cytology in the diagnosis of primary and recurrent bladder cancer", Acta Cytol. Mar.-Apr. 1993; 37(2): 163-9.

Williams GH et al., "Diagnosis of oesophageal cancer by detection of minichromosome maintenance 5 protein in gastric aspirates", BJC. Aug. 2004; 91(4): 714-9.

Abcam, "Sample preparation for western blot" (1999); retrieved from url://www.abcam.com/protocols/sample-preparation-for-western-blot; 8 pages.

Gutierrez et al., "Evaluation of common protein extraction reagents in mammalian and bacteria lysates, by infrared (IR) based quantification and Western blotting" (2012); Lit No. PS4993EN00; retrieved from url.emdmillipore.com; 1 page.

Manuscript Preparation, Journal of the National Cancer Institute, UK, retrieved from https://academic.oup.com/jnci/pages/Manuscript_Preparation on Mar. 3, 2020, 21 pages.

Guide to Authors, British Journal of Cancer, UK, retrieved from https://www.nature.com/bjc/authors-and-referees/gta on Mar. 3, 2020, 11 pages.

Information for Authors, Journal of the National Cancer Institute, vol. 93, No. 19, pp. 1506-1509, Oct. 3, 2001.

Elabscience, "ELISA Horseradish Peroxidase—HRP" (Jun. 11, 2014); retrieved from https://www.eiabscience.com/List-detail-240.html, 4 pages.

Schultz, Randall W. et al., "Dynamic Localization of the DNA Replication Proteins MCM5 and MCM7 in Plants," Plant Physiology, Jun. 2009, vol. 150, pp. 658-669.

Stoeber, Kai. Extracted pages of PhD thesis. University of Cambridge, Mar. 2001, 41 pages.

\* cited by examiner

SEQUENCE LISTING

<160> NUMBER OF SEQ ID NOS: 36

<210> SEQ ID NO 1
<211> LENGTH: 7
<212> TYPE: PRT
<213> ORGANISM: Artificial sequence
<220> FEATURE:
<223> OTHER INFORMATION: Epitope to which antibody 12A7 binds

<400> SEQUENCE: 1

Trp Asp Glu Thr Lys Gly Glu
1               5

<210> SEQ ID NO 2
<211> LENGTH: 7
<212> TYPE: PRT
<213> ORGANISM: Artificial sequence
<220> FEATURE:
<223> OTHER INFORMATION: Epitope to which antibody 4B4 binds

<400> SEQUENCE: 2

Asp Asp Arg Val Ala Ile His
1               5

<210> SEQ ID NO 3
<211> LENGTH: 11
<212> TYPE: PRT
<213> ORGANISM: Artificial sequence
<220> FEATURE:
<223> OTHER INFORMATION: 12A7 light chain CDR 1 polypeptide sequence

<400> SEQUENCE: 3

Gln Asn Leu Val Gln Ser Asn Gly Asn Thr Tyr
1               5                   10

<210> SEQ ID NO 4
<211> LENGTH: 36
<212> TYPE: DNA
<213> ORGANISM: Artificial sequence
<220> FEATURE:
<223> OTHER INFORMATION: 12A7 light chain CDR 1 nucleotide sequence

<400> SEQUENCE: 4
cagaaccttg tacaaagtaa tggaaacacc tattta                              36

<210> SEQ ID NO 5
<211> LENGTH: 4
<212> TYPE: PRT
<213> ORGANISM: Artificial sequence
<220> FEATURE:
<223> OTHER INFORMATION: 12A7 light chain CDR 2 polypeptide sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 5

Lys Val Ser Xaa
1

<210> SEQ ID NO 6
<211> LENGTH: 10
<212> TYPE: DNA
<213> ORGANISM: Artificial sequence
<220> FEATURE:
<223> OTHER INFORMATION: 12A7 light chain CDR 2 nucleotide sequence

<400> SEQUENCE: 6
aagtttccaa                                                          10

<210> SEQ ID NO 7
<211> LENGTH: 9
<212> TYPE: PRT
<213> ORGANISM: Artificial sequence
<220> FEATURE:
<223> OTHER INFORMATION: 12A7 light chain CDR 3 polypeptide sequence

<400> SEQUENCE: 7

Ser Gln Ser Thr Arg Val Pro Tyr Thr
1               5

<210> SEQ ID NO 8
<211> LENGTH: 27
<212> TYPE: DNA
<213> ORGANISM: Artificial sequence
<220> FEATURE:
<223> OTHER INFORMATION: 12A7 light chain CDR 3 nucleotide sequence

<400> SEQUENCE: 8
tctcaaagta cacgtgttcc gtacaca                                            27

<210> SEQ ID NO 9
<211> LENGTH: 10
<212> TYPE: PRT
<213> ORGANISM: Artificial sequence
<220> FEATURE:
<223> OTHER INFORMATION: 12A7 heavy chain CDR 1 polypeptide sequence

<400> SEQUENCE: 9

Gly Phe Ser Leu Ser Thr Ser Gly Met Gly
1               5                   10

<210> SEQ ID NO 10
<211> LENGTH: 30
<212> TYPE: DNA
<213> ORGANISM: Artificial sequence
<220> FEATURE:
<223> OTHER INFORMATION: 12A7 heavy chain CDR 1 nucleotide sequence

<400> SEQUENCE: 10
gggttttcac tgagcacttc tggtatgggt                                         30

<210> SEQ ID NO 11
<211> LENGTH: 7
<212> TYPE: PRT
<213> ORGANISM: Artificial sequence
<220> FEATURE:
<223> OTHER INFORMATION: 12A7 heavy chain CDR 2 polypeptide sequence

<400> SEQUENCE: 11

Ile Phe Trp Asp Asp Asp Lys
1               5

<210> SEQ ID NO 12
<211> LENGTH: 21
<212> TYPE: DNA
<213> ORGANISM: Artificial sequence
<220> FEATURE:
<223> OTHER INFORMATION: 12A7 heavy chain CDR 2 nucleotide sequence

<400> SEQUENCE: 12
attttctggg atgatgacaa g                                                  21

<210> SEQ ID NO 13
<211> LENGTH: 13
<212> TYPE: PRT
<213> ORGANISM: Artificial sequence
<220> FEATURE:
<223> OTHER INFORMATION: 12A7 heavy chain CDR 3 polypeptide sequence

<400> SEQUENCE: 13

Ala Arg Arg Ser Asp Tyr Asn Tyr Tyr Ser Met Asp Tyr
1               5                   10

<210> SEQ ID NO 14
<211> LENGTH: 39
<212> TYPE: DNA
<213> ORGANISM: Artificial sequence
<220> FEATURE:
<223> OTHER INFORMATION: 12A7 heavy chain CDR 3 nucleotide sequence

<400> SEQUENCE: 14
gcgcggcgaa gtgactacaa ttactactct atggactac                               39

```
<210> SEQ ID NO 15
<211> LENGTH: 6
<212> TYPE: PRT
<213> ORGANISM: Artificial sequence
<220> FEATURE:
<223> OTHER INFORMATION: 4B4 light chain CDR 1 polypeptide sequence

<400> SEQUENCE: 15

Gln Asp Ile Gly Ser Ser
1               5

<210> SEQ ID NO 16
<211> LENGTH: 18
<212> TYPE: DNA
<213> ORGANISM: Artificial sequence
<220> FEATURE:
<223> OTHER INFORMATION: 4B4 light chain CDR 1 nucleotide sequence

<400> SEQUENCE: 16
caggacattg gtagtagc                                                 18

<210> SEQ ID NO 17
<211> LENGTH: 4
<212> TYPE: PRT
<213> ORGANISM: Artificial sequence
<220> FEATURE:
<223> OTHER INFORMATION: 4B4 light chain CDR 2 polypeptide sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 17

Ala Thr Ser Xaa
1

<210> SEQ ID NO 18
<211> LENGTH: 10
<212> TYPE: DNA
<213> ORGANISM: Artificial sequence
<220> FEATURE:
<223> OTHER INFORMATION: 4B4 light chain CDR 2 nucleotide sequence
<220> FEATURE:
<221> NAME/KEY: misc_feature
<222> LOCATION: (10)..(10)
<223> OTHER INFORMATION: n is a, c, g, or t

<400> SEQUENCE: 18 gccacatccn                                                          10

<210> SEQ ID NO 19
<211> LENGTH: 9
<212> TYPE: PRT
<213> ORGANISM: Artificial sequence
<220> FEATURE:
<223> OTHER INFORMATION: 4B4 light chain CDR 3 polypeptide sequence

<400> SEQUENCE: 19

Leu Gln Tyr Ala Ser Ser Pro Pro Thr
1               5

<210> SEQ ID NO 20
<211> LENGTH: 27
<212> TYPE: DNA
<213> ORGANISM: Artificial sequence
<220> FEATURE:
<223> OTHER INFORMATION: 4B4 light chain CDR 3 nucleotide sequence

<400> SEQUENCE: 20
```

```
ctacaatatg ctagttctcc tccgacg                                          27
```

<210> SEQ ID NO 21
<211> LENGTH: 8
<212> TYPE: PRT
<213> ORGANISM: Artificial sequence
<220> FEATURE:
<223> OTHER INFORMATION: 4B4 heavy chain CDR 1 polypeptide sequence

<400> SEQUENCE: 21

```
Gly Phe Thr Phe Ser Asn Tyr Ala
1               5
```

<210> SEQ ID NO 22
<211> LENGTH: 24
<212> TYPE: DNA
<213> ORGANISM: Artificial sequence
<220> FEATURE:
<223> OTHER INFORMATION: 4B4 heavy chain CDR 1 nucleotide sequence

<400> SEQUENCE: 22

```
ggattcactt tcagtaacta tgcc                                             24
```

<210> SEQ ID NO 23
<211> LENGTH: 8
<212> TYPE: PRT
<213> ORGANISM: Artificial sequence
<220> FEATURE:
<223> OTHER INFORMATION: 4B4 heavy chain CDR 2 polypeptide sequence

<400> SEQUENCE: 23

```
Ile Ser Arg Gly Gly Ser Tyr Thr
1               5
```

<210> SEQ ID NO 24
<211> LENGTH: 24
<212> TYPE: DNA
<213> ORGANISM: Artificial sequence
<220> FEATURE:
<223> OTHER INFORMATION: 4B4 heavy chain CDR 2 nucleotide sequence

<400> SEQUENCE: 24

```
attagtcgtg gtggtagtta cacc                                             24
```

<210> SEQ ID NO 25
<211> LENGTH: 15
<212> TYPE: PRT
<213> ORGANISM: Artificial sequence
<220> FEATURE:
<223> OTHER INFORMATION: 4B4 heavy chain CDR 3 polypeptide sequence

<400> SEQUENCE: 25

```
Ala Arg His Gly Tyr Asn Tyr Asp Asp Gly Ala Trp Phe Ala Asn
1               5                   10                  15
```

<210> SEQ ID NO 26
<211> LENGTH: 45
<212> TYPE: DNA
<213> ORGANISM: Artificial sequence
<220> FEATURE:
<223> OTHER INFORMATION: 4B4 heavy chain CDR 3 nucleotide sequence

<400> SEQUENCE: 26

```
gcaagacatg gatataatta cgacgacggg gcctggtttg ctaac                      45
```

<210> SEQ ID NO 27
<211> LENGTH: 113
<212> TYPE: PRT
<213> ORGANISM: Artificial sequence
<220> FEATURE:
<223> OTHER INFORMATION: 12A7 full variable light chain sequence
      (polypeptide)

<400> SEQUENCE: 27

Asp Ile Met Leu Thr Gln Ser Pro Leu Ser Leu Ser Val Thr Leu Gly
1               5                   10                  15

Asp Gln Ala Ser Ile Ser Cys Arg Ser Gln Asn Leu Val Gln Ser
            20                  25                  30

Asn Gly Asn Thr Tyr Leu Thr Trp Tyr Leu Gln Lys Pro Gly Gln Ser
        35                  40                  45

Pro Lys Val Leu Ile Asn Lys Val Ser Asn Arg Phe Tyr Gly Val Pro
    50                  55                  60

Asp Arg Phe Ser Gly Ser Gly Ser Gly Thr Asp Phe Thr Leu Arg Ile
65              70                  75                  80

Ser Arg Val Glu Ala Glu Asp Leu Gly Ile Tyr Phe Cys Ser Gln Ser
                85                  90                  95

Thr Arg Val Pro Tyr Thr Phe Gly Gly Gly Thr Lys Leu Glu Ile Arg
            100                 105                 110

Arg

<210> SEQ ID NO 28
<211> LENGTH: 338
<212> TYPE: DNA
<213> ORGANISM: Artificial sequence
<220> FEATURE:
<223> OTHER INFORMATION: 12A7 full variable light chain sequence
      (nucleotide)

<400> SEQUENCE: 28
gatatcatgc tgacccaatc tccactctcc ctgtctgtca ctcttggaga tcaggcctcc      60
atctcttgca gatctagtca gaaccttgta caaagtaatg gaaacaccta tttaacttgg    120
tacctgcaga agccaggcca gtctccaaag gtcctgatca acaaagtttc caaccgattt    180
tatggggtcc cagacaggtt cagtggcagt ggatcaggga cagatttcac actcaggatc    240
agcagagtgg aggctgagga tctgggaatt tatttctgct ctcaaagtac acgtgttccg    300
tacacattcg gaggggggac caagctggaa ataagacg                            338

<210> SEQ ID NO 29
<211> LENGTH: 121
<212> TYPE: PRT
<213> ORGANISM: Artificial sequence
<220> FEATURE:
<223> OTHER INFORMATION: 12A7 full variable heavy chain sequence
      (polypeptide)

<400> SEQUENCE: 29

Gln Gln Asp Leu Gln Gln Ser Gly Pro Gly Ile Leu Gln Pro Thr Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Ser Ser Asn Met Gly Leu Glu
        35                  40                  45

Trp Leu Ala His Ile Phe Trp Asp Asp Lys Arg Tyr Asn Pro Ser
    50                  55                  60

```
Leu Arg Ser Arg Leu Thr Leu Ser Lys Asp Thr Ser Ser Ser Gln Val
 65                  70                  75                  80

Phe Leu Met Ile Thr Ser Val Ser Thr Ala Asp Ser Ala Thr Tyr Tyr
                 85                  90                  95

Cys Ala Arg Arg Ser Asp Tyr Asn Tyr Tyr Ser Met Asp Tyr Trp Gly
            100                 105                 110

Gln Gly Thr Ala Val Thr Val Ser Ser
        115                 120
```

<210> SEQ ID NO 30
<211> LENGTH: 363
<212> TYPE: DNA
<213> ORGANISM: Artificial sequence
<220> FEATURE:
<223> OTHER INFORMATION: 12A7 full variable heavy chain sequence
      (nucleotide)

<400> SEQUENCE: 30

```
cagcaagatc tgcagcagtc tggccctggg atattgcagc ccacccagac cctcagtctg    60
acttgttctt tctctgggtt ttcactgagc acttctggta tgggtgtgag ttggattcgt   120
caatcttcaa atatgggtct ggagtggctg gcacacattt tctgggatga tgacaagcgc   180
tataatccct ccctgaggag ccgactcacg ctctccaagg ataccctcca tagccaggta   240
tttctcatga tcaccagtgt gagtactgca gattctgcca catactactg tgcgcggcga   300
agtgactaca attactactc tatggactac tggggtcaag gaaccgcagt caccgtctcc   360
tca                                                                 363
```

<210> SEQ ID NO 31
<211> LENGTH: 107
<212> TYPE: PRT
<213> ORGANISM: Artificial sequence
<220> FEATURE:
<223> OTHER INFORMATION: 4B4 full variable light chain sequence
      (polypeptide)

<400> SEQUENCE: 31

```
Asp Ile Met Leu Thr Gln Ser Pro Ser Ser Leu Ser Ala Ser Leu Gly
  1               5                  10                  15

Glu Arg Val Ser Leu Thr Cys Arg Ala Ser Gln Asp Ile Gly Ser Ser
                 20                  25                  30

Leu Asn Trp Leu Gln Gln Glu Pro Asp Gly Thr Ile Lys Arg Leu Ile
             35                  40                  45

Tyr Ala Thr Ser Ser Leu Asp Ser Gly Val Pro Lys Arg Phe Ser Gly
 50                  55                  60

Ser Arg Ser Gly Ser Asp Tyr Ser Leu Thr Ile Ser Ser Leu Glu Ser
 65                  70                  75                  80

Glu Asp Phe Val Asp Tyr Tyr Cys Leu Gln Tyr Ala Ser Ser Pro Pro
                 85                  90                  95

Thr Phe Gly Gly Gly Thr Lys Leu Glu Ile Lys
            100                 105
```

<210> SEQ ID NO 32
<211> LENGTH: 322
<212> TYPE: DNA
<213> ORGANISM: Artificial sequence
<220> FEATURE:
<223> OTHER INFORMATION: 4B4 full variable light chain sequence
      (nucleotide)

<400> SEQUENCE: 32

```
gatatcatgc tgacccaatc tccatcctcc ttatctgcct ctctgggaga aagagtcagt    60
ctcacttgtc gggcaagtca ggacattggt agtagcttaa actggcttca acaggaacca   120
gatggaacta ttaaacgcct aatctacgcc acatccagtt tagattctgg tgtccccaaa   180
aggttcagtg gcagtaggtc tgggtcagat tattctctca ccatcagcag ccttgagtct   240
gaagattttg tagactatta ctgtctacaa tatgctagtt ctcctccgac gttcggtgga   300
ggcaccaagc tggaaatcaa ac                                            322
```

<210> SEQ ID NO 33
<211> LENGTH: 121
<212> TYPE: PRT
<213> ORGANISM: Artificial sequence
<220> FEATURE:
<223> OTHER INFORMATION: 4B4 full variable heavy chain sequence
      (polypeptide)

<400> SEQUENCE: 33

```
Val Lys Leu Gln Glu Ser Gly Gly Leu Val Lys Pro Gly Gly Ser
1               5                   10                  15

Leu Lys Leu Ser Cys Ala Ala Ser Gly Phe Thr Phe Ser Asn Tyr Ala
            20                  25                  30

Met Ser Trp Val Arg Gln Asn Pro Glu Lys Arg Leu Glu Trp Val Ala
        35                  40                  45

Thr Ile Ser Arg Gly Gly Ser Tyr Thr Tyr Tyr Pro Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ser Glu Asp Thr Ala Met Tyr Phe Cys Ala
                85                  90                  95

Arg His Gly Tyr Asn Tyr Asp Asp Gly Ala Trp Phe Ala Asn Trp Gly
            100                 105                 110

Gln Gly Thr Leu Val Thr Val Ser Ala
        115                 120
```

<210> SEQ ID NO 34
<211> LENGTH: 366
<212> TYPE: DNA
<213> ORGANISM: Artificial sequence
<220> FEATURE:
<223> OTHER INFORMATION: 4B4 full variable heavy chain sequence
      (nucleotide)

<400> SEQUENCE: 34

```
taggtgaaac tgcaggagtc tgggggaggc ttagtgaagc ctggagggtc cctgaaactc    60
tcctgtgcag cctctggatt cactttcagt aactatgcca tgtcttgggt tcgccagaat   120
ccggagaaga ggctggagtg ggtcgcaacc attagtcgtg gtggtagtta cacctactat   180
ccagacagtg tgaagggtcg attcaccatc tccagagaca atgccaagaa caccctgtat   240
ctgcaaatga acagtctgag gtctgaggac acggccatgt atttctgtgc aagacatgga   300
tataattacg acgacggggc ctggtttgct aactggggcc aagggactct ggtcactgtc   360
tctgca                                                              366
```

<210> SEQ ID NO 35
<211> LENGTH: 734
<212> TYPE: PRT
<213> ORGANISM: Homo sapiens
<220> FEATURE:

<223> OTHER INFORMATION: Mcm5 (polypeptide)

<400> SEQUENCE: 35

```
Met Ser Gly Phe Asp Pro Gly Ile Phe Tyr Ser Asp Ser Phe Gly
 1               5                  10                  15

Gly Asp Ala Gln Ala Asp Glu Gly Gln Ala Arg Lys Ser Gln Leu Gln
             20                  25                  30

Arg Arg Phe Lys Glu Phe Leu Arg Gln Tyr Arg Val Gly Thr Asp Arg
             35                  40                  45

Thr Gly Phe Thr Phe Lys Tyr Arg Asp Glu Leu Lys Arg His Tyr Asn
         50                  55                  60

Leu Gly Glu Tyr Trp Ile Glu Val Glu Met Glu Asp Leu Ala Ser Phe
 65                  70                  75                  80

Asp Glu Asp Leu Ala Asp Tyr Leu Tyr Lys Gln Pro Ala Glu His Leu
                 85                  90                  95

Gln Leu Leu Glu Glu Ala Ala Lys Glu Val Ala Asp Glu Val Thr Arg
            100                 105                 110

Pro Arg Pro Ser Gly Glu Glu Val Leu Gln Asp Ile Gln Val Met Leu
            115                 120                 125

Lys Ser Asp Ala Ser Pro Ser Ser Ile Arg Ser Leu Lys Ser Asp Met
130                 135                 140

Met Ser His Leu Val Lys Ile Pro Gly Ile Ile Ile Ala Ala Ser Ala
145                 150                 155                 160

Val Arg Ala Lys Ala Thr Arg Ile Ser Ile Gln Cys Arg Ser Cys Arg
                165                 170                 175

Asn Thr Leu Thr Asn Ile Ala Met Arg Pro Gly Leu Glu Gly Tyr Ala
                180                 185                 190

Leu Pro Arg Lys Cys Asn Thr Asp Gln Ala Gly Arg Pro Lys Cys Pro
            195                 200                 205

Leu Asp Pro Tyr Phe Ile Met Pro Asp Lys Cys Lys Cys Val Asp Phe
            210                 215                 220

Gln Thr Leu Lys Leu Gln Glu Leu Pro Asp Ala Val Pro His Gly Glu
225                 230                 235                 240

Met Pro Arg His Met Gln Leu Tyr Cys Asp Arg Tyr Leu Cys Asp Lys
                245                 250                 255

Val Val Pro Gly Asn Arg Val Thr Ile Met Gly Ile Tyr Ser Ile Lys
                260                 265                 270

Lys Phe Gly Leu Thr Thr Ser Arg Gly Arg Asp Arg Val Gly Val Gly
            275                 280                 285

Ile Arg Ser Ser Tyr Ile Arg Val Leu Gly Ile Gln Val Asp Thr Asp
            290                 295                 300

Gly Ser Gly Arg Ser Phe Ala Gly Ala Val Ser Pro Gln Glu Glu Glu
305                 310                 315                 320

Glu Phe Arg Arg Leu Ala Ala Leu Pro Asn Val Tyr Glu Val Ile Ser
                325                 330                 335

Lys Ser Ile Ala Pro Ser Ile Phe Gly Gly Thr Asp Met Lys Lys Ala
            340                 345                 350

Ile Ala Cys Leu Leu Phe Gly Gly Ser Arg Lys Arg Leu Pro Asp Gly
            355                 360                 365

Leu Thr Arg Arg Gly Asp Ile Asn Leu Leu Met Leu Gly Asp Pro Gly
            370                 375                 380

Thr Ala Lys Ser Gln Leu Leu Lys Phe Val Glu Lys Cys Ser Pro Ile
385                 390                 395                 400
```

Gly Val Tyr Thr Ser Gly Lys Gly Ser Ser Ala Ala Gly Leu Thr Ala
            405                 410                 415

Ser Val Met Arg Asp Pro Ser Arg Asn Phe Ile Met Glu Gly Gly
        420                 425                 430

Ala Met Val Leu Ala Asp Gly Val Val Cys Ile Asp Glu Phe Asp
        435                 440                 445

Lys Met Arg Glu Asp Arg Val Ala Ile His Glu Ala Met Glu Gln
    450                 455                 460

Gln Thr Ile Ser Ile Ala Lys Ala Gly Ile Thr Thr Leu Asn Ser
465                 470                 475                 480

Arg Cys Ser Val Leu Ala Ala Asn Ser Val Phe Gly Arg Trp Asp
                485                 490                 495

Glu Thr Lys Gly Glu Asp Asn Ile Asp Phe Met Pro Thr Ile Leu Ser
            500                 505                 510

Arg Phe Asp Met Ile Phe Ile Val Lys Asp Glu His Asn Glu Glu Arg
        515                 520                 525

Asp Val Met Leu Ala Lys His Val Ile Thr Leu His Val Ser Ala Leu
    530                 535                 540

Thr Gln Thr Gln Ala Val Glu Gly Glu Ile Asp Leu Ala Lys Leu Lys
545                 550                 555                 560

Lys Phe Ile Ala Tyr Cys Arg Val Lys Cys Gly Pro Arg Leu Ser Ala
                565                 570                 575

Glu Ala Ala Glu Lys Leu Lys Asn Arg Tyr Ile Ile Met Arg Ser Gly
            580                 585                 590

Ala Arg Gln His Glu Arg Asp Ser Asp Arg Arg Ser Ser Ile Pro Ile
        595                 600                 605

Thr Val Arg Gln Leu Glu Ala Ile Val Arg Ile Ala Glu Ala Leu Ser
    610                 615                 620

Lys Met Lys Leu Gln Pro Phe Ala Thr Glu Ala Asp Val Glu Glu Ala
625                 630                 635                 640

Leu Arg Leu Phe Gln Val Ser Thr Leu Asp Ala Ala Leu Ser Gly Thr
                645                 650                 655

Leu Ser Gly Val Glu Gly Phe Thr Ser Gln Glu Asp Gln Glu Met Leu
            660                 665                 670

Ser Arg Ile Glu Lys Gln Leu Lys Arg Arg Phe Ala Ile Gly Ser Gln
        675                 680                 685

Val Ser Glu His Ser Ile Ile Lys Asp Phe Thr Lys Gln Lys Tyr Pro
    690                 695                 700

Glu His Ala Ile His Lys Val Leu Gln Leu Met Leu Arg Arg Gly Glu
705                 710                 715                 720

Ile Gln His Arg Met Gln Arg Lys Val Leu Tyr Arg Leu Lys
                725                 730

<210> SEQ ID NO 36
<211> LENGTH: 2534
<212> TYPE: DNA
<213> ORGANISM: Homo sapiens
<220> FEATURE:
<223> OTHER INFORMATION: Mcm5 (mRNA)

<400> SEQUENCE: 36
ggaaaaccag aggcgcagtc atgtcgggat cgacgatcc tggcatttc tacagcgaca      60 gcttcggggg cgacgcccag gccgacgagg ggcaggcccg caaatcgcag ctgcagaggc     120
gcttcaagga gttcctgcgg cggtaccgag tgggcaccga ccgcacgggc ttcacctca     180

| | |
|---|---|
| aatacaggga tgaactcaag cggcattaca acctggggga gtactggatt gaggtggaga | 240 |
| tggaggatct ggccagcttt gatgaggacc tggccgacta cttgtacaag cagccagccg | 300 |
| agcacctgca gctgctggag aagctgccaa aggaggtagc tgatgaggtg acccggcccc | 360 |
| ggccttctgg ggaggaggtg ctccaggaca tccaggtcat gctcaagtcg acgccagcc | 420 |
| cttccagcat tcgtagcctg aagtcggaca tgatgtcaca cctggtgaag atccctggca | 480 |
| tcatcatcgc ggcctctgcg gtccgtgcca aggccacccg catctctatc cagtgccgca | 540 |
| gctgccgcaa caccctcacc aacattgcca tgcgccctgg cctcgagggc tatgccctgc | 600 |
| ccaggaagtg caacacagat caggctgggc gccccaaatg cccattggac ccgtacttca | 660 |
| tcatgcccga caaatgcaaa tgcgtggact ccagaccct gaagctgcag gagctgcctg | 720 |
| atgcagtccc ccacggggag atgcccagac acatgcagct ctactgcgac aggtacctgt | 780 |
| gtgacaaggt cgtccctggg aacagggtta ccatcatggg catctactcc atcaagaagt | 840 |
| ttggcctgac taccagcagg ggccgtgaca gggtgggcgt gggcatccga agctcctaca | 900 |
| tccgtgtcct gggcatccag gtggacacag atggctctgg ccgcagcttt gctggggccg | 960 |
| tgagcccca ggaggaggag gagttccgtc gcctggctgc cctcccaaat gtctatgagg | 1020 |
| tcatctccaa gagcatcgcc ccctccatct tgggggcac agacatgaag aaggccattg | 1080 |
| cctgcctgct ctttggggc tcccgaaaga ggctccctga tggacttact cgccgaggag | 1140 |
| acatcaacct gctgatgcta ggggaccctg ggacagccaa gtcccagctt ctgaagtttg | 1200 |
| tggagaagtg ttctcccatt ggggtataca cgtctgggaa aggcagcagc gcagctggac | 1260 |
| tgacagcctc ggtgatgagg gacccttcgt cccggaattt catcatggag ggcggagcca | 1320 |
| tggtcctggc cgatggtggg gtcgtctgta ttgacgagtt tgacaagatg cgagaagatg | 1380 |
| accgtgtggc aatccacgaa gccatggagc agcagaccat ctctatcgcc aaggctggga | 1440 |
| tcaccaccac cctgaactcc cgctgctccg tcctggctgc tgccaactca gtgttcggcc | 1500 |
| gctgggatga cacgaagggg gaggacaaca ttgacttcat gcccaccatc ttgtcgcgct | 1560 |
| tcgacatgat cttcatcgtc aaggatgagc acaatgagga gagggatgtg atgctggcca | 1620 |
| agcatgtcat cactctgcac gtgagcgcac tgacacagac acaggctgtg gagggcgaga | 1680 |
| ttgacctggc caagctgaag aagtttattg cctactgccg agtgaagtgt ggccccggc | 1740 |
| tgtcagcaga ggctgcagag aaactgaaga accgctacat catcatgcgg agcggggccc | 1800 |
| gtcagcacga gagggacagt gaccgccgct ccagcatccc catcactgtg cggcagctgg | 1860 |
| aggccattgt gcgcatcgcg gaagccctca gcaagatgaa gctgcagccc ttcgccacag | 1920 |
| aggcagatgt ggaggaggcc ctgcggctct tccaagtgtc cacgttggat gctgccttgt | 1980 |
| ccggtaccct gtcaggggtg gagggcttca ccagccagga ggaccaggag atgctgagcc | 2040 |
| gcatcgagaa gcagctcaag cgccgctttg ccattggctc ccaggtgtct gagcacagca | 2100 |
| tcatcaagga cttcaccaag cagaaatacc ggagcacgc catccacaag gtgctgcagc | 2160 |
| tcatgctgcg gcgcggcgag atccagcatc gcatgcagcg caaggttctc taccgcctca | 2220 |
| agtgagtcgc gccgcctcac tggactcatg gactcgccca cgcctcgccc ctcctgccgc | 2280 |
| tgcctgccat tgacaatgtt gctgggacct ctgcctcccc actgcagccc tcgaacttcc | 2340 |
| caggcacccc cctttctgcc ccagaggaag gagctgtagt gtcctgctgc ctctgggcgc | 2400 |
| ccgcctctag cgcggttctg ggaagtgtgc ttttggcatc cgttaataat aaagccacgg | 2460 |

```
tgtgttcagg taaaaaaaaa aaaaaaaaaa aaaaaaaaaa aaaaaaaaaa aaaaaaaaaa    2520
aaaaaaaaaa aaaa                                                      2534
```

METHODS AND KITS

CROSS-REFERENCE TO RELATED APPLICATIONS

The present application is a national stage entry under 35 U.S.C. § 371 of International Application No. PCT/GB2016/051611, filed Jun. 1, 2016, which claims the benefit of United Kingdom Application No. 1509908.8, filed Jun. 8, 2015, and United Kingdom Application No. 1603567.7, filed Mar. 1, 2016, the entire contents of which are incorporated by reference in their entireties for all purposes herein.

FIELD OF THE INVENTION

The invention relates to methods for detecting the presence of a Mcm5 in a sample from a patient and for kits that may be used in such methods.

BACKGROUND OF THE INVENTION

Urological cancers (occasionally referred to as 'urinary system cancers') are a major and increasing epidemiological problem. Two of the most economically important urological cancers are bladder cancer and prostate cancer.

Prostate cancer is the second most common cancer in men after non-melanoma skin cancer, with over 35,000 new cases diagnosed each year in the UK; about 10,200 deaths annually are caused by prostate cancer. There are around 300,000 new cases in Europe, 190,000 in the US and 670,000 worldwide annually. Cancer Research UK report that a quarter of all new cases of cancer diagnosed in men in the UK are prostate cancers and 60% of new diagnoses are in men aged over 70 years. The most common form of the disease is adenocarcinoma. The 5-year survival rate is almost 80% in the UK. There is no known environmental cause but those with close relatives with prostate or breast cancer are more at risk of developing the disease. West African and Afro-Caribbean males have an increased risk of prostate cancer.

The symptoms of prostate cancer are similar to those caused by benign enlargement of the prostate gland, and include urgency to urinate, difficulty or pain in passing urine and rarely, blood in the urine or semen. However, in many men the disease remains symptomless until painful metastases form, predominantly in the bones.

Treatment depends on the stage and grade of the tumour and the patient's general health and age. Options include active surveillance, partial or radical prostatectomy, orchidectomy, hormone treatment, and radiotherapy such as brachytherapy. Orchidectomy and hormone treatment reduce or eliminate the production of testosterone, which is essential for tumour growth.

The definite diagnosis of prostate cancer requires a multifaceted approach. The current gold standard diagnostic test for prostate cancer is the histological examination of biopsy material. The decision to biopsy is based on age-related serum (Prostate Specific Antigen) PSA level and/or an abnormal digital rectal examination (DRE). DRE, in which the gland is palpated trans-rectally to examine for abnormal morphology is also non-specific. Tumours that are too small to alter the morphology of the gland will not be detected, and abnormal morphology or enlargement is also caused by non-malignant conditions. This is a problem in the art. Samples of the prostate gland are commonly taken using TRUS (trans-rectal ultra sound)-guided needle biopsy. A number of needle cores are taken, typically up to 12, in order to maximize the area of the gland sampled. The procedure is carried out in the outpatients department under local anaesthesia by a urologist with the aid of a nurse or healthcare assistant. This procedure suffers from drawbacks including being somewhat painful for the patient, and exposing the patient to a risk of sepsis and/or bleeding. The tissue cores are microscopically examined in a laboratory for the presence of malignant cells, which has the problem of being labour intensive and requiring highly trained cytologists, as well as being vulnerable to human error.

It can be appreciated that biopsies are invasive and costly. There is a need in the art for a more cost-effective, reliable and/or non-invasive tool for the diagnosis and/or surveillance of urological cancer such as prostate cancer. Known alternate and/or less invasive diagnostic procedures for prostate cancer involve the analysis of specific biological markers ('biomarkers').

An example of a nucleic acid biomarker of prostate cancer is the PCA3 (prostate cancer gene 3) test. This urinary assay identifies non-coding mRNA from the PCA3 gene that is overexpressed in prostate cancer (Hessels & Schalken, The use of PCA3 in the diagnosis of prostate cancer. Nat Rev Urol, 6, 255-61; 2009). The PCA3 test (Gen-Probe, Inc) relies on the analysis of a first-catch urine specimen produced after a defined form of prostate massage used to express prostatic secretions, which contain epithelial cells into the urethra. As a diagnostic for prostate cancer PCA3 has a ROC (receiver operating characteristic curve) value of 0.68 (Chun et al, Prostate Cancer Gene 3 (PCA3): development and internal validation of a novel biopsy nomogram. Eur Urol; 2009 vol 56 p 659-668) which is similar to that for the PSA test discussed below. However, the PCA3 test is costly and not amenable to point-of-care use, which are problems with this prior art technique.

An example of a protein biomarker, which is frequently used to indicate the presence of prostate cancer is PSA (Prostate Specific Antigen). Symptomatic patients presenting in primary care are typically given a serum PSA test and a DRE. However, PSA is not specific for prostate cancer. PSA is a constitutively expressed tissue specific intracellular enzyme. A low concentration of PSA is present in the serum of men with healthy prostate glands. A raised level of PSA in serum occurs due to leakage from the prostate gland and is an indication of the relative size of the gland. Raised PSA can occur in non-malignant conditions such as benign prostatic hyperplasia and prostatitis and also in prostate cancer. As men grow older, the volume of the gland increases resulting in rising PSA levels in the absence of malignant disease. In a recent study it was found that 60-70% of 'positive' PSA tests (serum level of PSA greater than 4 ng/mL) were not associated with cancer (Kilpeläinen et al., False-positive screening results in the Finnish prostate cancer screening trial, British Journal of Cancer. 102, 469-474; 2010). The high rate of false positive results leads to many unnecessary biopsy operations and renders the test inappropriate for population screening. In addition the PSA test fails to detect a significant number of cases of prostate cancer, particularly in younger men. The accuracy of the PSA test as measured in ROC (receiver operating characteristic) analysis is 0.678 (Thompson et al., Operating characteristics of a prostate-specific antigen in men with an initial PSA level of 3.0 ng/ml or lower. JAMA, 294, 66-70; 2005). In the UK, PSA tests are usually carried out in hospital laboratories although rapid point-of-care assays are available.

Bladder cancer is the fourth most common cancer in men and the ninth most common cancer in women and results in significant morbidity and mortality (Jemal et al. CA Cancer J Clin. 2007. 57:43-66.). Most patients with bladder cancer receive the diagnosis after they present with gross or microscopic haematuria or with other irritative voiding symptoms, such as frequency and dysuria. At initial diagnosis, approximately 70% of patients have bladder cancers that are confined to the epithelium or subepithelial connective tissue. These cancers can be managed with endoscopic resection and intravesical therapy. The recurrence rate for these tumours ranges from 50% to 70% and 10% to 15% of cases progress to muscle invasion over a 5-year period (Shariat et al., 2008. Rev Urol. 10:120-135). Recurrence may be seen locally and more rarely in the upper urinary tract even after several years, necessitating lifelong surveillance. The remaining 30% of patients have muscle-invasive cancer at initial diagnosis. Of this population, 50% have distant metastasis within 2 years, and 60% die within 5 years despite treatment.

The definite diagnosis of bladder cancer requires a combination of procedures. Presently there are no methods to identify accurately and easily the presence of early bladder cancer. Screening for bladder cancer in patients who present to the urology clinic with appropriate symptoms is currently done with urinalysis, cystoscopy and a scanning procedure such as abdominal ultrasound, intravenous urogram, computed tomography or magnetic resonance imaging. Urine cytology, in which cells from urine samples are examined microscopically, is used occasionally. Cystoscopy, the mainstay for the detection of bladder cancer, is a relatively short, minimally traumatic procedure performed with local urethral anaesthesia, which identifies nearly all papillary and sessile lesions. Nevertheless, it is still invasive and a cause of discomfort and distress to the patient. In addition, cystoscopy may be inconclusive at times because of the grossly abnormal appearance of the bladder mucosa, especially in patients with an indwelling catheter or active inflammation, and it is unable to detect cancers within the ureters. Although considered the gold standard for diagnosis of bladder cancer because it allows direct visualization and biopsy of the bladder urothelium, cystoscopy has an appreciable false-negative rate either from operator error or from small areas of "carcinoma in situ", which may be difficult to detect. (van der Poel & Debruyne. Curr Opin Urol. 2001; 11:503-509; Herr. BJU Int. 1999; 84:1102-1103.)

In urine cytology for bladder cancer, exfoliated cells can be investigated for the presence of specific cell-surface antigens, nuclear morphology, gene expression or other biological markers. Urine cytology has a high sensitivity and specificity for the detection of high-grade bladder cancer, but it lacks the sensitivity to detect low grade tumours (Wiener et al. Acta Cytol. 1993; 37:163-169). The accuracy of urine cytology in predicting bladder cancer recurrence may vary widely, in part because there is an element of subjectivity in the interpretation of the results. Hence, cytology is not ideal for screening for and surveillance of bladder cancer.

Mcm5 is a biomarker for cancer (WO99021014). A raised level of Mcm proteins such as Mcm5 in urine sediment is associated with malignant changes in the prostate gland. Hence raised levels of these Mcm proteins could be used to detect prostate cancer. Using DELFIA® (Dissociation-Enhanced Lanthanide Fluorometric Immunoassay) and anti-Mcm5 monoclonal antibodies 4B4 and 12A7 in a double antibody assay, Dudderidge et al. (BJC, 103, 701-707; 2010) investigated the use of Mcm5 as a urinary biomarker for prostate cancer detection and concluded that it 'seems to be a simple, accurate and non-invasive method for identifying patients with prostate cancer'. Compared with the PSA test, which has a specificity of 30%, the specificity of Mcm5 was estimated at between 73% and 93%. Importantly, benign prostatic hyperplasia did not generate false positive results, which is a disadvantage of the PSA test.

A raised level of Mcm proteins such as Mcm5 in urine sediment is associated with malignant changes in the prostate gland. Hence raised levels of these Mcm proteins could be used to detect prostate cancer. Using DELFIA® (Dissociation-Enhanced Lanthanide Fluorometric Immunoassay) and anti-Mcm5 monoclonal antibodies in a double antibody assay, Dudderidge et al. (BJC, 103, 701-707; 2010) investigated the use of Mcm5 as a urinary biomarker for prostate cancer detection and concluded that it 'seems to be a simple, accurate and non-invasive method for identifying patients with prostate cancer'. Compared with the PSA test, which has a specificity of 30%, the specificity of Mcm5 was estimated at between 73% and 93%. Importantly, benign prostatic hyperplasia did not generate false positive results, which is a disadvantage of the PSA test. The assessment of Mcm5 and other Mcm proteins currently requires a specialised laboratory with sophisticated instrumentation and highly skilled operatives, thus the assay is not suited to the pathology laboratory or point-of-care applications.

This is further compounded by the complicated methods which are used to prepare samples for analysis by detection of biomarkers. Since Mcm proteins are present in cells, the Mcm proteins must be released from cells in a sample such as a urine sample. A method for preparing such samples is disclosed in, Dudderidge et al. (BJC, 103, 701-707; 2010) which describes that the samples must be processed using a large number of steps including (1) centrifugation at 1500 g for 5 min at 4° C., (2) discarding the supernatant, (3) washing the cell pellet three times with 500 µl of PBS, (3) resuspending the cell pellets in 250 µl or 500 µl of processing buffer (PBS, 0.4% sodium dodecyl sulphate and 0.02% sodiumqzide), (4) incubating the resuspended samples at 95° C. for 45 minutes, (5) shearing the DNA in the sample by passing the lysis through a 21-gauge needle, (6) digestion of the nucleic acids with DNase I and RNase A for 2 h at 37° C., and (7) centrifugation at 15000 g for 10 min. This method is also seen in other documents such as Stoeber et al 2002 (Journal of the National Cancer Institute, 94, 1071-1079; 2002). This urine sample preparing method involves multiple steps using multiple reagents and is extremely time-consuming. Typically these methods take at least two hours. Thus, there is a need for a method to prepare urine samples which is considerably less onerous. Such a method would be more suited to pathology laboratory or point-of-care applications.

The present assays for detection of Mcm proteins, particularly Mcm5, require the use of DELFIA technology which is complicated to use and involves expensive equipment and reagents. Thus, an assay based on DELFIA is not suitable for pathology laboratory or point-of-care applications and there is a need for an assay that is suitable for such applications.

Furthermore, there is no disclosure of sequences of antibodies that bind to Mcm5 in a highly specific manner and, therefore, are suitable for designing a high affinity assay for Mcm5.

SUMMARY OF THE INVENTION

The present invention provides methods, compositions and kits useful for the early detection of urological cancer such as prostate cancer without the need for invasive surgical procedures. The methods and compositions are suitable for use in the clinical laboratory and/or for point-of-care applications.

The present inventors have demonstrated that the complicated urine sample preparation methods described in the prior art are not required to release biomarkers such as Mcm5 from cells in samples such as urine samples. Rather, all that is required is to expose the sample to a lysis buffer which is capable of releasing the biomarker from cells in the sample. This is much simpler than the prior art methods. According to the present invention, in some embodiments the cells in a sample (such as a urine sample) may be prepared and lysed by the addition of a single lysate buffer.

The present inventors have also demonstrated that an Mcm protein assay which does not use immunofluorescence can accurately detect whether a subject has a urological cancer. This is beneficial over prior art techniques which use Europium labels and DELFIA detection. Such methods are expensive and complicated and thus unsuitable for use in pathology laboratory or point-of-care applications.

In addition, the present invention relates to antibodies which bind to biomarkers such as an Mcm protein, for example Mcm5, in a highly specific manner. These antibodies are useful in detecting levels of the biomarker and the present inventors have demonstrated that these antibodies may be used in the methods of the invention. The inventors have demonstrated that these antibodies bind to Mcm5 from samples that have been exposed to a lysis buffer which is capable of releasing the biomarker from cells in the sample. The present invention relates to antibodies that bind to Mcm5 but bind to different epitopes to one another (12A7 binds to SEQ ID NO: 1 and 4B4 binds to SEQ ID NO: 2). Such antibodies are advantageous as they can be used in assays to detect Mcm5 (or similar Mcm proteins containing these epitopes). In particular, these antibodies can be used in the methods of the invention, for example sandwich (two-site) assays.

However, in order for such an assay to be developed, two antibodies that bind to Mcm5 must be identified. Ideally, these two antibodies must bind to different epitopes to one another, but also the two different epitopes to which the two antibodies bind must be spatially positioned such that both antibodies may bind to Mcm5 at the same time (without substantial steric hindrance). The present inventors have developed two such antibodies (named 12A7 and 4B4). These two antibodies bind to SEQ ID NO: 1 and SEQ ID NO: 2 respectively. SEQ ID NO: 1 and SEQ ID NO: 2 represent two different Mcm5 epitopes which are spatially arranged on Mcm5 to allow the two antibodies to bind to Mcm5 at the same time. This is demonstrated in Examples 2 and 3. The present inventors are the first to determine two Mcm5 epitopes which are arranged such that antibodies to each epitope may bind simultaneously. Furthermore, the inventors are the first to provide sequences of two antibodies that can bind independently to Mcm5.

Accordingly in a first aspect of the invention there is provided a method for detecting the presence of Mcm5 in a sample from a subject, the method comprising:
(a) preparing a sample from said subject wherein preparing the sample comprises exposing the sample to a lysis buffer;
(b) performing an assay to determine the concentration of Mcm5 by exposing the sample to a first monoclonal antibody and/or a second monoclonal antibody and measuring the amount of Mcm5 that binds to the first monoclonal antibody and/or the second monoclonal antibody; and
(c) comparing the concentration of Mcm5 determined in step (b) to reference values; wherein the first monoclonal antibody and the second monoclonal antibody bind to Mcm5.

In a second aspect of the invention there is provided a kit comprising a lysis buffer which is capable of releasing Mcm5 from cells in a sample, a first monoclonal antibody and a second monoclonal antibody wherein the first monoclonal antibody is an antibody which:
(i) binds to a polypeptide having an amino acid sequence of SEQ ID NO: 1;
(ii) comprises at least one Complementary Determining Region (CDR) selected from the group consisting of:
  (a) 12A7 CDRH1 which has a sequence of SEQ ID NO: 9 or a sequence that differs from SEQ ID NO:9 by a single amino acid substitution;
  (b) 12A7 CDRH2 which has a sequence of SEQ ID NO: 11 or a sequence that differs from SEQ ID NO:11 by a single amino acid substitution;
  (c) 12A7 CDRH3 which has a sequence of SEQ ID NO: 13 or a sequence that differs from SEQ ID NO:13 by a single amino acid substitution;
  (d) 12A7 CDRL1 which has a sequence of SEQ ID NO: 3 or a sequence that differs from SEQ ID NO:3 by a single amino acid substitution;
  (e) 12A7 CDRL2 which has a sequence of SEQ ID NO: 5 or a sequence that differs from SEQ ID NO:5 by a single amino acid substitution; and
  (f) 12A7 CDRL3 which has a sequence of SEQ ID NO: 7 or a sequence that differs from SEQ ID NO:7 by a single amino acid substitution;
(iii) comprises a heavy chain variable region having a sequence at least 85%, 90%, 95%, 98%, 99% or 100% identical to SEQ ID NO: 29;
(iv) comprises a light chain variable region sequence having a sequence at least 85%, 90%, 95%, 98%, 99% or 100% identical to SEQ ID NO: 27; or
(v) competes with the antibody of (i), (ii), (iii) or (iv);
and the second monoclonal antibody is an antibody which:
(i) binds to a polypeptide having an amino acid sequence of SEQ ID NO: 2;
(ii) comprises at least one Complementary Determining Region (CDR) selected from the group consisting of:
  (a) 4B4 CDRH1 which has a sequence of SEQ ID NO: 21 or a sequence that differs from SEQ ID NO:21 by a single amino acid substitution;
  (b) 4B4 CDRH2 which has a sequence of SEQ ID NO: 23 or a sequence that differs from SEQ ID NO:23 by a single amino acid substitution;
  (c) 4B4 CDRH3 which has a sequence of SEQ ID NO: 25 or a sequence that differs from SEQ ID NO:25 by a single amino acid substitution;
  (d) 4B4 CDRL1 which has a sequence of SEQ ID NO: 15 or a sequence that differs from SEQ ID NO:15 by a single amino acid substitution;
  (e) 4B4 CDRL2 which has a sequence of SEQ ID NO: 17 or a sequence that differs from SEQ ID NO:17 by a single amino acid substitution; and
  (f) 4B4 CDRL3 which has a sequence of SEQ ID NO: 19 or a sequence that differs from SEQ ID NO:19 by a single amino acid substitution;
(iii) comprises a heavy chain variable region having a sequence at least 85%, 90%, 95%, 98%, 99% or 100% identical to SEQ ID NO: 33;
(iv) comprises a light chain variable region sequence having a sequence at least 85%, 90%, 95%, 98%, 99% or 100% identical to SEQ ID NO: 31; or (v) competes with the antibody of (i), (ii), (iii) or (iv).

DETAILED DESCRIPTION

Methods for Detecting the Presence of a Mcm5 in a Sample from a Subject

The present invention provides a method for detecting the presence of Mcm5 indicative of a urological cancer in a subject, the method comprising:
(a) preparing a sample from said subject wherein preparing the sample comprises exposing the sample to a lysis buffer;
(b) performing an assay to determine the concentration of Mcm5 by exposing the sample to a first monoclonal antibody and/or a second monoclonal antibody and measuring the amount of Mcm5 that binds to the first monoclonal antibody and/or the second monoclonal antibody; and
(c) comparing the concentration of Mcm5 determined in step (b) to reference values; wherein the first monoclonal antibody and the second monoclonal antibody bind to Mcm5.

In some embodiments the presence of higher than normal levels of Mcm5 in the sample is indicative of urological cancer. Whether or not the level of Mcm5 in the sample is higher than normal may be determined by comparing the amount detected with the amount detected in a reference sample. In some embodiments the method is a method for detection of a urological cancer.

Minichromosome Maintenance Proteins (Mcm5)

Minichromosome maintenance (MCM) proteins have previously been used as diagnostic biomarkers for cervical cancer. Elevated levels of a minichromosome maintenance complex (MCM) family protein such as the nuclear protein Mcm5 can be used to detect bladder cancer cells in urine sediments as well as prostate cancer. The assessment of Mcm5 is often carried out in a specialised laboratory with sophisticated instrumentation and highly skilled operatives (Stoeber et al. JNCI. 2002: 94: 1071-1079) and this style of analysis can be expensive or impractical to carry out in the pathology laboratory or point-of-care applications. However, it is an advantage that the inventors of the instant application have succeeded in developing a modified double-antibody sandwich ELISA format using a pair of specific monoclonal antibodies that is suited to the pathology laboratory and point-of-care applications to measure accurately Mcm5 levels in urinary sediments. However, this preferred type of assay does not confine the analysis of Mcm5 to this mode, according to the invention Mcm5 may be assayed according to any suitable method known in the art.

MCM proteins 2-7 comprise part of the pre-replication complexes which form on chromatin and which are essential prerequisites, or licensing factors, for subsequent DNA replication. The MCM protein complexes act as replicative helicases and thus are core components of the DNA replication machinery. MCMs are upregulated in the transition from the G0 to G1/S phase of the cell cycle and actively participate in cell cycle regulation. The MCM proteins form an annular structure around the chromatin.

Figure 1:
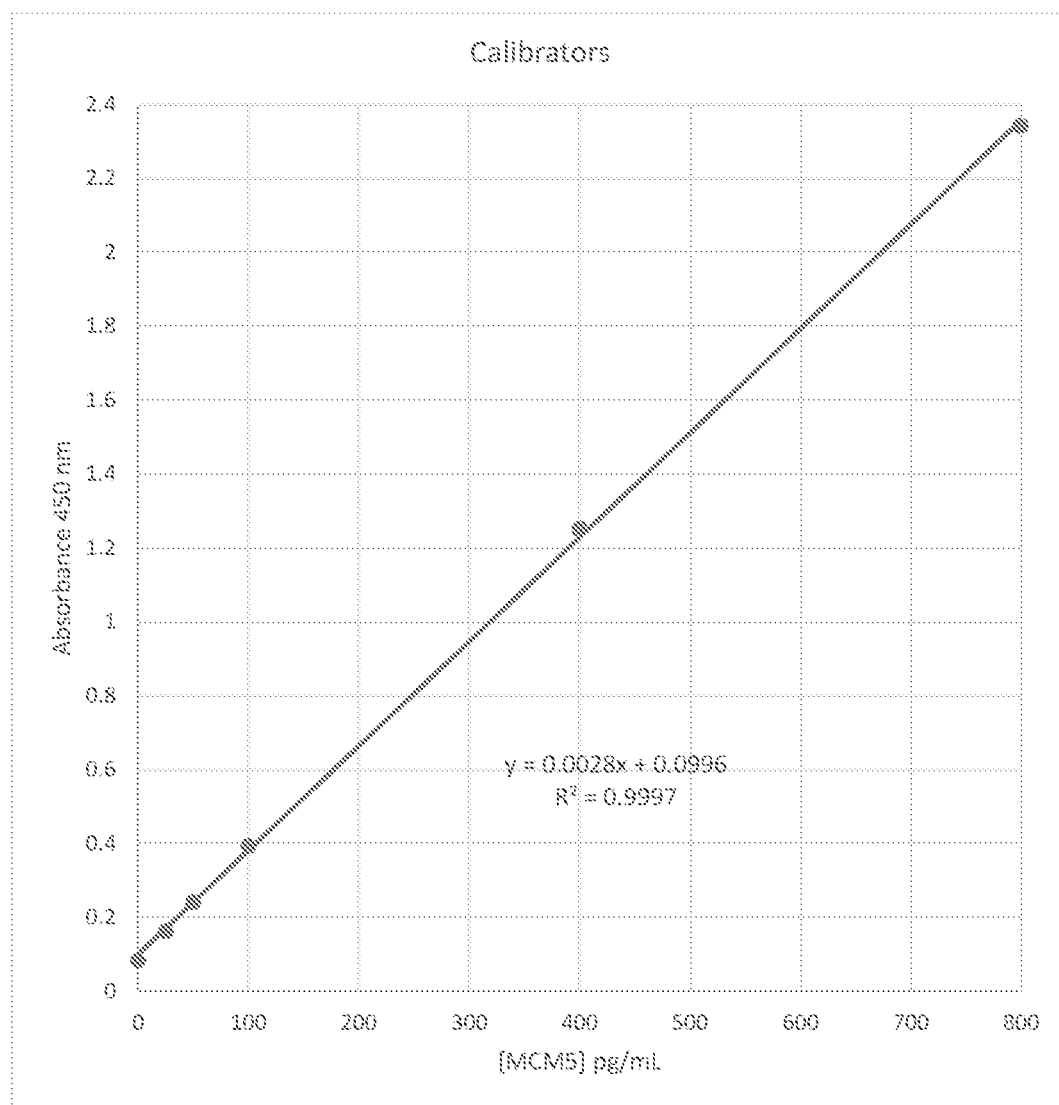
FIG. 1 shows a graph describing the absorbance at 450 nm of different concentrations of Mcm5.

The human Mcm5 gene maps to 22q13.1 and the mature Mcm5 protein consists of 734 amino acids (SEQ ID NO: 1; FIG. 1: UNIPROT P33992: HUMAN DNA replication licensing factor MCM5). The term "Mcm5" refers to a polypeptide of SEQ ID NO: 35, a polypeptide 85%, 90%, 95%, 98% or 100% identity to SEQ ID NO: 35. Mcm5 may be encoded by a polynucleotide having a sequence 85%, 90%, 95%, 98% or 100% identical to SEQ ID NO: 36.

Preparing a Sample from Said Subject

The method of the invention comprises a step of preparing a sample from the subject wherein preparing the sample comprises exposing the sample to a lysis buffer. The phrase "preparing the sample" refers to steps taken to release Mcm5 from cells within the sample in order to allow for step (b) of the invention (performing an assay to determine the concentration of Mcm5) to take place. This step comprises exposing the sample to a lysis buffer. Suitably the step of "preparing the sample" comprises a step of concentrating cells in the urine sample. Optionally the cells are concentrated by filtration or by centrifugation.

The term 'exposing the sample to a lysis buffer' can be considered to refer to manipulating the urine sample in such a way that the cells within the urine sample (or a substantial portion of these cells) are in contact with the lysis buffer.

Preferably the sample is a urine sample. Suitably, the sample is centrifuged to provide a sample pellet, the supernatant is discarded and the sample pellet is re-suspended in the lysis buffer. Alternatively, for example, concentrated buffer components are added to a liquid urine sample to form a solution comprising the sample exposed to the lysis buffer.

Optionally the method of the invention comprises a step of "providing a sample from a subject". Preferably this step is non-invasive (not-surgical), for example collection of urine. The sample may comprise any biological fluid such as blood, serum, saliva, semen, urine or urinary sediment, or an extract prepared from one of such fluids. The sample is suitably urine.

Mcm5 is typically found in the nuclei of cells present in urine. Thus, suitably the sample comprises cells within the urine. More suitably, those cells may be concentrated by any known technique common in the art, such as filtration or more suitably centrifugal collection of the cells from urine. Enriching the cells from the urine may increase the signal, and may facilitate detection. When testing for prostate cancer, most suitably the sample is first catch urine, such as may be obtained after massage of the prostate gland (when the subject is male). Even more suitably, the sample may comprise the first few milliliters of first catch urine. In other words, suitably the sample may comprise first pass urine, suitably first pass urine produced after massage of the prostate gland. Even more suitably, the sample may comprise urinary sediment such as sedimented cells collected from urine (such as from total urine, or from first catch urine as explained above).

In one embodiment a sample comprising cells is prepared using a process consisting of the following steps: a. centrifugation of the sample to provide a sample pellet; and b. resuspension of the pelleted cells from the sample in a lysis buffer.

Suitably the sample is centrifuged for between 1 minute and 30 minutes at between 500 g and 5000 g, for between 1 minute and 20 minutes at between 750 g and 2500 g, for between 3 minutes and 10 minutes at between 750 g and 2000 g, or for around 5 minutes at 1500 g. Suitably the pellet is resuspended using an adjustable pipette with a disposable tip.

In one embodiment the method does not comprise incubation of the sample at a temperature greater than 90° C. for around 45 minutes. Optionally the method does not comprise incubation of the sample at a high temperature. In one embodiment the high temperature is a temperature greater than 50° C., greater than 60° C., greater than 70° C., greater than 80° C., greater than 90° C., between 50° C. and 120° C., between 60° C. and 110° C., between 70° C. and 100° C., or between 80° C. and 100° C. Optionally the method does not comprise incubation of the sample at a high temperature for more than 30 minutes, more than 35 minutes, more than 40 minutes, more than 45 minutes, between 30 minutes and 2 hours, between 35 minutes and 2 hours, or between 40 minutes and 2 hours.

In a further embodiment the method does not comprise shearing the nucleic acids by passing the sample through a 21 gauge needle. In a further embodiment the method does not comprise exposing the sample to mechanical shearing.

Optionally the method does not comprise incubation of the urine sample at a temperature greater than 90° C. for greater than 45 minutes, shearing nucleic acids in the urine sample by passing the urine sample through a 21 gauge needle, digesting the nucleic acids by exposing the urine sample to DNase I or RNase A, centrifuging the sample at 15,000 g for 10 minutes, wherein the lysis buffer is not PBS containing 0.4% sodium deoxycholate and 0.02% sodium azide.

In a further embodiment the method does not comprise digesting the nucleic acids by exposing the sample to DNase I or RNase A.

The phrase 'does not comprise digesting the nucleic acids by exposing the urine sample to DNase I or RNase A' means the sample should not be exposed to a concentration of DNase I or RNase A that is effective to cause significant digestion of the nucleic acids in the sample. Preferably the sample is not exposed to more than 20 U/ml DNase I or more than 1 µg/mL RNase A. Suitably the sample is not exposed to more than 1 U/ml, more than 5 U/ml, more than 10 U/ml, more than 15 U/ml, between 1 U/ml and 500 U/ml, between 5 U/ml and 250 U/ml, between 10 U/ml and 100 U/mL or between 15 U/ml and 100 U/ml of DNase I. Suitably the sample is not exposed to more than 0.1 µg/mL, more than 0.2 µg/mL, more than 0.5 µg/mL, more than 0.7 µg/mL, between 0.1 µg/ml and 100 µg/ml, between 0.5 µg/mL and 50 µg/mL or between 0.5 µg/mL and 25 µg/mL of RNase A.

In a further embodiment the method does not comprise centrifuging the sample at 15,000 g for ten minutes. In a further embodiment the method does not comprise centrifuging the sample. In a further embodiment the method does not comprise centrifuging the sample at more than 10,000 g, more than 12,000 g, more than 14,000 g or more than 14,500 g. In a further embodiment the method does not comprise centrifuging the sample for more than 2 minutes, more than 5 minutes, more than 7 minutes or more than 8 minutes.

Lysis Buffers

Lysis buffers are generally buffers which are used for the purpose of lysing cells. The lysis buffer is preferably compatible with the method used for subsequent analysis. For example, where the analysis method is double-antibody sandwich ELISA, the lysis buffer must not degrade the capture antibody bound to the surface of the microtitre plate. Lysis buffers generally but not exclusively comprise one or more detergents (also known as surfactants), one or more salts and a buffering agent. The concentrations of these components affect the efficacy of the lysis buffer. Preferably the lysis buffer is capable of releasing Mcm5 from cells in the sample.

In a preferred embodiment of the invention the lysis buffer is capable of releasing a biomarker such as Mcm5 from cells in the sample. A lysis buffer will be considered to be "capable of releasing a No/marker such as Mcm5 from cells in the sample" if the amount of the biomarker such as Mcm5 released is greater than 40%, 50%, 60%, 70%, or 80% the amount released when a buffer containing 0.08% sodium deoxycholate. 0.08% CHAPS, 2 mM EDTA, 150 mM Trizma pH 7.6 is used. In an embodiment a lysis buffer will be considered to be "capable of releasing a biomarker such as Mcm5 from cells in the sample" if the amount of a biomarker such as Mcm5 released is greater than 40%, 50%, 60%, 70%, or 80% the amount released when a buffer containing 101 mM Tris (pH 7.6), 200 mM NaCl, 2.5% BSA, 0.1% TRITON™ X-100 and 0.09% Sodium azide is used. The amount of a biomarker such as Mcm5 that is released using a. lysis buffer may be determined by assaying the amount present after exposure to the lysis buffer and comparing it to a reference sample (Preferably a sample which is substantially the same or identical to the first sample) which has been exposed to a buffer containing 0.08% sodium deoxycholate, 0.08% CHAPS, 2 mM EDTA, 150 mM Trizma pH 7.6. In an embodiment the amount of a biomarker such as Mcm5 that is released using a lysis buffer may be determined by assaying the amount present after exposure to the lysis buffer and comparing it to a reference sample (Preferably a sample which is substantially the same or identical to the first sample) which has been exposed to a buffer containing 10 mM Tris (pH 7.6), 200 mM NaCl, 2.5% BSA, 0.1% TRITON™ X-100 and 0.09% Sodium azide. The amount of a biomarker such as Mcm5 that is released may be measured using a sandwich ELISA assay such as the assay described in Example 4. The antibodies used in the sandwich assay should be antibodies that bind to the biomarker such as Mcm5, for example a first monoclonal antibody or second monoclonal antibody according to the invention. Preferably 12A7 and 4B4 antibodies are used.

In an even more preferred embodiment of the invention the lysis buffer is capable of releasing Mcm5 from cells in the urine sample and does not substantially degrade the Mcm5 protein. A buffer can be considered to not substantially degrade Mcm5 protein if the amount of intact Mcm5 present after exposure of the sample to the lysis buffer is greater than 40%, 50%, 60%, 70%, or 80% the amount of intact Mcm5 after exposure to a buffer containing 0.08% sodium deoxycholate, 0.08% CHAPS, 2 mM EDTA, 150 mM Trizma pH 7.6. Mcm5 protein can be considered to be intact, if the binding site for antibodies that bind to SEQ ID NO: 1 and SEQ ID NO: 2 (such as the first monoclonal antibody and second monoclonal antibody or antibodies 12A7 and 4B4) are present. It is within the capabilities of the skilled person to determine how much Mcm5 within a sample is degraded. The sample should be tested to see whether the Mcm5 within the sample can bind to the first monoclonal antibody and the second monoclonal antibody according to the invention. This may be measured using a sandwich ELISA assay such as that described in Example 4. The antibodies used in the sandwich assay should be antibodies that bind to Mcm5, for example a first monoclonal antibody or second monoclonal antibody of the invention. Preferably 12A7 and 4B4 antibodies are used.

In one embodiment the lysis buffer is capable of releasing Mcm5 from cells in a fresh sample. The term "fresh sample" refers to a sample that has not been frozen. Preferably, the "fresh sample" has been obtained from a patient less than 10 days, less than 5 days, less than 2 days or less than 1 day prior to its use in the methods of the invention. In one embodiment the cells are exposed to the lysis buffer and then frozen before further treatment. For example, the urine sample may be concentrated by centrifugation followed by discarding the supernatant and then the lysis buffer may be added to the concentrated cells. Preferably the frozen sample is thawed prior to a step of performing an assay to determine the concentration of the at least one biomarker in the urine sample. Preferably the sample is frozen for at least 1 hour, at least 1 day, at least 5 days or at least 10 days prior to a step of performing an assay to determine the concentration of the at least one biomarker in the urine sample. Preferably the sample is frozen for between 1 hour and 1 year, between 1 hour and 6 months, between 1 day and 3 months or around one week prior to a step of performing an assay to determine the concentration of the at least one biomarker in the urine sample.

In an embodiment of the invention the lysis buffer is Cytobuster™ Protein Extraction Reagent.

In one embodiment the lysis buffer does not comprise sodium azide. In one embodiment the lysis buffer is not PBS containing 0.4% sodium deoxycholate and 0.02% sodium azide.

In one embodiment the lysis buffer comprises a detergent (also referred to as a surfactant). In general detergents are compounds that are known to disrupt cell walls. Detergents are amphiphilic having both hydrophobic and hydrophilic regions. Suitable detergents are well known to the person of skill in the art. Suitably the detergent is an anionic detergent, a cationic detergent, a non-ionic detergent or a zwitterionic detergent. Suitably the detergent is selected from the group consisting of sodium deoxycholate, 3-[(3-Cholamidopropyl) dimethylammonio]-1-propanesulphonate (CHAPS), alkylbenzenesulphonates, sodium dodecylbenzenesulphonate, a TWEEN® detergent (such as polyoxyethylene (20), sorbitan monolaurate or TWEEN® 20), and a TRITON™ detergent (such as polyethylene glycol p-(1, 1, 3, 3,-tetramethylbutyl)-phenyl ether or TRITON™ X-100).

Suitably the detergent comprises sodium deoxycholate. Suitably the detergent comprises CHAPS. Suitably the detergent comprises sodium deoxycholate and CHAPS. Suitably the lysis buffer comprises sodium deoxycholate at a concentration between 0.01% and 0.15%, between 0.03% and 0.10%, between 0.05% and 0.09%, or about 0.08%. Suitably the lysis buffer comprises CHAPS at a concentration between 0.01% and 0.15%, between 0.03% and 0.10%, between 0.05% and 0.09%, or about 0.08%. Suitably the detergent comprises TRITON™ X-100. Preferably the detergent comprises TRITON™ X-100 at a concentration between 0.01% and 25%, between 0.01% and 10%, between 0.05% and 5%, between 0.05% and 1%, between 0.05% and 0.5%, between 0.075% and 0.125% or around 0.1%. Suitably the detergent consists of TRITON™ X-100. Preferably the detergent consists of TRITON™ X-100 at a concentration between 0.01% and 25%, between 0.01% and 10%, between 0.05% and 5%, between 0.05% and 1%, between 0.05% and 0.5%, between 0.075% and 0.125% or around 0.1%. Suitably the detergent comprises a polysorbate, preferably polysorbate 20 (also known as TWEEN® 20. Suitably the detergent comprises polysorbate at a concentration between 0.01% and 5%, between 0.02% and 1%, between 0.03% and 0.07% or around 0.05%. Suitably the detergent comprises sodium deoxycholate or sodium dodecylsulphate. For example the detergent may comprise sodium deoxycholate or sodium dodecylsulphate at a concentration between 0.1% and 20%, between 0.5% and 10%, between 0.5% and 5%, between 0.75% and 1.25% or around 1%.

In a further embodiment the lysis buffer comprises a chelating agent. In a further embodiment the lysis buffer does not comprise a chelating agent. Chelating agents are multidentate ligands which can coordinate metal ions. Suitably the chelating agent is EDTA (ethylenediaminetetraacetic acid). Optionally the lysis buffer comprises EDTA at a concentration between 0.5 mM and 10 mM, between 1 mM and 5 mM, between 1.5 mM and 3 mM, or about 2 mM.

In a further embodiment the lysis buffer comprises a buffer component. A buffer component can be considered to be any component which maintains the pH of the lysis buffer at a pH varying by less than 2.0 pH units, 1.5 pH units or 1.0 pH units. Examples of buffers which are suitable for this purpose are well known to the person skilled in the art. In an embodiment the buffer component is a buffer selected from the group consisting of TAPS (3-{[tris(hydroxymethyl) methyl]amino}propanesulphonic acid), Bicine (N,N-bis(2-hydroxyethyl)glycine), Tris (tris(hydroxymethyl)methylamine), Tricine (N-tris(hydroxymethyl(methylglycine), TAPSO (3-[N-Tris(hydroxymethyl)methylamino]-2-hydroxypropanesulphonic acid, HEPES (4-2-hydroxyethyl-1-piperazineethanesulphonic acid) and MOPS (3-(N-morpholino)propanesulphonic acid. Suitably the buffer component comprises Tris, phosphate buffered saline (PBS), MOPS, bicarbonate or HEPES buffer. Suitably the buffer component comprises Tris, PBS, MOPS or bicarbonate buffer. Suitably the buffer component comprises Tris, PBS or bicarbonate buffer. In one embodiment the buffer component is Trizma or Tris buffer. In one embodiment the buffer component comprises or consists of Trizma or Tris buffer. Trizma may refer to Trizma® Pre-set crystals pH 7.6' (Sigma-Aldrich Cat. No. T7943). In a further embodiment the buffer component maintains the pH of the buffer at a pH between pH 4 and pH 9, between pH 5 and pH 8, between pH 6 and pH 8, or around pH 7.6. Optionally the buffer component is Trizma or Tris buffer, and the buffer component maintains the pH of the lysis buffer between pH 4 and pH 9, between pH 5 and pH 8, between pH 6 and pH 8, or around pH 7.6. Optionally the buffer component comprises or consists of Trizma or Tris buffer, and the buffer component maintains the pH of the lysis buffer between pH 4 and pH 9, between pH 5 and pH 8, between pH 6 and pH 8, or around pH 7.6.

Preferably the buffer component comprises tris buffer, for example at a concentration greater than 5 mM, between 5 mM and 350 mM, between 200 mM and 300 mM, between 225 mM and 275 mM between 10 mM and 25 mM, between 8 mM and 12 mM, around 10 mM or around 250 mM. Preferably the buffer component consists of tris buffer, for example at a concentration greater than 5 mM, between 5 mM and 350 mM, between 200 mM and 300 mM, between 225 mM and 275 mM, between 10 mM and 25 mM, between 8 mM and 12 mM, around 10 mM or around 250 mM. Suitably the buffer component comprises phosphate buffered saline, for example at a concentration of between 5 mM and 250 mM, between 50 mM and 250 mM or around 100 mM.

In an embodiment the lysis buffer comprises sodium deoxycholate at a concentration between 0.01% and 0.15%, CHAPS at a concentration between 0.01% and 0.15%, EDTA at a concentration between 0.5 mM and 10 Mm, and Trizma or Tris buffer, wherein the Trizma or Tris buffer maintains the pH of the lysis buffer between pH 4 and pH 9. In a further embodiment the lysis buffer comprises sodium deoxycholate at a concentration between 0.05% and 0.09%, CHAPS at a concentration between 0.05% and 0.09%, EDTA at a concentration between 1.5 mM and 3 mM, and Trizma or Tris buffer, wherein the Trizma or Tris buffer maintains the pH of the lysis buffer between pH 6 and pH 8. In a further embodiment the lysis buffer comprises sodium deoxycholate at a concentration about 0.08%, CHAPS at a concentration about 0.08%, EDTA at a concentration about 2 mM, and Trizma or Tris buffer, wherein the Trizma or Tris buffer maintains the pH of the lysis buffer around pH 7.6.

In one embodiment the lysis buffer comprises a salt selected from the group consisting of sodium chloride, potassium chloride, magnesium chloride, sodium sulphate, potassium sulphate, magnesium sulphate, sodium acetate, potassium acetate, magnesium acetate, sodium phosphate, potassium phosphate or magnesium phosphate. Preferably the salt is a sodium salt or a potassium salt. Suitably the salt is sodium chloride or potassium chloride. Suitably the salt comprises or consists of sodium chloride or potassium chloride. Suitably the salt is at a concentration between 20 mM and 300 mM, between 150 mM and 300 mM, between 100 mM and 200 mM, between 150 mM and 250 mM, between 175 mM and 275 mM or around 200 mM. Preferably the salt is sodium chloride, for example at a concentration between 20 mM and 300 mM, between 150 mM and 300 mM, between 100 mM and 200 mM or around 200 mM. Preferably the salt comprises or consists of sodium chloride, for example at a concentration between 20 mM and 300 mM, between 150 mM and 300 mM, between 100 mM and 200 mM or around 200 mM.

In one embodiment the lysis buffer has an ionic strength of between 1 mM and 500 mM, between 50 mM and 450 mM, between 100 mM and 250 mM, between 100 mM and 175 mM, or between 125 mM and 175 mM. Various components of the buffer may contribute to this ionic strength. For example, the lysis buffer may comprise a buffer component (such as Tris) and an additional salt component (such as sodium chloride) and both of these components may contribute to the ionic strength of the lysis buffer.

In one embodiment the lysis buffer comprises a stabiliser. A "stabiliser" is a component that reduces the breakdown of proteins. For example, a stabiliser reduces the breakdown of Mcm5. Whether a buffer component stabilises Mcm5 can be tested using a sandwich ELISA assay such as the assay described in Example 4. For example, a sample may be exposed to a lysis buffer comprising the potential stabiliser and a control sample may be exposed to a lysis buffer lacking the potential stabiliser. The level of Mcm5 that can be detected after exposure is measured using the sandwich ELISA. If the level of Mcm5 in the sample having the buffer comprising the potential stabiliser is greater than the level of Mcm5 in the sample having the buffer that does not comprise the potential stabiliser, then the potential stabiliser is a stabiliser according to the present invention. A stabiliser of the invention may prevent the breakdown of Mcm5 such that 1%, 2%, 5%, 10%, 20% or 25% more Mcm5 is present after storage in a buffer comprising a stabiliser for 1 day, 3 days, 5 days, 1 week or 2 weeks (compared to a buffer that does not comprise the stabiliser).

The stabiliser may be a stabiliser selected from the group consisting of bovine serum albumin (BSA), foetal bovine serum (FBS) and a protease inhibitor. For example, protease inhibitors include 4-(2-aminoethyl)benzenesulphonyl fluoride hydrochloride (Petrabloc SC or AEBSF), a protease inhibitor cocktail (such as Sigma P8340) comprising AEBSF, aprotinin, bestatin hydrochloride, N-(trans-epoxysuccinyl)-L-leucine 4-guanidinobutylamide (E-64), leupeptin hemisulphate salt and pepstatin A, and Roche complete protease inhibitor. Preferably the stabiliser is BSA, for example at a concentration between 0.1% and 20%, between 0.1% and 10%, between 0.1% and 5%, between 1% and 3%, between 2.2% and 2.7% or around 2.5%. Preferably the stabiliser comprises or consists of BSA, for example at a concentration between 0.1% and 20%, between 0.1% and 10%, between 0.1% and 5%, between 1% and 3%, between 2.2% and 2.7% or around 2.5%.

The lysis buffer may comprise an antimicrobial agent. A component is an "antimicrobial agent" if it reduces the replication of microbes, for example bacteria, viruses or fungi. In one embodiment the antimicrobial agent is sodium azide or an isothiazolone. In one embodiment the antimicrobial agent comprises or consists of sodium azide or an isothiazolone. The isothiazolone may be 2-methyl-4-isothiazolin-3-one and/or 5-chloro-2-methyl-4-isothiazolin-3-one. Preferably the antimicrobial agent comprises sodium azide, for example at a concentration between 0.01% and 5%, between 0.02% and 1.5%, between 0.07% and 0.12% or around 0.09%. Preferably the antimicrobial agent consists of sodium azide, for example at a concentration between 0.01% and 5%, between 0.02% and 1.5%, between 0.07% and 0.12% or around 0.09%.

The lysis buffer may comprise:
(i) between 1 mM and 500 mM Tris:
(ii) between 5 mM and 500 mM sodium chloride;

(iii) between 0.1% and 20% BSA:
(iv) between 0.001% and 10% TRITON™ X-100; and
(v) between 0.001% and 1% sodium azide.
Alternatively, the lysis buffer may comprise:
(i) between 1 mM and 150 mM Iris;
(ii) between 50 mM and 400 mM sodium chloride;
(iii) between and 10% BSA:
(iv) between 0.01% and 5% TRITON™ X-100; and
(v) between 0.01% and 0.5% sodium azide.
Alternatively, the lysis butler may comprise:
(i) between 1 mM and 100 mM Iris;
(ii) between 100 mM and 300 mM sodium chloride
(iii) between 1% and 5% BSA;
(iv) between 0.01% and 1% TRITON™ X-100; and
(v) between 0.01% and 0.1% sodium azide.
The lysis buffer may comprise:
(i) around 10 mM Iris;
(ii) around 200 mM sodium chloride;
(iii) around 2.5% BSA;
(iv) around 0.1% TRITON X-100; and
(v) around 0.09% sodium azide.
The lysis buffer may consists of:
(i) between 1 mM and 500 mM Iris;
(ii) between 5 mM and 500 mM sodium chloride;
(iii) between 0.1% and 20% BSA;
(iv) between 0.001% and 10% TRITON™ X-100; and
(v) between 0.001% and 1 sodium azide.
Alternatively, the lysis buffer may consist of:
(i) between 1 mM and 150 mM Iris;
(ii) between 50 mM and 400 mM sodium chloride;
(iii) between 0.5% and 10% BSA;
(iv) between 0.01% and 5% TRITON™ X-100; and
(v) between 0.01% and 0.5% sodium azide.
Alternatively, the lysis buffer may consist of:
(i) between 1 mM and 100 mM Iris;
(ii) between 100 mM and 300 mM sodium chloride;
(iii) between 1% and 5% BSA;
(iv) between 0.01% and 1% TRITON™ X-100; and
(v) between 0.01% and 0.1% sodium azide.
The lysis buffer may consist of:
(i) around 10 mM iris;
(ii) around 200 mM sodium chloride;
(iii) around 2.5% BSA;
(iv) around 0.1% TRITON™ X-100; and
(v) around 0.09% sodium azide.
In one embodiment the lysis buffer of the invention is used for releasing at least one biomarker from cells in a urine sample. Optionally the at least one biomarker is an Mcm protein, preferably Mcm5.

The lysis buffer may be RIPA buffer.

Performing an Assay to Determine the Concentration of Mcm5

In one embodiment of the invention the term "detecting the presence of Mcm5" can be considered to be substitutable with the term "performing an assay to determine the concentration" of Mcm5. In such embodiments, the presence of Mcm5 can be considered to be detected, where its concentration is higher than a defined cut-off level. For example the cut-off may be a concentration of Mcm5 higher than the mean value from healthy patients plus a multiple of the standard deviation shown by the values derived from healthy subjects.

There is no particular requirement that the concentration of, for example, the full length Mcm5 polypeptide be scored. Indeed, it is possible that detection may take place by assaying particular fragments of Mcm5 being present which are thus taken to indicate the presence of the overall biomarker polypeptide in the sample. This is especially true if the samples are analysed for example by mass spectrometry. Therefore the invention embraces the detection of fragments of Mcm5 biomarkers. Suitably the fragment is sufficiently long to enable its unique identification by immunological or mass spectrometry methods. Such a fragment is suitably at least 6 amino acids in length, suitably at least 7 amino acids in length, suitably at least 8 amino acids in length, suitably at least 9 amino acids in length, suitably at least 10 amino acids in length, suitably at least 15 amino acids, suitably at least 25 amino acids, suitably at least 50 amino acids, suitably at least 100 amino acids, or suitably the majority of Mcm5. Suitably a fragment comprises a small fragment of Mcm5, whilst being long enough to retain an identifiable amino acid sequence or mass.

Antibodies

The assay to determine the concentration of Mcm5 is performed by exposing the sample to a first monoclonal antibody and/or a second monoclonal antibody. Preferably the assay comprises exposing the sample to both a first monoclonal antibody and a second monoclonal antibody. The kits of the invention comprise a first monoclonal antibody and a second monoclonal antibody.

The term 'antibody' can refer to naturally occurring forms or recombinant antibodies such as single-chain antibodies, chimeric antibodies or humanised antibodies. The terms 'antibody' and 'antibodies' may also be considered to encompass fragments of antibodies that can bind to a target protein, such as an Mcm protein like Mcm5. Such fragments may include Fab'2, F'(ab)$_2$, Fv, single chain antibodies or diabodies. In a preferred embodiment antibodies of the invention are naturally occurring, full length antibodies (rather than fragments). In a preferred embodiment the antibody is a mouse antibody (i.e. originally derived from mouse spleen cells).

In general, antibodies are formed from two heavy chains and two lights chains. Each heavy chain is made up of a heavy chain constant region (CH) and a heavy chain variable region (VH). Similarly each light chain is made up of a light chain constant region (CL) and a light chain variable region (VL). The VH and VL regions comprise complementarity defining regions (CDRs). The CDRs are, primarily, responsible for specific binding to the target protein.

An antibody of the invention may be an antibody of any class, particularly IgG, IgM or IgA. In a preferred embodiment the antibody is an IgG antibody.

The term "monoclonal antibody" is intended to refer to an antibody that is obtained from a population of substantially similar antibodies, i.e. from a population of antibodies that are identical except for a minority of naturally occurring variants. A population of monoclonal antibodies will bind to the same epitope. Monoclonal antibodies can be produced by a variety of techniques well known to the person skilled in the art and including the methods disclosed in "*Monoclonal Antibodies: A manual of techniques*", H Zola (CRC Press, 1988) and in "*Monoclonal Hybridoma Antibodies: Techniques and Application*", SG Hurrell (CRC Press, 1982).

Antibody Target

Preferably the first monoclonal antibody and/or the second monoclonal antibody bind specifically to Mcm5. Preferably the first monoclonal antibody binds to SEQ ID NO: 1. Preferably the second monoclonal antibody binds to SEQ ID NO: 2.

The first monoclonal antibody or the second monoclonal antibody will bind to an epitope (fragment) of Mcm5 (for example SEQ ID NO: 1 or SEQ ID NO: 2). Thus, the term "antibody which binds to Mcm5" refers to an antibody that binds to only a single epitope of Mcm5 such as SEQ ID NO: 1 or SEQ ID NO: 2.

For the purposes of the present invention the term 'binding affinity' refers to the ability of an antibody to bind to its target. For the purposes of the present invention, the term specifically binds' refers to an antibody that binds to a target such as Mcm5 with a binding affinity that is at least 2-fold, 10-fold, 50-fold or 100-fold greater than its binding affinity for binding to another non-target molecule. In an embodiment the non-target molecule is an Mcm protein, other than Mcm5, such as Mcm2. Preferably, an antibody of the invention is capable of binding to an Mcm protein, optionally Mcm5, with a binding affinity that is at least 2-fold, 10-fold, 50-fold or 100-fold greater than its binding affinity for binding to another non-target molecule. Even more preferably, an antibody of the invention is capable of binding to SEQ ID NO: 1 (such as the first monoclonal antibody) or SEQ ID NO: 2 (such as the second monoclonal antibody) with a binding affinity that is at least 2-fold, 10-fold, 50-fold or 100-fold greater than its binding affinity for binding to another non-target molecule.

A preferred method for the evaluation of binding affinity for Mcm5 is by ELISA. Preferably, the first monoclonal antibody and/or the second monoclonal antibody have an affinity for Mcm5 (measured as an EC50 or 50% maximum binding concentration, as described in Example 2) of 2500 ng/ml or lower, 1500 ng/ml or lower, 1000 ng/ml or lower, 600 ng/ml or lower, 50 ng/ml or lower, 30 ng/ml or lower, 20 ng/ml or lower, or 10 ng/ml or lower. The EC50 will typically be higher than 1 ng/ml and thus the EC50 may be between 1 ng/ml and any of the upper limits specified in the preceding sentence. Other standard assays to evaluate the binding ability of ligands such as antibodies towards targets are known in the art, including for example, Western blots, RIAs, and flow cytometry analysis. The binding kinetics (e.g. binding affinity) of the antibody also can be assessed by standard assays known in the art, such as by Surface Plasmon Resonance (SPR) (e.g. Biacore system) analysis. The affinity constant (KD) for binding to Mcm5 is preferably in the range of 1-10 000 nM, 1-1 000 nM, 1-500 nM, 1-100 nM, 1-50 nM or 1-10 nM. The association rate (ka) is preferably in the range of $0.4$-$3.4 \times 10^6$ 1/M. The dissociation rate (kd) is preferably in the range of $1$-$10 \times 10^{-3}$ 1/s. These values may typically be determined by SPR (surface plasmon resonance).

Complementary Determining Regions (CDRs)

The invention relates to antibodies that preferably comprise at least one of the CDRs of antibodies 12A7 or 4B4, i.e. a CDR selected from the group consisting of:

a. 12A7 CDRH1 which has a sequence of SEQ ID NO: 9 or a sequence that differs from SEQ ID NO: 9 by 1, 2 or 3 amino acid substitutions;
b. 12A7 CDRH2 which has a sequence of SEQ ID NO: 11 or a sequence that differs from SEQ ID NO: 11 by 1, 2 or 3 amino acid substitutions;
c. 12A7 CDRH3 which has a sequence of SEQ ID NO: 13 or a sequence that differs from SEQ ID NO: 13 by 1, 2 or 3 amino acid substitutions;
d. 12A7 CDRL1 which has a sequence of SEQ ID NO: 3 or a sequence that differs from SEQ ID NO: 3 by 1, 2 or 3 amino acid substitutions;
e. 12A7 CDRL2 which has a sequence of SEQ ID NO: 5 or a sequence that differs from SEQ ID NO: 5 by 1, 2 or 3 amino acid substitutions;
f. 12A7 CDRL3 which has a sequence of SEQ ID NO: 7 or a sequence that differs from SEQ ID NO: 7 by 1, 2 or 3 amino acid substitutions;
g. 4B4 CDRH1 which has a sequence of SEQ ID NO: 21 or a sequence that differs from SEQ ID NO: 21 by 1, 2 or 3 amino acid substitutions;
h. 4B4 CDRH2 which has a sequence of SEQ ID NO: 23 or a sequence that differs from SEQ ID NO: 23 by 1, 2 or 3 amino acid substitutions;
i. 4B4 CDRH3 which has a sequence of SEQ ID NO: 25 or a sequence that differs from SEQ ID NO: 25 by 1, 2 or 3 amino acid substitutions
j. 4B4 CDRL1 which has a sequence of SEQ ID NO: 15 or a sequence that differs from SEQ ID NO: 15 by 1, 2 or 3 amino acid substitutions;
k. 4B4 CDRL2 which has a sequence of SEQ ID NO: 17 or a sequence that differs from SEQ ID NO: 17 by 1, 2 or 3 amino acid substitutions; and
l. 4B4 CDRL3 which has a sequence of SEQ ID NO: 19 or a sequence that differs from SEQ ID NO: 19 by 1, 2 or 3 amino acid substitutions.

Antibodies that have the same CDRs as the 4B4 and 12A7 antibodies may differ substantially from the sequences of 4B4 and 12A7 in other regions. Such antibodies may, for example, be antibody fragments.

The phrase "sequence that differs from SEQ ID NO: 3 by a single amino acid substitution" refers to the possibility of replacing one amino acid defined in SEQ ID NO: 3 by a different amino acid. Preferably such a replacement is a conservative amino acid substitution. The following eight groups each contain amino acids that are typically conservative substitutions for one another:

1) Alanine, Glycine;
2) Aspartic acid, Glutamic acid;
3) Asparagine, Glutamine;
4) Arginine, Lysine;
5) Isoleucine, Leucine, Methionine, Valine;
6) Phenylalanine, Tyrosine, Tryptophan;
7) Serine, Threonine; and
8) Cysteine, Methionine.

In an embodiment the first monoclonal antibody comprises at least one CDR from the heavy chain of 12A7 (12A7 CDRH1, 12A7 CDRH2 or 12A7 CDRH3) as well as at least one CDR from the light chain of 12A7 (12A7 CDRL1, 12A7 CDRL2 or 12A7 CDRL3). In a further embodiment the first monoclonal antibody comprises at least two CDRs from the heavy chain of 12A7 and at least two CDRs from the light chain of 12A7. In a preferred embodiment the first monoclonal antibody comprises all three CDRs from the heavy chain of 12A7 and/or all three CDRs from the light chain of 12A7. In an embodiment the first monoclonal antibody comprises 12A7 CDRL1 and 12A7 CDRL2, 12A7 CDRL1 and 12A7 CDRL3, 12A7 CDRL1 and 12A7 CDRH1, 12A7 CDRL1 and 12A7 CDRH2, 12A7 CDRL1 and 12A7 CDRH3, 12A7 CDRL2 and 12A7 CDRL3, 12A7 CDRL2 and 12A7 CDRH1, 12A7 CDRL2 and 12A7 CDRH2, 12A7 CDRL2 and 12A7 CDRH3, 12A7 CDRL3 and 12A7 CDRH1, 12A7 CDRL3 and 12A7 CDRH2, 12A7 CDRL3 and 12A7 CDRH3, 12A7 CDRH1 and 12A7 CDRH2, 12A7 CDRH1 and 12A7 CDRH3, or 12A7 CDRH2 and 12A7 CDRH3.

In an embodiment the second monoclonal antibody comprises at least one CDR from the heavy chain of 4B4 (4B4 CDRH1, 4B4 CDRH2 or 4B4 CDRH3) as well as at least one CDR from the light chain of 4B4 (4B4 CDRL1, 4B4 CDRL2 or 4B4 CDRL3). In a further embodiment the second monoclonal antibody comprises at least two CDRs from the heavy chain of 4B4 and at least two CDRs from the light chain of 4B4. In a preferred embodiment the second monoclonal antibody comprises all three CDRs from the heavy chain of 4B4 and/or all three CDRs from the light chain of 4B4. In an embodiment the second monoclonal antibody comprises 4B4 CDRL1 and 4B4 CDRL2, 4B4 CDRL1 and 4B4 CDRL3, 4B4 CDRL1 and 4B4 CDRH1, 4B4 CDRL1 and 4B4 CDRH2, 4B4 CDRL1 and 4B4 CDRH3, 4B4 CDRL2 and 4B4 CDRL3, 4B4 CDRL2 and 4B4 CDRH1, 4B4 CDRL2 and 4B4 CDRH2, 4B4 CDRL2 and 4B4 CDRH3, 4B4 CDRL3 and 4B4 CDRH1, 4B4 CDRL3 and 4B4 CDRH2, 4B4 CDRL3 and 4B4 CDRH3, 4B4 CDRH1 and 4B4 CDRH2, 4B4 CDRH1 and 4B4 CDRH3, or 4B4 CDRH2 and 4B4 CDRH3.

In a preferred embodiment an antibody comprises at least one CDR having a sequence identical to that described in any one of SEQ ID NO: 3 (12A7 CDRL1), SEQ ID NO:5 (12A7 CDRL2), SEQ ID NO: 7 (12A7 CDRL3), SEQ ID NO: 9 (12A7 CDRH1), SEQ ID NO: 11 (12A7 CDRH2), SEQ ID NO: 13 (12A7 CDR H3), SEQ ID NO: 15 (4B4 CDRL1), SEQ ID NO: 17 (4B4 CDRL2), SEQ ID NO: 19 (4B4 CDRL3), SEQ ID NO: 21 (4B4 CDRH1), SEQ ID NO: 23 (4B4 CDRH2) or SEQ ID NO:25 (4B4 CDRH3). In an embodiment where the first monoclonal antibody comprises 12A7 CDRL2, the 12A7 CDRL2 has the sequence described in SEQ ID NO: 5. In a further embodiment where the first monoclonal antibody comprises 12A7 CDRL1, the 12A7 CDRL1 has the sequence described in SEQ ID NO: 3. In a further embodiment where the first monoclonal antibody comprises 12A7 CDRL3, the 12A7 CDRL3 has the sequence described in SEQ ID NO: 7. In a further embodiment where the first monoclonal antibody comprises 12A7 CDRH1, the 12A7 CDRH1 has the sequence described in SEQ ID NO: 9. In a further embodiment where the first monoclonal antibody comprises 12A7 CDRH2, the 12A7 CDRH2 has the sequence described in SEQ ID NO: 11. In a further embodiment where the first monoclonal antibody comprises 12A7 CDRH3, the 12A7 CDRH3 has the sequence described in SEQ ID NO: 13. In a further embodiment where the second monoclonal antibody comprises 4B4 CDRL1, the 4B4 CDRL1 has the sequence described in SEQ ID NO: 15. In a further embodiment where the second monoclonal antibody comprises 4B4 CDRL2, the 4B4 CDRL2 has the sequence described in SEQ ID NO: 17. In a further embodiment where the second monoclonal antibody comprises 4B4 CDRL3, the 4B4 CDRL3 has the sequence described in SEQ ID NO: 19. In a further embodiment where the second monoclonal antibody comprises 4B4 CDRH1, the 4B4 CDRH1 has the sequence described in SEQ ID NO: 21. In a further embodiment where the second monoclonal antibody comprises 4B4 CDRH2, the 4B4 CDRH2 has the sequence described in SEQ ID NO: 23. In a further embodiment where the second monoclonal antibody comprises 4B4 CDRH3, the 4B4 CDRH3 has the sequence described in SEQ ID NO: 25.

Preferably an antibody comprising at least one of the CDRs of 12A7 or 4B4 binds (optionally specifically binds) to Mcm5. Even more preferably an antibody comprising at least one of the CDRs of 12A7 or 4B4 binds (optionally specifically binds) to SEQ ID NO: 1 or SEQ ID NO: 2.

Heavy and Light Chain Variable Region Sequences

The first monoclonal antibody preferably comprises a heavy chain variable region having a sequence at least 85%, 90%, 95%, 98%, 99% or 100% identical to SEQ ID NO: 29. The first monoclonal antibody preferably comprises a light chain variable region sequence having a sequence at least 85%, 90%, 95%, 98%, 99% or 100% identical to SEQ ID NO: 27. The second monoclonal antibody preferably comprises a heavy chain variable region having a sequence at least 85%, 90%, 95%, 98%, 99% or 100% identical to SEQ ID NO: 33. The second monoclonal antibody preferably comprises a light chain variable region sequence having a sequence at least 85%, 90%, 95%, 98%, 99% or 100% identical to SEQ ID NO: 31. Such antibodies may be referred to as "variant antibodies".

In an embodiment the first monoclonal antibody comprises a heavy chain variable region having a sequence at least 95% identical to SEQ ID NO: 29. In a further embodiment the first monoclonal antibody comprises a heavy chain variable region having a sequence at least 98% identical to SEQ ID NO: 29. In one embodiment the first monoclonal antibody comprises a light chain variable region having a sequence at least 95% identical to SEQ ID NO: 27. In a further embodiment the first monoclonal antibody comprises a light chain variable region having a sequence at least 98% identical to SEQ ID NO: 27. In a further embodiment the first monoclonal antibody comprises a light chain variable region having a sequence at least 95% identical to SEQ ID NO: 27 and a heavy chain variable region having a sequence at least 95% identical to SEQ ID NO: 29. In a preferred embodiment the first monoclonal antibody comprises a heavy chain variable region having a sequence at least 98% identical to SEQ ID NO: 29 and a light chain variable region having a sequence at least 98% identical to SEQ ID NO: 27.

In a further embodiment the second monoclonal antibody comprises a heavy chain variable region having a sequence at least 95% identical to SEQ ID NO: 33. In a further embodiment the second monoclonal antibody comprises a heavy chain variable region having a sequence at least 98% identical to SEQ ID NO: 33. In a further embodiment the second monoclonal antibody comprises a light chain variable region having a sequence at least 95% identical to SEQ ID NO: 31. In a further embodiment the second monoclonal antibody comprises a light chain variable region having a sequence at least 98% identical to SEQ ID NO: 31. In a further embodiment the second monoclonal antibody has a heavy chain variable region having a sequence at least 95% identical to SEQ ID NO:33 and a light chain variable region having a sequence at least 95% identical to SEQ ID NO: 31. In a preferred embodiment the second monoclonal antibody has a heavy chain variable region having a sequence at least 98% identical to SEQ ID NO: 33 and a light chain variable region having a sequence at least 98% identical to SEQ ID NO: 31.

As is known to the person skilled in the art, antibodies contain multiple regions including framework regions. Deletion or addition of amino acids in the framework regions is unlikely to affect the ability of the antibody to bind to its target. On the other hand, mutations in the CDRs are considerably more likely to affect the ability of an antibody to bind to a target. Thus, in certain embodiments of the invention, variant antibodies have CDRs which are identical to the CDRs of the 12A7 or 4B4 antibodies or have CDRs which vary in only a single amino acid substitution (preferably a conservative amino acid substitution). The first monoclonal antibody and/or the second monoclonal antibody may have framework regions which differ in sequence quite significantly from those described in SEQ ID NO: 27, 29, 31 or 33.

Optionally, where the first monoclonal antibody comprises a heavy chain variable region having a sequence at least 85%, 90%, 95%, 98%, 99% or 100% identical to SEQ ID NO: 29, the antibody further comprises at least one of 12A7 CDRH1, 12A7 CDRH2 or 12A7 CDRH3. It is understood by the person skilled in the art that, since target binding specificity is determined by the CDRs, an antibody comprising the CDRs of 12A7 may still bind to Mcm5 even if the remainder of the antibody sequence is quite variable. For this reason where the first monoclonal antibody comprises at least one of 12A7 CDRH1, 12A7 CDRH2 or 12A7 CDRH3 the first monoclonal antibody preferably comprises a heavy chain variable region having a sequence at least 90% identical to SEQ ID NO: 29.

In a more preferred embodiment the first monoclonal antibody of the invention comprises 12A7 CDRH1, 12A7 CDRH2 and 12A7 CDRH3 and comprises a heavy chain variable region having a sequence at least 95% identical to SEQ ID NO:29.

Optionally, where the second monoclonal antibody comprises a heavy chain variable region having a sequence at least 85%, 90%, 95%, 98%, 99% or 100% identical to SEQ ID NO: 33, the second monoclonal antibody further comprises at least one of 4B4 CDRH1, 4B4 CDRH2 or 4B4 CDRH3. It is understood by the person skilled in the art that, since target binding specificity is determined by the CDRs, an antibody comprising the CDRs of 4B4 may still bind to Mcm5 even if the remainder of the antibody sequence is quite variable. For this reason where the second monoclonal antibody comprises at least one of 4B4 CDRH1, 4B4 CDRH2 or 4B4 CDRH3 the second monoclonal antibody preferably comprises a heavy chain variable region having a sequence at least 90% identical to SEQ ID NO: 33. In a more preferred embodiment the second monoclonal antibody comprises 4B4 CDRH1, 4B4 CDRH2 and 4B4 CDRH3 and comprises a heavy chain variable region having a sequence at least 95% identical to SEQ ID NO: 33.

Optionally, where the first monoclonal antibody comprises a light chain variable region having a sequence at least 85%, 90%, 95%, 98%, 99% or 100% identical to SEQ ID NO: 27, the first monoclonal antibody further comprises at least one of 12A7 CDRL1, 12A7 CDRL2 or 12A7 CDRL3. It is understood by the person skilled in the art that, since target binding specificity is determined by the CDRs, an antibody comprising the CDRs of 12A7 may still bind to Mcm5 even if the remainder of the antibody sequence is quite variable. For this reason where the first monoclonal antibody comprises at least one of 12A7 CDRL1, 12A7 CDRL2 or 12A7 CDRL3 the first monoclonal antibody preferably comprises a light chain variable region having a sequence at least 90% identical to SEQ ID NO: 27. In a more preferred embodiment the first monoclonal antibody comprises 12A7 CDRL1, 12A7 CDRL2 and 12A7 CDRL3 and comprises a light chain variable region having a sequence at least 95% identical to SEQ ID NO: 27.

Optionally, where the second monoclonal antibody of the invention comprises a light chain variable region having a sequence at least 85%, 90%, 95%, 98%, 99% or 100% identical to SEQ ID NO: 31, the second monoclonal antibody further comprises at least one of 4B4 CDRL1, 4B4 CDRL2 or 4B4 CDRL3. It is understood by the person skilled in the art that, since target binding specificity is determined by the CDRs, an antibody comprising the CDRs of 4B4 may still bind to Mcm5 even if the remainder of the antibody sequence is quite variable. For this reason where the second monoclonal antibody comprises at least one of 4B4 CDRL1, 4B4 CDRL2 or 4B4 CDRL3 the second monoclonal antibody preferably comprises a heavy chain variable region having a sequence at least 90% identical to SEQ ID NO: 31. In a more preferred embodiment the second monoclonal antibody comprises 4B4 CDRL1, 4B4 CDRL2 and 4B4 CDRL3 and comprises a heavy chain variable region having a sequence at least 95% identical to SEQ ID NO:31.

In a further embodiment of the invention the first monoclonal antibody comprises:
(i) 12A7 CDRH1, 12A7 CDRH2 and 12A7 CDRH3;
(ii) a heavy chain variable region having a sequence at least 95% identical to SEQ ID NO: 29;
(iii) 12A7 CDRL1, 12A7 CDRL2 and 12A7 CDRL3; and
(iv) a light chain variable region having a sequence at least 95% identical to SEQ ID NO: 27.

In a further embodiment the second monoclonal antibody comprises:
(i) 4B4 CDRH1, 4B4 CDRH2 and 4B4 CDRH3;
(ii) a heavy chain variable region having a sequence at least 95% identical to SEQ ID NO: 33;
(iii) 4B4 CDRL1, 4B4 CDRL2 and 4B4 CDRL3; and
(iv) a heavy chain variable region having a sequence at least 95% identical to SEQ ID NO: 31.

An antibody having a heavy chain variable sequence identical to SEQ ID NO: 29 and a light chain variable sequence identical to SEQ ID NO: 27 may be referred to as antibody 12A7. An antibody having a heavy chain variable sequence identical to SEQ ID NO: 33 and a light chain variable sequence identical to SEQ ID NO: 31 may be referred to as an antibody 4B4.

In some embodiments the first monoclonal antibody will compete for binding to Mcm5 with the 12A7 antibody. Similarly, in some embodiments of the invention the second monoclonal antibody will compete for binding to Mcm5 with the 4B4 antibody.

For the purposes of the present invention an antibody is ' at least 90%, 95%, 98%, 99% or 100% identical' to a second antibody if the sequences have at least 90%, 95%, 98%, 99% or 100% identity when assessed using ClustalW (Thompson et al., 1994) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR.

It is well within the knowledge of the person skilled in the art how to make variant antibodies which bind to Mcm5. Such variant antibodies may comprise 1, 2, 3, 4, 5, 6, 7, 8, 9, 10, 15, 20, 25, 50 or 100 substitution or deletion mutations compared to SEQ ID NOs: 27, 29, 31 or 33. 'Deletion' variant antibodies may comprise the deletion of 1, 2, 3, 4, 5 or more amino acids or, in some cases, the deletion of entire regions of SEQ ID NOs: 27, 29, 31 or 33. 'Substitution' variants may comprise the replacement of 1, 2, 3, 4, 5 or more amino acids with the same number of new amino acids.

Preferably, the variant antibodies of the invention comprise sequences differing from SEQ ID NOs: 27, 29, 31 or 33 by conservative amino acid substitutions (optionally only by conservative amino acid substitutions). The skilled person is well aware that such conservative substitutions are unlikely to alter the binding properties of an antibody.

Antibodies that Compete with Antibodies of the Invention

The invention further relates to a first monoclonal antibody that competes with an antibody which:
(i) binds to a polypeptide having an amino acid sequence of SEQ ID NO: 1;

(ii) comprises at least one Complementary Determining Region (CDR) selected from the group consisting of:
    (a) 12A7 CDRH1 which has a sequence of SEQ ID NO: 9 or a sequence that differs from SEQ ID NO:9 by a single amino acid substitution;
    (b) 12A7 CDRH2 which has a sequence of SEQ ID NO: 11 or a sequence that differs from SEQ ID NO:11 by a single amino acid substitution;
    (c) 12A7 CDRH3 which has a sequence of SEQ ID NO: 13 or a sequence that differs from SEQ ID NO:13 by a single amino acid substitution;
    (d) 12A7 CDRL1 which has a sequence of SEQ ID NO: 3 or a sequence that differs from SEQ ID NO:3 by a single amino acid substitution;
    (e) 12A7 CDRL2 which has a sequence of SEQ ID NO: 5 or a sequence that differs from SEQ ID NO:5 by a single amino acid substitution; and
    (f) 12A7 CDRL3 which has a sequence of SEQ ID NO: 7 or a sequence that differs from SEQ ID NO:7 by a single amino acid substitution;
(iii) comprises a heavy chain variable region having a sequence at least 85%, 90%, 95%, 98%, 99% or 100% identical to SEQ ID NO: 29; or
(iv) comprises a light chain variable region sequence having a sequence at least 85%, 90%, 95%, 98%, 99% or 100% identical to SEQ ID NO: 27.

The invention further relates to a second monoclonal antibody that competes with an antibody which:
(i) binds to a polypeptide having an amino acid sequence of SEQ ID NO: 2;
(ii) comprises at least one Complementary Determining Region (CDR) selected from the group consisting of:
    (a) 4B4 CDRH1 which has a sequence of SEQ ID NO: 21 or a sequence that differs from SEQ ID NO:21 by a single amino acid substitution;
    (b) 4B4 CDRH2 which has a sequence of SEQ ID NO: 23 or a sequence that differs from SEQ ID NO:23 by a single amino acid substitution; and
    (c) 4B4 CDRH3 which has a sequence of SEQ ID NO: 25 or a sequence that differs from SEQ ID NO:25 by a single amino acid substitution;
    (d) 4B4 CDRL1 which has a sequence of SEQ ID NO: 15 or a sequence that differs from SEQ ID NO:15 by a single amino acid substitution;
    (e) 4B4 CDRL2 which has a sequence of SEQ ID NO: 17 or a sequence that differs from SEQ ID NO:17 by a single amino acid substitution; and
    (f) 4B4 CDRL3 which has a sequence of SEQ ID NO: 19 or a sequence that differs from SEQ ID NO:19 by a single amino acid substitution;
(iii) comprises a heavy chain variable region having a sequence at least 85%, 90%, 95%, 98%, 99% or 100% identical to SEQ ID NO: 33; or
(iv) comprises a light chain variable region sequence having a sequence at least 85%, 90%, 95%, 98%, 99% or 100% identical to SEQ ID NO: 31.

Preferably the first monoclonal antibody is an antibody that competes with an antibody comprising 12A7 CDRH1, 12A7 CDRH2, 12A7 CDRH3, 12A7 CDRL1, 12A7 CDRL2, and 12A7 CDRL3. Preferably the second monoclonal antibody is an antibody that competes with an antibody comprising 4B4 CDRH1, 4B4 CDRH2, 4B4 CDRH3, 4B4 CDRL1, 4B4 CDRL2, and 4B4 CDRL3. More preferably the first monoclonal antibody is an antibody that competes with an antibody comprising a heavy chain variable region having a sequence identical to SEQ ID NO: 29 and a light chain variable region having a sequence identical to SEQ ID NO: 27. More preferably the second monoclonal antibody is an antibody that competes with an antibody comprising a heavy chain variable region having a sequence identical to SEQ ID NO: 33 and a light chain variable region having a sequence identical to SEQ ID NO: 31.

It is within the abilities of the person skilled in the art, to determine whether an antibody competes with another antibody of the invention.

For example, an ELISA assay may be performed by immobilising the reference antibody, such as a 4B4 or a 12A7 antibody, on an ELISA plate. The plate is then blocked with a suitable blocking agent. An excess of a second antibody is added (the second antibody is the antibody whose ability to compete with the 4B4 or 12A7 antibody is to be assessed for example a first monoclonal antibody or a second monoclonal antibody that competes with 4B4 or 12A7). Mcm5 is added. Following a suitable incubation period, the ELISA plate is washed and an Mcm5 detection agent is added to measure the amount of Mcm5 bound to the immobilised reference antibody. If this test is to be used to detect whether an antibody competes with 4B4, a suitable detection reagent is a labelled 12A7 antibody. Similarly if this test is to be used to detect whether an antibody competes with 12A7, a suitable detection reagent is a labelled 4B4 antibody. The concentration at which 50% inhibition occurs is known as the Ki. In a preferred embodiment an antibody that competes with 12A7 or 4B4 binds with a Ki 2-fold, 5-fold, 10-fold, 50-fold or 100-fold lower than an antibody which does not bind to Mcm5.

In an embodiment an antibody that competes with a particular antibody binds to the same epitope as that particular antibody (for example SEQ ID NO: 1 or SEQ ID NO: 2). It is possible to determine to which epitope an antibody binds by performing an experiment in which the target protein, such as Mcm5, is digested into fragments (for example see Example 3 below). The affinity with which the 12A7 and 4B4 antibodies to bind to each of the fragments can then be determined. Once the fragment (representing the epitope), to which the first antibody binds with a reasonable affinity, has been determined, the epitope may be synthesised. It is then possible to determine whether a second antibody is capable of binding to the same epitope by measuring the binding affinity of that second antibody to the fragment.

Antibody Production

The first monoclonal antibody or the second monoclonal antibody may be produced from a polynucleotide which encodes, and is capable of expressing, it. Where the antibody comprises two or more chains, a polynucleotide of the invention may encode an antibody light chain, and an antibody heavy chain or both. Two polynucleotides may be provided, one of which encodes an antibody light chain and the other of which encodes the corresponding antibody heavy chain. Such a polynucleotide or pair of polynucleotides may be expressed together such that an antibody of the invention is generated. The polynucleotide may be part of a vector which typically further comprises control sequences operably linked to the inserted sequence, thus allowing for expression of the antibody of the invention in vivo. Preferably the vector of the invention further comprises appropriate initiators, promoters, enhances and other elements which may be necessary and which are positioned in the correct orientation, in order to allow for expression of a polypeptide of the invention.

Polynucleotides can be synthesised according to methods well known in the art, as described by way of example in Sambrook et al (1989, Molecular Cloning—a laboratory manual; Cold Spring Harbor Press).

The polynucleotides or vectors may be expressed in a host cell. Such host cells may be eukaryotic cells or prokaryotic cells. For example, the host cells may be mammalian cells, insect cells, or bacterial cells. Particular examples of host cells that may be modified by insertion of vectors or nucleic acids of the invention include mammalian HEK293T, CHO, HeLa, NSO and COS cells. Alternatively bacterial cells such as E. coli may be used.

Such host cells may be cultured using routine methods to produce an antibody of the invention.

The first monoclonal antibody or the second monoclonal antibody may also be produced from a hybridoma. It is well within the ability of the person skilled in the art to develop a hybridoma expressing an antibody of the invention. This may be performed by immunising a mammal such as a mouse, rabbit or guinea pig, with an antigen (for example Mcm5). It may be beneficial to include an adjuvant such as Freund's complete adjuvant. The spleen cells of the immunised mammal removed and fused with myeloma cells to form hybridoma lines which are immortal given appropriate conditions and which secrete antibodies. The hybridomas are separated into single clones and the antibodies secreted by each clone are evaluated for their binding ability to Mcm5 protein.

The first monoclonal antibody or the second monoclonal antibody may be produced using any method. In one embodiment, the antibodies are produced directly from a hybridoma cell line. In a further embodiment of the invention, the antibodies are produced recombinantly.

To produce an antibody from a hybridoma cell line, the cell line can be cultivated in vitro, for example in a vessel such as a cell culture flask or a fermenter, and the antibody can be isolated from the vessel using conventional techniques known in the art. For the purposes of the present invention, an antibody will be considered to have been "produced by a hybridoma cell line" if the antibody is derived from an antibody which was produced by the hybridoma cell line. For example, it is well within the abilities of the person skilled in the art to obtain an antibody from a hybridoma cell line, sequence the amino acid sequence of the antibody, and transfect cells such as CHO cells or E. coli cells with vectors encoding the amino acid sequence of the antibody. Such antibodies can be considered to have been "derived" from an antibody which was produced by the hybridoma cell line. In one particular embodiment, antibodies of the invention are produced directly from the hybridoma cell line itself.

Alternatively antibodies of the invention may be produced using recombinant techniques. The sequence of an antibody of the invention may be used to transfect a host cell line of the invention. The cell lines may be grown in a flask or a fermenter, and the antibody expressed by the cell can be isolated and purified using standard techniques (such as affinity chromatography).

Once purified the antibodies may then be conjugated to a radio label or immobilised to a solid support. An example of a suitable solid support is an ELISA plate.

Exposing the Sample to the First Monoclonal Antibody and/or the Second Monoclonal Antibody and Measuring the Amount of Mcm5 that Binds to the First Monoclonal Antibody and/or the Second Monoclonal Antibody The method of the invention comprises exposing the sample to the first monoclonal antibody and/or the second monoclonal antibody and measuring the amount of Mcm5 that binds to the first monoclonal antibody and/or the second monoclonal antibody. Preferably this step is carried out using an assay such as a sandwich assay. Preferably this step is carried out using an ELISA assay. Even more preferably this step is carried out using a sandwich ELISA assay. Preferably this step does not comprise an immunofluorometric assay.

For example, this step may comprise steps of capturing the Mcm5 using a "capture antibody" already bound to the plate, and detecting how much antigen has been captured using a "detection antibody". The detection antibody has been pre-conjugated to a label such as the enzyme HRP (Horse Radish Peroxidase). The ELISA plate with the labelled detection antibody is then washed to remove any excess unbound detection antibody. The washed plate is then exposed to an agent whose properties are changed by the label in a measurable manner. The concentration of the detection antibody may then be determined. For example if the detection antibody is conjugated to (labelled with) horseradish peroxidase, the ELISA plate may be exposed to TMB substrate. The concentration of the detection antibody, and therefore the concentration of Mcm5 in the original sample, may then be determined by quantitation of the colour change corresponding to the conversion of TMB into a coloured product. In such an assay the first monoclonal antibody may be the capture antibody and the second monoclonal antibody may be the detection antibody. Alternatively the first monoclonal antibody may be the detection antibody and the second monoclonal antibody may be the capture antibody.

Detection Antibodies

The method of the invention may comprise exposing Mcm5 to a detection antibody. In addition, in kits of the invention, the first monoclonal antibody or the second monoclonal antibody may be a detection antibody. The detection antibody may be conjugated to any suitable label (for example Europium$^{3+}$ or Horseradish Peroxidase). The label may be directly, attached or may be attached via a linker (such as Adipic Acid Dihydrazide (ADH)).

The label may be attached by chemical conjugation. Methods of conjugating labels to antibodies are known in the art. For example, carbodiimide conjugation (Bauminger & Wilchek (1980) Methods Enzymol. 70, 151-159) may be used to conjugate labels to antibodies. Other methods for conjugating a label to an antibody can also be used. For example, sodium periodate oxidation followed by reductive alkylation of appropriate reactants can be used, as can glutaraldehyde cross-linking. However, it is recognised that, regardless of which method of producing a conjugate of the invention is selected, a determination must be made that the conjugated detection antibody maintains its targeting ability and that the conjugated label maintains its function.

In a preferred embodiment the detection antibody is labelled by conjugation to Horseradish Peroxidase.

Kits

The present invention provides a kit comprising a lysis buffer which is capable of releasing Mcm5 from cells in a urine sample, a first monoclonal antibody and a second monoclonal antibody wherein the first monoclonal antibody is an antibody which:
(i) binds to a polypeptide having an amino acid sequence of SEQ ID NO: 1;
(ii) comprises at least one Complementary Determining Region (CDR) selected from the group consisting of:
(a) 12A7 CDRH1 which has a sequence of SEQ ID NO: 9 or a sequence that differs from SEQ ID NO:9 by a single amino acid substitution;

(b) 12A7 CDRH2 which has a sequence of SEQ ID NO: 11 or a sequence that differs from SEQ ID NO:11 by a single amino acid substitution;
(c) 12A7 CDRH3 which has a sequence of SEQ ID NO: 13 or a sequence that differs from SEQ ID NO:13 by a single amino acid substitution;
(d) 12A7 CDRL1 which has a sequence of SEQ ID NO: 3 or a sequence that differs from SEQ ID NO:3 by a single amino acid substitution;
(e) 12A7 CDRL2 which has a sequence of SEQ ID NO: 5 or a sequence that differs from SEQ ID NO:5 by a single amino acid substitution; and
(f) 12A7 CDRL3 which has a sequence of SEQ ID NO: 7 or a sequence that differs from SEQ ID NO:7 by a single amino acid substitution;

(iii) comprises a heavy chain variable region having a sequence at least 85%, 90%, 95%, 98%, 99% or 100% identical to SEQ ID NO: 29;
(iv) comprises a light chain variable region sequence having a sequence at least 85%, 90%, 95%, 98%, 99% or 100% identical to SEQ ID NO: 27; or
(v) competes with the antibody of (i), (ii), (iii) or (iv);

and the second monoclonal antibody is an antibody which:
(i) binds to a polypeptide having an amino acid sequence of SEQ ID NO: 2;
(ii) comprises at least one Complementary Determining Region (CDR) selected from the group consisting of:
(a) 4B4 CDRH1 which has a sequence of SEQ ID NO: 21 or a sequence that differs from SEQ ID NO:21 by a single amino acid substitution;
(b) 4B4 CDRH2 which has a sequence of SEQ ID NO: 23 or a sequence that differs from SEQ ID NO:23 by a single amino acid substitution; and
(c) 4B4 CDRH3 which has a sequence of SEQ ID NO: 25 or a sequence that differs from SEQ ID NO:25 by a single amino acid substitution;
(d) 4B4 CDRL1 which has a sequence of SEQ ID NO: 15 or a sequence that differs from SEQ ID NO:15 by a single amino acid substitution;
(e) 4B4 CDRL2 which has a sequence of SEQ ID NO: 17 or a sequence that differs from SEQ ID NO:17 by a single amino acid substitution; and
(f) 4B4 CDRL3 which has a sequence of SEQ ID NO: 19 or a sequence that differs from SEQ ID NO:19 by a single amino acid substitution;

(iii) comprises a heavy chain variable region having a sequence at least 85%, 90%, 95%, 98%, 99% or 100% identical to SEQ ID NO: 33;
(iv) comprises a light chain variable region sequence having a sequence at least 85%, 90%, 95%, 98%, 99% or 100% identical to SEQ ID NO: 31; or
(v) competes with the antibody of (i), (ii), (iii) or (iv).

Suitably a kit of the invention is suitable for performing the method of the invention.

In some embodiments the first monoclonal antibody and/or the second monoclonal antibody are present in the kit as part of a composition. In some embodiments the kit comprises a vial or other suitable container containing a composition comprising the first monoclonal antibody (which is optionally conjugated to a label) and optionally comprising further components. In some embodiments the kit comprises a vial or other suitable container containing a composition comprising the first second monoclonal antibody (which is optionally conjugated to a label) and optionally comprising further components.

Such compositions may further comprise suitable stabilising agents that are capable of stabilising the antibody in solution. For example, the composition may comprise a buffer selected from the group consisting of TAPS (3-{[tris(hydroxymethyl)methyl]amino}propanesulphonic acid), Bicine (N,N-bis(2-hydroxyethyl)glycine), Tris (tris(hydroxymethyl)methylamine), Tricine (N-tris(hydroxymethyl(methylglycine), TAPSO (3-[N-Tris(hydroxymethyl)methylamino]-2-hydroxypropanesulphonic acid), HEPES (4-2-hydroxyethyl-1-piperazineethanesulphonic acid), phosphate buffer saline and MOPS (3-(N-morpholino)propanesulphonic acid. In a preferred embodiment the composition comprises phosphate-buffered saline pH 7.6. In a further preferred embodiment the composition comprises phosphate-buffered saline with between 0.01% and 0.09% sodium azide. Preferably, the composition comprises agents suitable for storing the antibodies of the invention at room temperature or at a temperature less than or equal to 15° C., 10° C., 7° C., 5° C., 0° C., −10° C., or −25° C. In a preferred embodiment the composition comprises agents suitable for storing the antibodies of the invention at a temperature between 2° C. and 8° C. In a further embodiment, the composition comprises a stabilising agent such as a sugar, for example lactose or trehalose.

In some embodiments the first monoclonal antibody and/or the second monoclonal antibody present in the kit is a "detection antibody". If the antibody of the invention is conjugated, for example to a Europium label, it is advantageous to include a 7.5% purified BSA stabiliser in the composition.

In some embodiments the first monoclonal antibody and/or the second monoclonal antibody is present in the kit bound to a solid support such as an ELISA plate. In such embodiments an antibody bound to a solid support may be referred to as a "capture antibody".

In an embodiment the kit comprises a calibrator. The "calibrator" is a preparation of one or more known concentrations of Mcm5.

In an embodiment the kit comprises a substrate reagent. A substrate reagent can be used to detect the detection antibody. For example, where a "detection antibody" is conjugated to horse radish peroxidase the substrate reagent may comprise TMB (3, 3', 5, 5'-tetramethylbenzidine), DAB (3, 3'-diaminobenzidine) or ABTS (2, 2'-azino-bis (3-ethylbenzothiazoline-6-sulphonic acid). In a preferred embodiment the substrate reagent comprises TMB. In a more preferred embodiment the substrate reagent is peroxide and TMB.

In an embodiment the kit further comprises a wash solution and/or a stop solution. In an embodiment the kit is suitable for performing a sandwich ELISA.

Comparing the concentration of Mcm5 determined in step (b) to reference values

The method of the invention further comprises a step of comparing the concentration of Mcm5 determined to reference values. A kit of the invention may comprise a reference standard. The reference standard typically refers to a sample from a healthy individual i.e. one who has not suffered urological cancer.

The reference standard can be an actual sample analysed in parallel. Alternatively the reference standard can be one or more values previously derived from a comparative sample e.g. a sample from a healthy subject (for a example a subject who is known not to be suffering from a urological cancer). In such embodiments a mere numeric comparison may be made by comparing the value determined for the sample from the subject to the numeric value of a previously analysed reference sample. The advantage of this is not having to duplicate the analysis by determining concentrations in individual reference samples in parallel each time a sample from a subject is analysed.

Suitably the reference standard is matched to the subject being analysed e.g. by gender e.g. by age e.g. by ethnic background or other such criteria which are well known in the art. The reference standard may be a number such as an absolute concentration determined by one or more previous studies.

Reference standards may suitably be matched to specific patient sub-groups e.g. elderly subjects, or those with a previous relevant history such as a predisposition to urological cancer.

Suitably the reference standard is matched to the sample type being analysed. For example the concentration of the biomarker polypeptide(s) being assayed may vary depending on the type or nature of the sample (e.g. conventional urine sample vs first catch sample after prostatic massage). It will be immediately apparent to the skilled worker that the concentration value(s) for the reference standard should be for the same or a comparable sample to that being tested in the method(s) of the invention. For example, if the sample being assayed is first catch urine then the reference standard value should be for first catch urine to ensure that it is capable of meaningful cross-comparison. In particular, extreme care must be taken if inferences are attempted by comparison between concentrations determined for a subject of interest and concentrations determined for reference standards where the nature of the sample is non-identical between the two. Suitably the sample type for the reference standard and the sample type for the subject of interest are the same.

It should be noted that for some embodiments of the invention, the protein concentrations determined may be compared to a previous sample from the same subject. This can be beneficial in monitoring the possibility of recurrence in a subject. This can be beneficial in monitoring the course and/or effectiveness of a treatment of a subject. In this embodiment the method may comprise further step(s) of comparing the value(s) determined for the sample of interest to one or more value(s) determined for the same biomarker(s) from different samples such as samples taken at different time points for the same subject. By making such a comparison, information can be gathered about whether a particular marker is increasing or decreasing in a particular subject. This information may be useful in diagnosing or predicting changes over time, or changes inhibited or stimulated by a particular treatment or therapy regime, or any other variable of interest.

In this way, the invention can be used to determine whether, for example after treatment of the patient with a drug or candidate drug, or by tumour resection, the disease has progressed or not, or that the rate of disease progression has been modified. The result can inform the pathway of further treatment.

In some embodiments an abnormal value (for example a value that is statistically different to the reference value) indicates an increased likelihood of a urological cancer in the subject. Preferably the patient is diagnosed as having a urological cancer where the concentration of the Mcm5 determined in step (b) is higher than the mean value from healthy patients plus a multiple of the standard deviation shown by the values derived from healthy subjects.

Urological Cancers

The invention also provides methods for detecting a urological cancer. Such methods offer a significant advantage in that they will detect any tumours which are in intimate contact with the flow or urine in the urological system (i.e kidneys, ureters, bladder and urethra) of the patient being assayed.

Urological cancer includes all types of transitional cell carcinoma which might arise in the urological system. One example of transitional cell carcinoma is bladder cancer. However, transitional cells are present throughout the urological system including the lining of the renal pelvis, the ureters which conduct urine from the kidneys to the bladder and the urethra, as well as the wall of the bladder itself. Transitional cell carcinoma may arise in any of these locations.

It should be noted that there is a range of different sub-types of bladder cancer, i.e. there are types of bladder cancer other than transitional cell carcinoma, although this (transitional cell carcinoma) is the most common type of bladder cancer.

It is an advantage of the invention that other primary cancers such as penile cancer may also be detected, for example if they impinge on the urethral tract as it passes through the penis.

In addition, certain urological tumours may be detected even though they may not be in direct contact with the urine flow. One example is a prostate tumour which is not typically in contact with the urine flow, but from which cells exfoliate and exude into the urethra.

The invention also offers the advantage of being capable of detecting metastatic cancers, for example metastases of a different primary cancer which metastases have alighted in the urological system. In this embodiment, the invention is capable of detecting any cancer which either grew into the urological system (e.g., a colon cancer which may have invaded locally) or any cancer which has invaded through a metastasis (e.g., a remote primary cancer, which has given rise to one or more metastatic tumours within the urological system of the subject).

In one embodiment, the invention is advantageously applied to the detection of prostate cancer. In one embodiment, the invention is advantageously applied to the detection of bladder cancer. In one embodiment, the invention is applied to the detection of both prostate and bladder cancer.

Sequence Homology/Identity

Although sequence homology can also be considered in terms of functional similarity (i.e., amino acid residues having similar chemical properties/functions), in the context of the present document it is preferred to express homology in terms of sequence identity. Sequence comparisons can be conducted by eye or, more usually, with the aid of readily available sequence comparison programs. These publicly and commercially available computer programs can calculate percent homology (such as percent identity) between two or more sequences.

Percent identity may be calculated over contiguous sequences, i.e., one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues (for example less than 50 contiguous amino acids). For comparison over longer sequences, gap scoring is used to produce an optimal alignment to accurately reflect identity levels in related sequences having insertion(s) or deletion(s) relative to one another. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package, FASTA (Altschul et al., 1990, J. Mol. Biol. 215:403-410) and the GENEWORKS suite of comparison tools.

In the context of the present document, a homologous amino acid sequence is taken to include an amino acid sequence which is at least 40, 50, 60, 70, 80 or 90% identical. Most suitably a polypeptide having at least 90% sequence identity to the biomarker of interest will be taken as indicative of the presence of that biomarker; more suitably a polypeptide which is 95% or more suitably 98% identical at the amino acid level will be taken to indicate presence of that biomarker. Suitably said comparison is made over at least the length of the polypeptide or fragment which is being assayed to determine the presence or absence of the biomarker of interest. Most suitably the comparison is made across the full length of the polypeptide of interest.

Definitions

The terms "comprises" means "includes". Thus, the word "comprises" and variations such as "comprise", and "comprising" will be understood to imply the inclusion of a stated compound or composition or step, or group of compounds or steps, but not to the exclusion of any other compounds, composition, steps or groups thereof.

The term "consists of" should also be understood to have its normal meaning in the art, i.e. that the stated feature or group of features is included, to the exclusion of further features. For example a lysis buffer consisting of a detergent contains detergent and no other components. On the other hand a lysis buffer comprising a detergent consisting of polysorbate 80 may comprise components other than detergents but the only detergent in the lysis buffer is polysorbate 80.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

TABLE 1

Sequences

| SEQ ID NO. | Nucleotide/Polypeptide |
| --- | --- |
| 1 | WDETKGE (epitope to which antibody 12A7 binds) |
| 2 | DDRVAIH (epitope to which antibody 4B4 binds) |
| 3 | 12A7 light chain CDR 1 polypeptide sequence |
| 4 | 12A7 light chain CDR 1 nucleotide sequence |
| 5 | 12A7 light chain CDR 2 polypeptide sequence |
| 6 | 12A7 light chain CDR 2 nucleotide sequence |
| 7 | 12A7 light chain CDR 3 polypeptide sequence |
| 8 | 12A7 light chain CDR 3 nucleotide sequence |
| 9 | 12A7 heavy chain CDR 1 polypeptide sequence |
| 10 | 12A7 heavy chain CDR 1 nucleotide sequence |
| 11 | 12A7 heavy chain CDR 2 polypeptide sequence |
| 12 | 12A7 heavy chain CDR 2 nucleotide sequence |
| 13 | 12A7 heavy chain CDR 3 polypeptide sequence |
| 14 | 12A7 heavy chain CDR 3 nucleotide sequence |
| 15 | 4B4 light chain CDR 1 polypeptide sequence |
| 16 | 4B4 light chain CDR 1 nucleotide sequence |

TABLE 1-continued

Sequences

| SEQ ID NO. | Nucleotide/Polypeptide |
| --- | --- |
| 17 | 4B4 light chain CDR 2 polypeptide sequence |
| 18 | 4B4 light chain CDR 2 nucleotide sequence |
| 19 | 4B4 light chain CDR 3 polypeptide sequence |
| 20 | 4B4 light chain CDR 3 nucleotide sequence |
| 21 | 4B4 heavy chain CDR 1 polypeptide sequence |
| 22 | 4B4 heavy chain CDR 1 nucleotide sequence |
| 23 | 4B4 heavy chain CDR 2 polypeptide sequence |
| 24 | 4B4 heavy chain CDR 2 nucleotide sequence |
| 25 | 4B4 heavy chain CDR 3 polypeptide sequence |
| 26 | 4B4 heavy chain CDR 3 nucleotide sequence |
| 27 | 12A7 full light chain variable region sequence (polypeptide) |
| 28 | 12A7 full light chain variable region sequence (nucleotide) |
| 29 | 12A7 full heavy chain variable region sequence (polypeptide) |
| 30 | 12A7 full heavy chain variable region sequence (nucleotide) |
| 31 | 4B4 full light chain variable region sequence (polypeptide) |
| 32 | 4B4 full light chain variable region sequence (nucleotide) variable region |
| 33 | 4B4 full heavy chain variable region sequence (polypeptide) |
| 34 | 4B4 full heavy chain variable region sequence (nucleotide) |
| 35 | Mcm5 polypeptide sequence |
| 36 | Mcm5 polynucleotide sequence |

EXAMPLES

Cloning of Mcm5
Stage I: Cloning Strategy

1. A verified IMAGE clone containing the human MCM5 cDNA was obtained and used as a PCR template in order to amplify a 648 bp fragment of DNA. The forward PCR primer encoded n initiation codon as well as a modified unpatented poly-Histidine tag $(HQ)_4$.
2. The PCR fragment was cloned into the inducible expression E. coli vector pTRC99a using a double restriction site strategy. This vector allows inducible expression directed by the hybrid trp/lac "trc" promoter. Downstream is a lacZ ribosome binding site (RBS) that is situated at an optimized distance from an initiation ATG codon, which is supplied by the NcoI cloning site.

Stage IIA: Expression and Purification (Small Scale—10 ml)

3. The recombinant plasmid containing the Mcm5 fragment was transformed into BL21 E. coli (non-λDE3) to ensure high yields of expressed protein.
4. Several small volume E. coli cultures were induced with IPTG. Cells will be lysed in SDS loading buffer and total protein separated by SDS-PAGE. High expressing clones will be identified by Western blotting using a mouse monoclonal supplied by Urosens.

Stage IIB: Expression and Purification (Large Scale—500 ml)

5. The identified clone with high levels of recombinant protein was cultured at the 0.5 L scale and induced with IPTG. Cells were pelleted and stored at −70° C. Cells were disrupted in a denaturing lysis buffer described by Stoeber et al. *J Natl Cancer Inst* 2002 94 1071-9.
6. His-tagged recombinant protein was affinity purified under denaturing conditions on an immobilized metal affinity (IMAC) chromatography column. Protein were eluted using an acidic buffer and dialysed against storage buffer (PBS containing 0.3 SDS)
7. Eluted protein was analyzed and quantified by SDS-PAGE and western blotting using a mouse monoclonal supplied by Urosens.

Example 1—MAb Screening ELISA

Protein A purified MAbs were obtained from the Welcome/CRUK Institute for Cancer and Developmental Biology. These antibodies were screened for their ability to bind to Mcm5.

An ELISA of recombinant His6-tagged Mcm5 was performed using Ni-NTA His-Sorb 96 well microtitre coated plate wells (Qiagen). The Ni-NTA coated plates, preblocked with BSA, ensure an orientated presentation of the 6x His tagged Mcm through Nickel affinity binding to the spacer in comparison to the random presentation of the Mcm5 to the well that would be achieved by passive adsorption plate coating. The Mcm5 at a concentration of 625 ng/ml was Nickel affinity immobilised to Ni-NTA His-Sorb surface (Qiagen) of a 96 well plate at 200 µl/well resulting in 125 ng hsMcm5/well. This was done following the manufacturers instructions to apply a His-6 tagged protein or peptide to the plate wells at a titre>100 ng/well. This was done to ensure that the protein or peptide is not limiting to Ab detection. The screening of the MAbs for development of a Mcm5 IFMA was performed with an enzyme linked immunosorbent assay (ELISA) of Mcm5. To screen MAbs, supernatants from hybridoma cultures expressing the MAbs were incubated in the microtitre wells at RT for 3 h and then washed away with an automated 96 well plate washer. The Mcm5 Ag-Ab complexes of the MAbs were detected by a colorimetric ELISA using goat anti-mouse IgG conjugated to HRP, TMB reagent and 1M $H_2SO_4$ assay stop solution, for the measurement of light absorbance at 450 nanometres (Abs 450 nm). An absence of Non-specific binding (NSB) of goat anti-mouse HRP conjugate to the Ni-NTA His-Sorb surface and Mcm5 was excluded byperforming the ELISA on wells free from MAbs. The degree of NSB of the mouse MAbs being screened to the Ni-NTA coated polystyrene wells was established by performing the ELISA in wells with the omission of Mcm5 wells in parallel to performing the ELISA in wells with the Nickel affinity immobilisation of Mcm5 to the microtitre wells.

The performance in the colorimetric ELISA of a mouse MAb in the media samples taken from the hybridomas (Table 2) was used for selection of the highlighted clones, 12A7 and 4B4. The selected MAb hybridomas were grown up to produce IgG for purification from the culture supernatant using solid-phase protein-A separation according to the manufacturer's instructions (Amersham Pharmacia Biotech Little Chalfont Buckinghamshire, UK). The 12A7 MAb gave rise to the greatest response to the Mcm5.

TABLE 2 hybridoma MAb screening ELISA Abs 450-650 results

| Mcm5 MAb | Mcm5 well response | NSB well response | Mcm5 specific response |
|---|---|---|---|
| 12A7 | 1.404 | 0.421 | 0.983 |
| 4B4 | 1.622 | 1.040 | 0.582 |

MAb Relative Affinities

Relative affinities of the protein A purified MAbs were determined by normalisation of Ab concentrations and application of the MAbs to the colorimetric screening assay under Ag-limiting conditions. Ag limiting conditions were determined by linear titration of Mcm5 across the Ni-NTA His-Sorb microtitre plate wells. An observed maximal Abs 450 nm of <3.000 is indicative of Ag limiting conditions, because the maximum Abs 450 reading obtainable when Ag is non-limiting is 4.000. The Ag titration was performed using rabbit Mcm5 PAb (101) and Goat anti Rabbit HRP to measure ELISA response. A concentration that gave 25 ng of Mcm5 available for binding to each Ni-NTA well was limiting to the ELISA Abs 450 response of the PAb. The rabbit PAb was chosen to determine Ag-limiting conditions for investigation of the mouse MAbs, as the full array of Mcm5 epitopes are bound by the PAb. This ensured that the MAbs could be investigated in combined incubation studies to determine the degree of epitope competition.

The concentration of IgG in the protein-A purified MAb solutions was determined by Abs 280 nm measurement in a spectrophotometer and MAb concentrations were normalised by dilution in PBS. The 50% maximum binding concentration was then determined by a linear dilution of the MAbs applied to an ELISA of Nickel affinity Mcm5 wells under Mcm5 Ag-limiting conditions. To demonstrate the plateau of the binding signal to the 25 ng/well hsMcm5rf on the plate the MAb 7A3 was run in the ELISA over a greater concentration range. The 50% maximum binding response for 12A7 was obtained at a concentration of 20 ng/well. 12A7 is shown by its 50% maximum binding concentration to demonstrate the highest relative affinity to hsMcm5. (Table 3).

TABLE 3

MAb titrations against limiting 25 ng/well antigen couples to Ni-NTA

| nb/well MAb | MAb | |
|---|---|---|
| | 4B4 | 12A7 |
| 0 | 0.086 | 0.051 |
| 0.25 | 0.108 | 0.189 |
| 2.5 | 0.464 | 0.762 |
| 25 | 0.966 | 1.804 |
| 500 | 1.848 | 2.808 |
| 1000 | 2.414 | 3.099 |

Example 2—Antibody Epitope Competition

For a two-site immunometric assay two MAbs that are targeted to distinct epitopes are required. In Ag limiting conditions a pair of MAbs competing for the same epitope will provide an ELISA Abs 450 nm measurement equal to the Abs 450 nm signal of the higher relative affinity Ab when it is incubated in the absence of the competing MAb, however, incubation of a pair of MAbs targeted to distinct epitopes will provide an Abs 450 measurement equal to the sum of both the MAbs individual Abs 450 nm responses to the limited Ag available provided there is an absence of steric hindrance. The MAbs 12A7 and 4B4 were normalised to the 50% maximum binding concentration of 20 ng/well of the highest relative affinity MAb 12A7. The MAbs at normalised concentration underwent an ELISA using both individual and paired Ab incubations on the 25 ng/well Mcm5 Ag limiting Ni-NTA plate. The highest Abs 450 nm signal measured from a combined incubation of a pair of the MAbs would be indicative of the most suitable MAbs for use in a two-site IFMA.

Antibody Epitope Competition Results

The Ab Ag epitope competition ELISA study results (Table 4) show that the MAb 4B4 is targeted to a distinct epitope compatible for two-site binding with the 12A7. The distinct epitope targeted by 4B4 is demonstrated by the Abs 450 response' being equal to the sum of both MAbs binding to the limiting Ag when 4B4 was incubated in parallel to the other MAbs.

TABLE 4

Ab Ag epitope competition ELISA study results

| MAb 20 ng/well incubation | Mcm5 25 ng/well Abs 450-650 response |
|---|---|
| 12A7 | 1.375 |
| 4B4 | 1.244 |
| 12A7 + 4B4 | 2.693 |

The MAbs were incubated at a normalised concentration of 20 ng/well, the 50% maximum binding concentration of the MAb with the highest relative affinity 12A7. The optimal MAbs for two-site immunoassay development are highlighted in blue, and their ELISA Abs 450 responses highlighted in yellow.

Example 3—Epitope Mapping

Materials Used:

| | |
|---|---|
| Microarray Content: | The sequence of antigen Mcm 5 (aa 367-582) was translated into 15 aa peptides with a peptide-peptide overlap |
| Samples: | Mouse monoclonal IgG antibodies 12A7 and 4B4 |
| Washing Buffer: | PBS, pH 7.4 with 0.05% TWEEN 20 ® (3 × 1 min after each assay) |
| Blocking Buffer: | Rockland blocking buffer MB-070 (30 min before the first assay) |
| Incubation Buffer: | PBS, pH 7.4 with 0.05% TWEEN 20 ® and 10% Rockland blocking buffer |
| Assay Conditions: | Antibody concentrations of 1 µg/ml and 10 µg/ml in incubation buffer; incubation for 16 h at 4° C. and |
| Secondary Antibody: | Goat anti-mouse IgG (H + L) DyLight 680 antibody; |
| Control Antibodies: | Monoclonal anti-HA (12CA5)-DyLight680 (1:1000), monoclonal anti-FLAG(M2)-DyLight800 (1:500); staining in |
| Scanner: | LI-COR Odyssey Imaging System; scanning offset 0.8 mm, resolution 21 µm, scanning intensity red/green of 5/7 |

Pre-staining of one of the peptide microarrays was done with the secondary goat anti-mouse IgG (H+L) DyLight680 antibody at a dilution of 1:5000 to investigate background interactions with the antigen-derived peptides that could interfere with the main assays. Subsequent incubation of the peptide microarrays with mouse monoclonal IgG antibodies 12A7 and 4B4 at concentrations of 1 µg/ml and 10 µg/ml in incubation buffer was followed by staining with the secondary antibody and read-out at a scanning intensity of 5 (red). HA and Flag control peptides framing the peptide arrays were finally stained as internal quality control to confirm the assay quality and the peptide microarray integrity (scanning intensities red/green: 5/7).

Quantification of spot intensities and peptide annotation were done with PepSlide® Analyzer. A software algorithm breaks down fluorescence intensities of each spot into raw, foreground and background signal and calculates the standard deviation of foreground median intensities. Based on averaged foreground median intensities, intensity maps were generated and interactions in the peptide maps highlighted by an intensity color code with red for high and white for low spot intensities.

We further plotted averaged spot intensities of all assays with the antibody samples against the antigen sequence from the N- to the C-terminus to visualize overall spot intensities and signal to noise ratios. The intensity plots were correlated with peptide and intensity maps as well as with visual inspection of the microarray scans to identify peptides and epitopes that were recognized by the antibody samples. In case it was not clear if a certain amino acid contributed to antibody binding.

After 15 min pre-swelling in washing buffer and 30 min in blocking buffer, one of the peptide microarrays was initially incubated with the secondary goat anti-mouse IgG (H+L) DyLight680 antibody at a dilution of 1:5000 for 30 min at room temperature to analyze background interactions with the antigen-derived peptides. At a scanning intensity of 5, we did not observe any background due to non-specific binding of the secondary antibody. Data quantification with PepSlide® Analyzer was neither possible nor required, since the absence of any spot pattern hampered alignment of the microarray grid.

The peptide microarrays were incubated with mouse monoclonal antibody 12A7 at concentrations of 1 µg/ml and 10 µg/ml (top right). After each incubation, staining with the secondary goat anti-mouse IgG (H+L) DyLight680 antibody was followed by read-out at a scanning intensity of 5. We observed a strong and well-defined epitope-like spot pattern formed by a row of neighbored peptides with a consensus motif at excellent signal to noise ratios.

The final staining of the HA and Flag control peptides framing the peptide microarray gave rise to the expected and well-defined spot pattern and validated the overall peptide microarray integrity.

Data quantification was followed by generation of peptide and intensity maps as well as of intensity plots for the assays with mouse monoclonal antibody 12A7 at concentrations of 1 µg/ml and 10 µg/ml; the intensity plot of the latter was leveled to provide a clearer data overview. The signals were based on the epitope-like spot pattern observed in the microarray scan and attributed to peptides with the consensus motif WDETKGE.

The peptide microarrays were incubated with mouse monoclonal antibody 4B4 at concentrations of 1 µg/ml) and 10 µg/ml. After each incubation, staining with the secondary goat anti-mouse IgG (H+L) DyLight680 antibody was followed by read-out at a scanning intensity of 5. We observed two strong and well-defined epitope-like spot patterns formed by a row of neighbored peptides with consensus motifs at excellent signal to noise ratios. At an antibody concentration of 10 µg/ml the raw intensities of the epitope-like spot pattern were similar but the background interactions were slightly increased indicating a signal saturation of the antibody in the concentration range of 1-10 µg/ml. The final staining of the HA and Flag control peptides framing the peptide microarray gave rise to the expected and well-defined spot pattern and validated the overall peptide microarray integrity.

Data quantification was followed by generation of peptide and intensity maps as well as of intensity plots for the assays with mouse monoclonal antibody 4B4 at concentrations of 1 µg/ml and 10 µg/ml; the intensity plot of the latter was leveled to provide a clearer data overview. At an antibody concentration of 10 µg/ml the raw intensities of the epitope-like spot pattern were similar but the background interactions were slightly increased leading to reduced normalized signal intensities. The signals were based on the epitope-like spot patterns observed in the microarray scan and attributed to peptides with the consensus motifs DDRVAIH and WDETKGE.

Example 4

Materials

Single voided urine specimens were obtained from patients attending a haematuria clinic at Heatherwood Hospital (Heatherwood and Wexham Park Hospitals NHS Foundation Trust), having obtained ethical approval from the Local Research Ethics Committee. Urinalysis using Multistix 10 SG dipsticks (Siemens) was carried out on fresh samples and the remainder of the urine was dispensed into 1 ml or 15 ml Falcon tubes which were placed in dry ice for transport to the laboratory.

Mcm5

Figure 2:
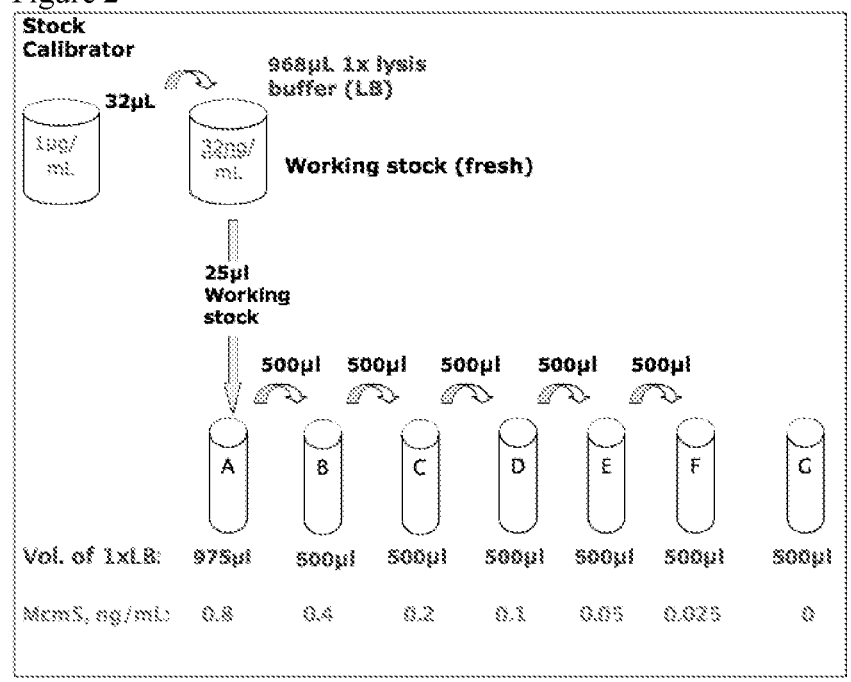
FIG. 2 shows a diagram describing how to dilute the stock calibration solution.
Figure 3:
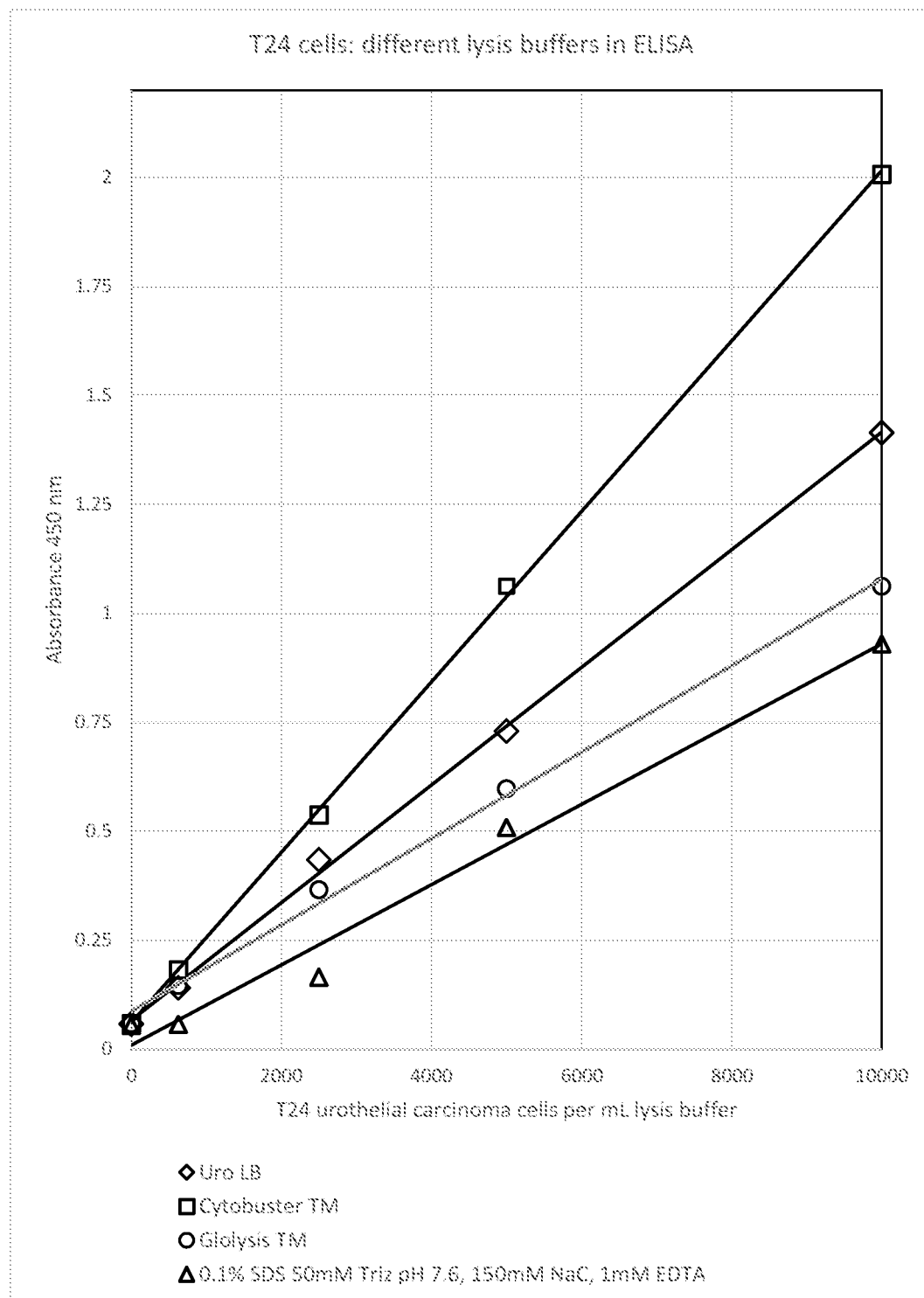
FIG. 3 shows a graph comparing the amount of Mcm5 released from urothelial carcinoma cells after exposure to 4 different lysis buffers (Uro LB "0.08% sodium deoxycholate, 0.08% CHAPS, 2 mM EDTA, 150 mM Trizma pH 7.6), Cytobuster TM, Glolysis TM, and 0.1% SDS 50 mM Trizma pH 7.6, 150 mM NaC, 1 mM EDTA.
Figure 4:
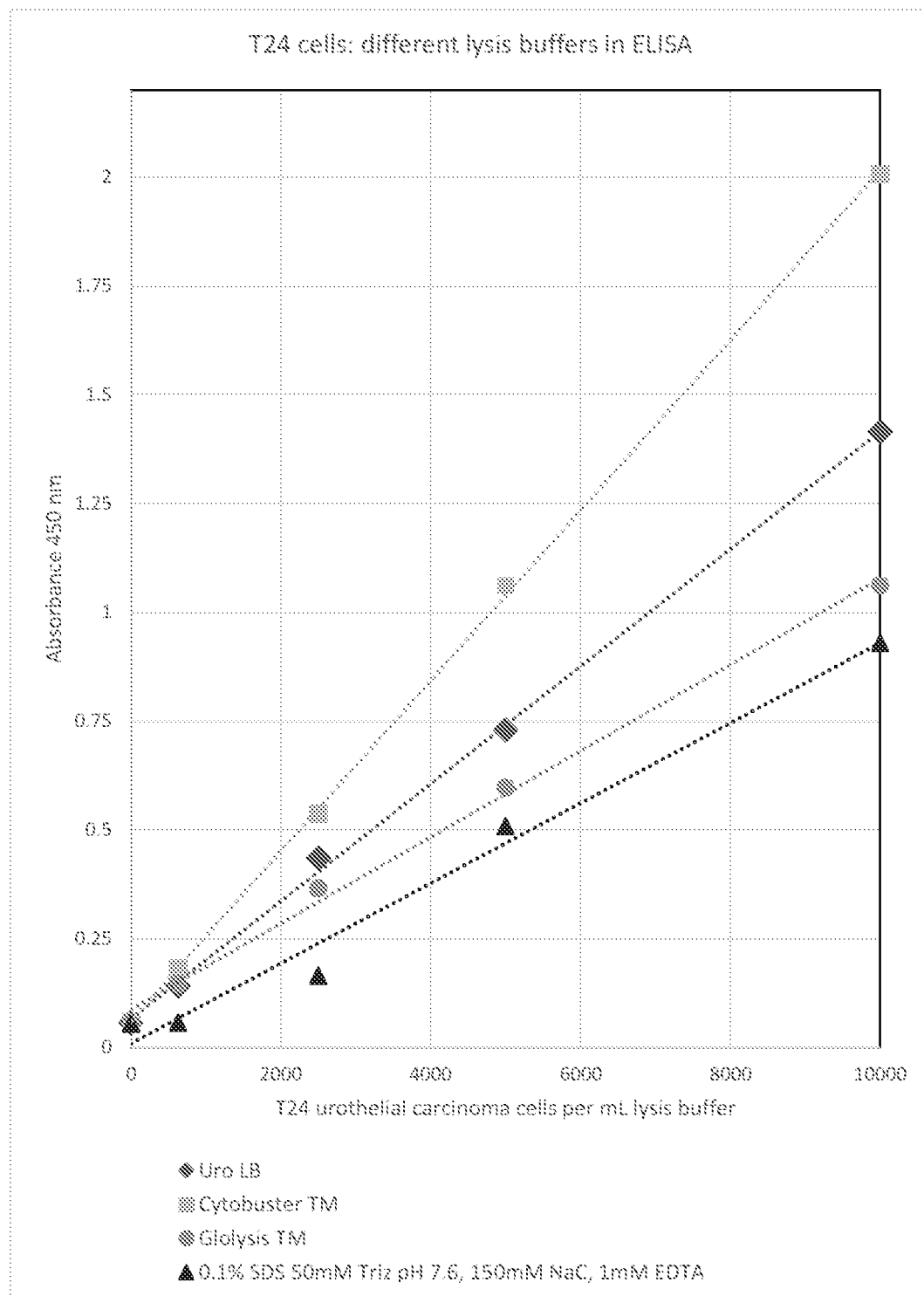
FIG. 4 shows a graph comparing the amount of Mcm5 released from urothelial carcinoma cells after exposure to 4 different lysis buffers (Uro LB "0.08% sodium deoxycholate, 0.08% CHAPS, 2 mM EDTA, 150 mM Trizma pH 7.6), Cytobuster TM, Glolysis TM, and 0.1% SDS 50 mM Trizma pH 7.6, 150 mM NaC, 1 mM EDTA.

An embodiment of the invention is a simple ELISA test for Mcm5, which usefully replaces the specialized and complex Mcm5 DELFIA® test (see Stoeber et al 2002 (Journal of the National Cancer Institute, 94, 1071-1079; 2002), thus the test could be carried out in a typical clinical chemistry laboratory. The test is a direct double-monoclonal antibody sandwich enzyme-linked immunoassay. Both antibodies have high affinity and specificity for the antigen Mcm5. Any Mcm5 in the sample under test is captured by a specific monoclonal antibody bound to the surface of the microtitre plate well. Detector antibody is then added, which binds to a different site on the antigen and which is linked to the enzyme horseradish peroxidase (HRP). The presence and amount of HRP retained in plate wells is assessed by measuring the intensity of colour that develops after the addition of tetramethylbenzidine (TMB), which is a chromogenic substrate of HRP. Optical density is proportional to the concentration of Mcm5 in the sample within defined limits. By testing a range of concentrations of Mcm5, a dose-response curve can be generated from which the antigen concentration of an unknown can be ascertained (see FIGS. 2 and 3).

Two monoclonal antibodies (mAbs) are used in the assay, 12A7 and 4B4. The antibodies were obtained from Cancer Research Technology Ltd (CRT) under a non-exclusive licensing agreement with the applicant. For ELISA tests, mAb 12A7 was used for plate coating, and mAb 4B4 for detection.

Specimen collection and preparation: The test can be performed on human urine. Samples should be collected in, for example, 150 mL plastic bottles with a screw cap, which should be clean but not necessarily sterile. The collection bottle should not contain any preservative and ideally should be of a volume of greater than 100 mL. Samples may be stored for up to 4 hours at 2-8° C. prior to use. To prepare urine specimens for assay 30 mL of the sample is transferred to a 50 mL plastic centrifuge tube with screw cap After centrifugation for 5 min at 1,500 g the supernatant is carefully decanted and treated as waste according to local H&S guidelines. The tubes are placed inverted on absorbent paper and excess liquid is allowed to drain. 250 µl Lysis/sample buffer is added to the pellet; the pellet is resuspended using an adjustable pipette with disposable tip.

Reagents: Test components are described herewith in the form of a kit (see Table 1). Each kit contains sufficient materials for a single 96-well microplate, or 80 determinations in duplicate wells if the whole plate is used at one time.

TABLE 1

| MCM5 kit contents | Quantity |
|---|---|
| Anti-MCM5 antibody coated microplate comprising twelve 8-well strips coated with mouse monoclonal anti-MCM5 antibody and a stabiliser packed in a sealed foil pouch with desiccant. | 1 microtitre plate, 96 wells |
| Wash solution, 20× concentrate. PBS buffer containing TWEEN 20 ® at 0.05% after dilution to 1 litre in deionized water. | 1 × 50 mL |
| Anti-MCM5 antibody-HRP conjugate. Mouse anti-MCM5 monoclonal antibody conjugated to horseradish peroxidase (HRP) at working concentration in a buffered solution containing protein and an anti-microbial agent. | 1 × 11 mL |
| TMB substrate reagent. A colourless solution that develops a blue colour in the presence of HRP. | 1 × 11 mL |
| Stop solution. Aqueous 1M hydrochloric acid. Personal protective equipment is recommended to avoid direct exposure. | 1 × 11 mL |
| Lysis/running buffer. An aqueous solution containing a buffering agent and a mild detergent. | 1 × 15 mL |
| Calibrator set. Vials containing lyophilised purified MCM5 protein at concentrations of 900, 300, 100 and 33 pg/mL, to be reconstituted in 1 mL lysis/running buffer. | 4 vials |
| Controls set. Vials containing lyophilised protein/cells. | 2 vials |
| Adhesive material. For sealing the plate wells during incubations. | 1 sheet |
| Instructions for Use. Also available at www.urosens.com | 1 copy |

In addition to the constituents listed in Table 1, the following additional materials are helpful and may optionally be provided in a kit of the invention. These materials are to be regarded as separately disclosed and may therefore be individually added to the kit of the invention. Pipette(s) capable of delivering 50 µl and 100 µl volumes with a precision of better than 1.5%; dispenser(s) for repetitive deliveries of 100 µl and 300 µl volumes with a precision of better than 1.5%; microplate washer or a squeeze bottle (optional); a microplate reader with 450 nm and 620 nm wavelength absorbance capabilities, absorbent paper for blotting the microplate wells and plastic wrap or microplate covers for incubation steps plus a timer.

Test Procedure: Before proceeding with the assay, all reagents should be brought to room temperature (20-27° C.) for 30 minutes. Unused reagents are stored at 2-8° C. after use. Sufficient microplate well strips are removed for each sample to be tested, including a dilution series of calibrators and quality control samples, to be assayed in duplicate. 100 µL of the appropriate calibrator- or specimen is pipetted into the assigned well which is incubated at room temperature (20-27° C.) for thirty (30) minutes on a rotary microtitre plate shaker at 700 rpm. The contents are discarded and the wells washed by six changes of 300 µl of wash buffer. 100 µl of the Anti Mcm5 HRP Antibody reagent/conjugate is then added to each well. After mixing, the wells are incubated stationary for 30 minutes at room temperature (20-27° C.). The contents of the microplate are then discarded by decantation or aspiration. If decanting, tap and blot the plate dry with absorbent paper and then wash the wells as described above. 100 ul of Substrate Reagent is then added to all wells and incubated at room temperature (20-27° C.) for thirty 30 minutes. The reaction is stopped by addition of 100 uL of stop solution to each well. The absorbance in each well is read at 450 nm (using a reference wavelength of 620-630 nm to minimize well imperfections) in a microplate reader. The results should be read within 30 minutes of adding the stop solution.

Calibrator samples are provided. These are prepared using a serial dilution at the time of the assay and discarded after use (see FIG. 2).

To interpret the results a dose-response curve is used to ascertain the concentration of Mcm5 in unknown specimens. This can be constructed manually or automatically using a computer programme. For manual calculation, record the absorbance obtained from the printout of the microplate reader. Plot the absorbance for each duplicate dilution versus the corresponding Mcm5 concentration in ng/mL on linear graph paper then draw the best-fit curve through the plotted points. To determine the concentration of Mcm5 for an unknown, locate the average absorbance of the duplicates for each unknown on the vertical axis of the graph, find the intersecting point on the curve, and read the concentration (in ng/ml) from the horizontal axis of the graph.

Table 2 illustrates the results from a typical experiment.

TABLE 2

| Sample ID | Value (pg/ml) | Well number | Abs (A) | Mean Abs (B) |
|---|---|---|---|---|
| CAL G (blank) | 0 | A1 | 0.082 | 0.083 |
|  |  | B1 | 0.084 |  |
| CAL F | 25 | C1 | 0.164 | 0.163 |
|  |  | D1 | 0.162 |  |
| CAL E | 50 | E1 | 0.245 | 0.242 |
|  |  | F1 | 0.239 |  |
| CAL D | 100 | G1 | 0.395 | 0.393 |
|  |  | H1 | 0.390 |  |
| CAL C | 200 | A2 | 0.693 | 0.681 |
|  |  | B2 | 0.669 |  |
| CAL B | 400 | C2 | 1.281 | 1.252 |
|  |  | D2 | 1.222 |  |
| CAL A | 800 | E2 | 2.458 | 2.342 |
|  |  | F2 | 2.226 |  |

The Mcm5 procedure has an analytical detection limit of <7 pg/ml.

Example 5—Clinical Study of Mcm5 in 116 Subjects being Investigated for Bladder Cancer Urine specimens were obtained from 116 patients the majority of whom were subsequently examined by flexible cystoscopy and scanning by CT or ultrasound. If abnormal results were obtained the patients were referred for biopsy. Where available the results of these investigations were collected and added to the data set. The levels of Mcm5 were measured in each subject using the ELISA technique described above (Example 4). Eight cases of bladder cancer were clinically confirmed of which five were scored as positive in the Mcm5 assay.

TABLE

| In the table "+" indicates that the Mcm5 assay result exceeded the mean of the known negatives + 3 SDs (negative mean OD 0.05, SD 0.0593). Therefore the cut point was arbitrarily set at OD 0.23. | | |
|---|---|---|
| Patient ID Number | Grade/Stage Location | ELISA result |
| 6 | G2 pTa, papillary tumour, bladder | + |
| 25 | pTa, ureter | − |
| 27 | G2 pTa, papillary tumour, bladder | − |

TABLE-continued

| In the table "+" indicates that the Mcm5 assay result exceeded the mean of the known negatives + 3 SDs (negative mean OD 0.05, SD 0.0593). Therefore the cut point was arbitrarily set at OD 0.23. | | |
|---|---|---|
| Patient ID Number | Grade/Stage Location | ELISA result |
| 57 | G1 pTa, 5 mm tumour, bladder | − |
| 86 | Squamous cell carcinoma, bladder | + |
| 92 | Squamous cell carcinoma, bladder | + |
| 96 | G3 pT2, bladder (gross haematuria) | + |
| 115 | G3 pT2, bladder | + |

There were also four cases in which a positive ELISA result occurred in the absence of a confirmed diagnosis of malignancy: Patient 13 (Papillary lesions were observed in the bladder; biopsy result was not recorded. Prostate occlusive); Patient 30 (No other pathology recorded); Patient 65 (Nephrectomy recorded); Patient 101 (enlarged prostate with calcification). It is known that the presence of calculi can cause false positive results due to the abrasive effect of the material on the basal layer of the epidermis leading to release of MCM+ cells, but rate of such cases is too small to impact on the present assay.

Assay Statistics

Standard assay statistics were calculated for the Mcm5 assay data. Although the true clinical end-point was not available for all patients in the study, the skilled person will appreciate that this modest panel has yielded convincing results. In particular the study has provided a realistic estimate of specificity of 96% (104/108).

Example 6—Comparison of Various Buffers

Known numbers of T24 urothelial carcinoma cells were lysed in each buffer and the lysates tested in ELISA for Mcm5. The results demonstrate a marked difference in lysis efficiency in this assay. The buffer containing SDS is typical of those described in the literature but is significantly less efficient than Cytobuster or 'Urosens LB' (0.08% sodium deoxycholate, 0.08% CHAPS, 2 mM EDTA, 150 mM Trizma pH 7.6). The results are presented in FIG. 3.

Example 7

Figure 5:
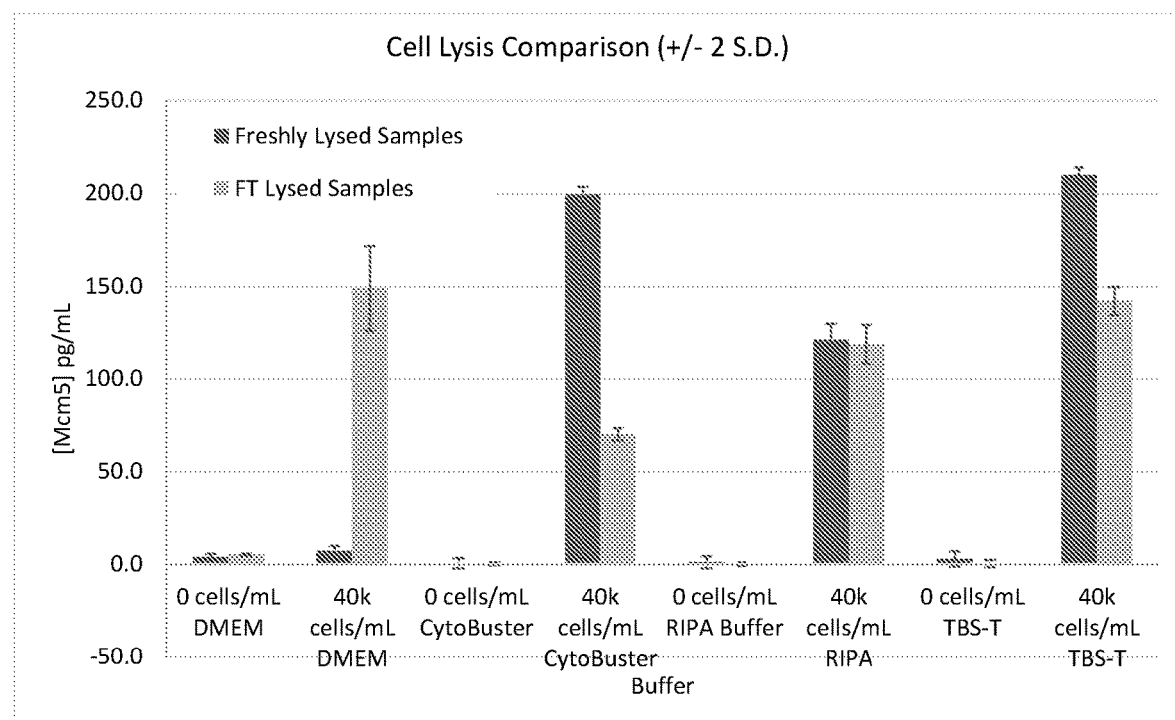
FIG. 5 shows a graph comparing CytoBuster, RIPA buffer and TBS-T Buffer prior to modification.

The lysis of cells in CytoBuster was compared to cells in TBS TRITON™ buffer (TBST) and RIPA buffer with a control of cell pellets reconstituted in DMEM (cell culture medium). The results are described in FIG. 5.

The potency of Mcm5 in the lysed samples was tested after application of buffer to cells. Some samples were frozen after exposure to buffer and before testing. Ideally, a universal buffer that would be used in both scenarios would be useful.

The control results proved that when fresh samples were tested, the cells remain intact when no lysing agent is added, but post-freeze-thaw (FT), the cells burst by mechanical breakdown of the cell membrane, thereby releasing Mcm5. This experiment showed that when fresh lysates are used, the TBST buffer is roughly equivalent to the CytoBuster. However, after samples have been frozen, the CytoBuster lysates undergo a drastic loss of potency, whereas the TBST is not as strongly affected. The RIPA lysates buffer, although lower when derived from fresh sample retains all of the potency post-FT.

Example 8

Figure 6:
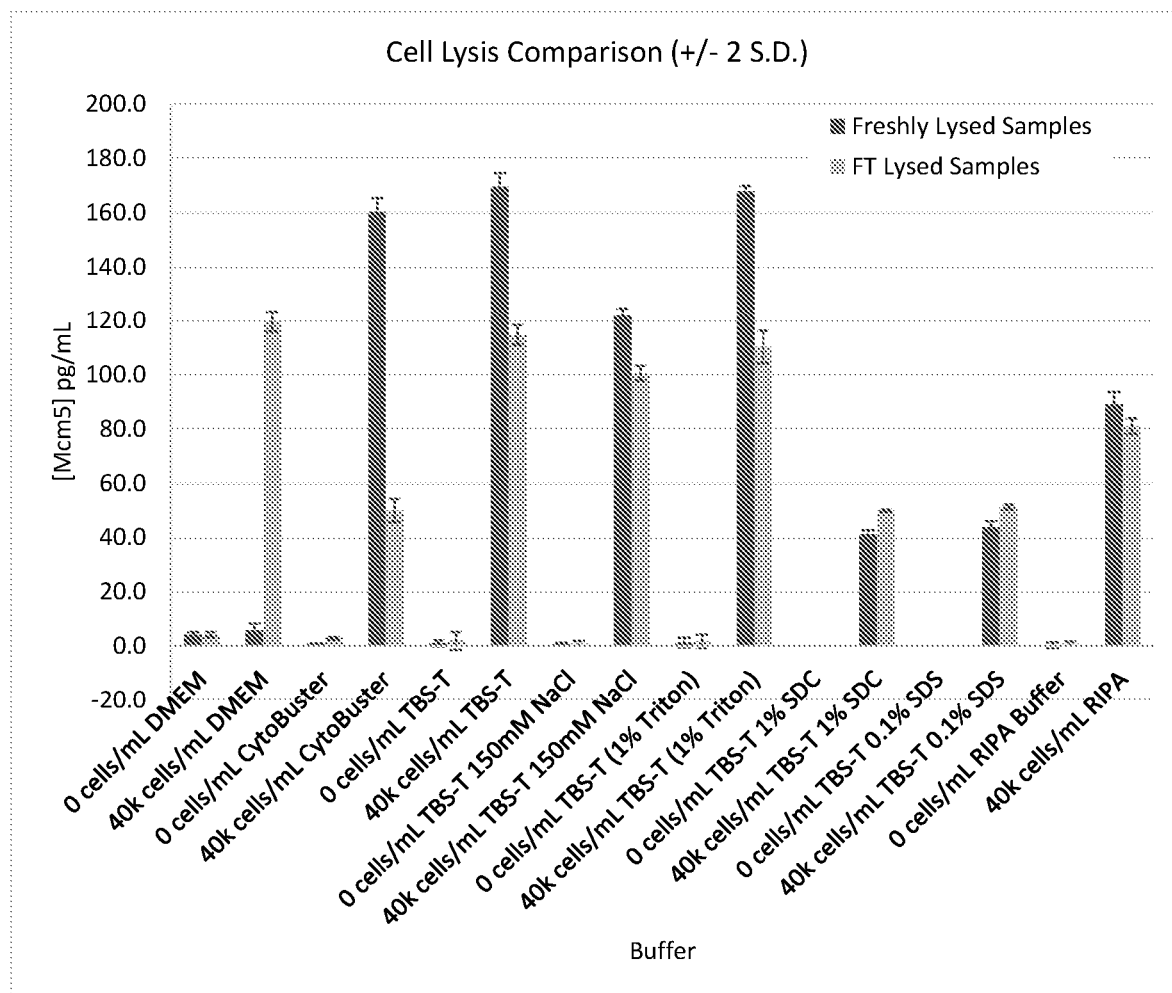
FIG. 6 shows a graph comparing buffers based on TBST Buffer and comprising elements from RIPA buffer, Pre-& Post-Lysate Freeze-Thaw.

Additional components were added to TBT to try to improve stability of TBST lysates. The potency of Mcm5 in the lysed samples was tested after application of buffer to both fresh and frozen cells. The results of this experiment are presented in FIG. 6.

Figure 7:
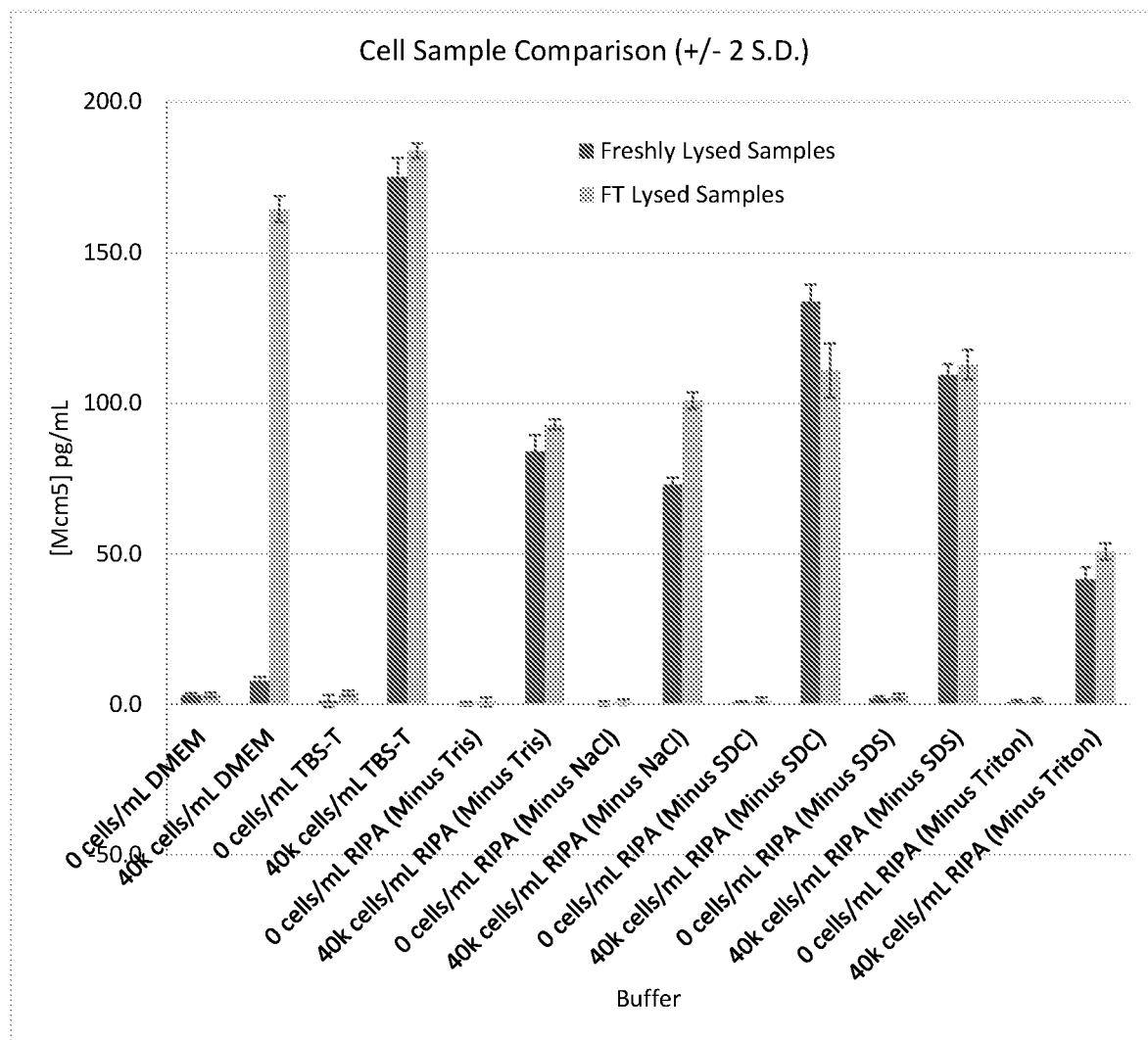
FIG. 7 shows a graph comparing buffers based on RIPA buffer but having some RIPA buffer elements removed, Pre-& Post-Lysate Freeze-Thaw.

These data (described in FIG. 6) demonstrated that the stabilising components of the RIPA buffer are the sodium deoxycholate (SDC) and the sodium dodecyl sulfate (SDS), but unfortunately the incorporation of these elements into the simpler TBST buffer cause a dramatic loss in signal. A supplemental test was performed to remove elements of the RIPA buffer one-by-one to see if removal of any element could improve the RIPA signal to the same level as the TBST while retaining stability. The results are described in FIG. 7.

Example 9

Figure 8:
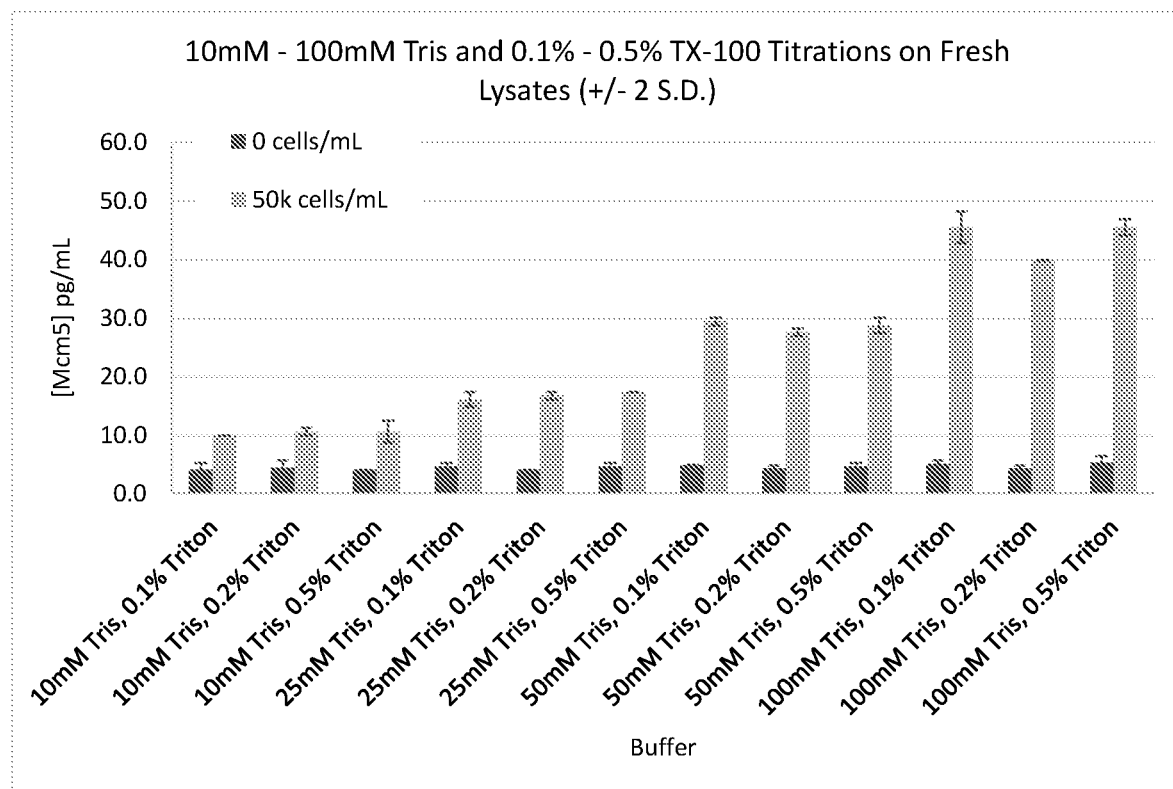
FIG. 8 shows a graph comparing buffers having different concentrations of Iris and TRITON™ X-100 (polyethylene glycol p-(1.1.33,-tetramethylbutyl)-phenyl ether), using Fresh Lysates.

Various buffers comprising differing concentrations of Tris and TRITON™ X-100 were compared. The potency of Mcm5 in the lysed samples was tested after application of buffer to both fresh and frozen cells. The results are presented in FIG. 8.

The data showed that increasing the Tris concentration caused an improvement on cell lysate Mcm5 levels, although increasing the TRITON™ X-100 concentration had no effect.

Figure 9:
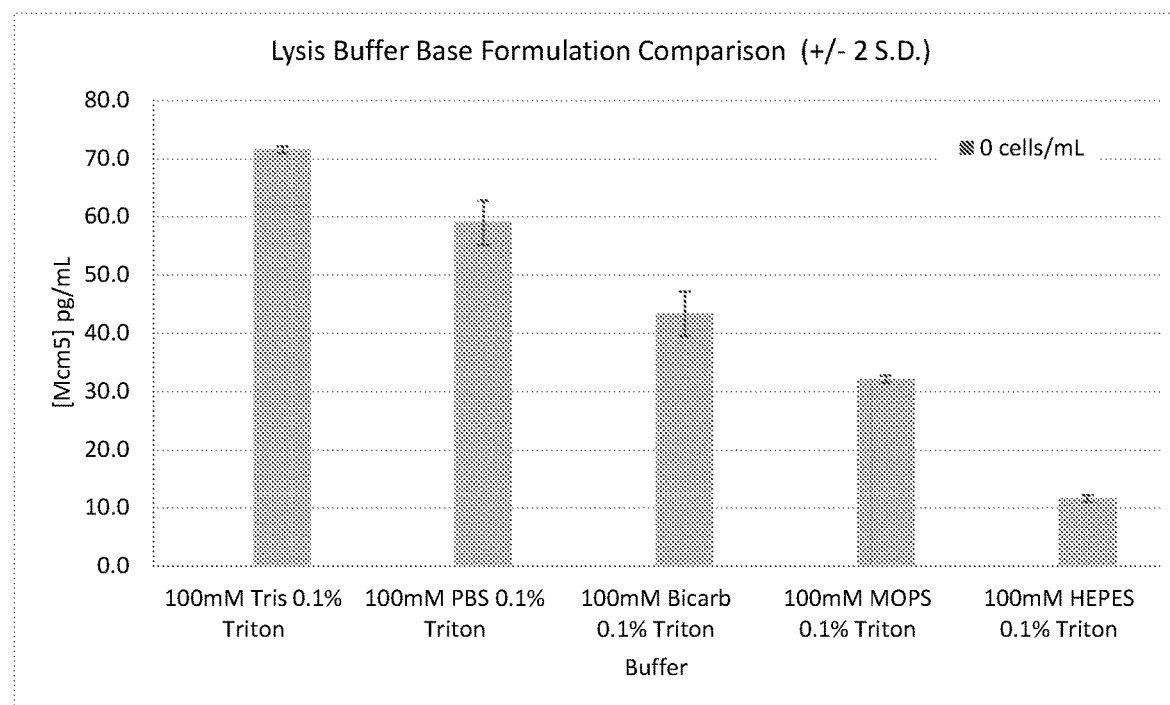
FIG. 9 shows a graph comparing different buffer base formulations (TBS, PBS, Bicarbonate, MOPS & HEPES), using Fresh Lysates.

To ensure the optimal base for the lysis buffer is used before progressing further, several compounds were tested across various pH ranges and buffer types. Several of these buffers gave good results, but TBS was shown to have the highest signal. These data are described in FIG. 9.

Example 10

Figure 10:
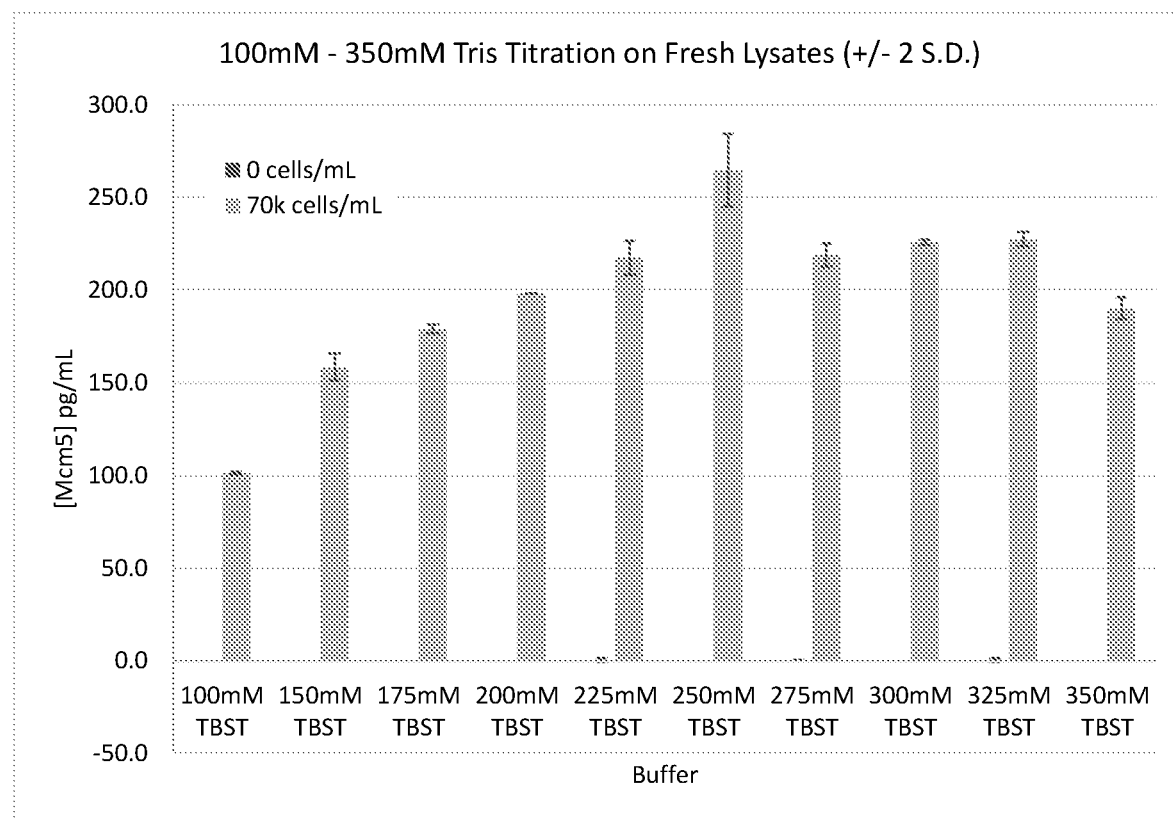
FIG. 10 shows a graph comparing buffers having different concentrations of Tris (100 mM-350 mM), using Fresh Lysates.

A further titration of Tris was performed to see whether the signal would still increase if a higher buffer concentration was used, and to see where the improvement plateaued. The results are presented in FIG. 10.

The level of Mcm5 begins to plateau at 225 mM Tris, with only the 250 mM Tris being higher, and then the signal is stable until 325 mM, after which a decrease is seen. To avoid potential issues with manufacturing and variation, a concentration on a stable area of the plateau would be the optimal choice, such as 300 mM.

Example 11

Figure 11:
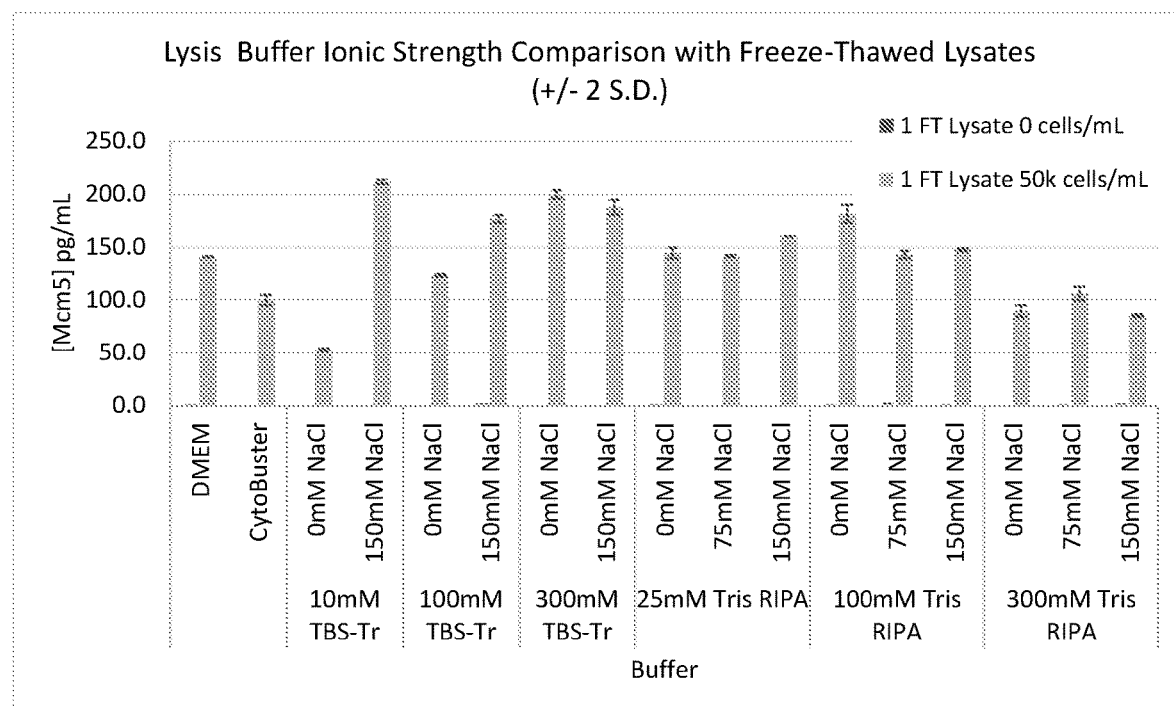
FIG. 11 shows a graph comparing buffers based on TBS-T and RIPA buffers but having altered ionic strength, using Freeze-Thawed Lysates.

It was hypothesised that altering the Tris concentration may be effective due to increased ionic strength. Since this can be equally achieved by adding NaCl, compositions having different concentrations of NaCl were tested. The results are presented in FIG. 11.

The data shows that increasing the NaCl concentration in TBST (TBS+TRITON™ X-100) buffers with lower Tris levels improves signal, but the same effect is not seen in RIPA buffer, regardless of the Tris concentration. Increasing the Iris concentration does not seem to have any substantial improvement on standard RIPA buffer (25 mM Tris and 150 mM NaCl) signal even if the NaCl level is reduced in compensation. The 10 mM Iris 150 mM NaCl TBST has the highest signal obtained in the data set (approximately double that of the CytoBuster), sc this buffer was optimised in terms of NaCl concentration and assessed separately for stabilising components.

Example 12

Figure 12:
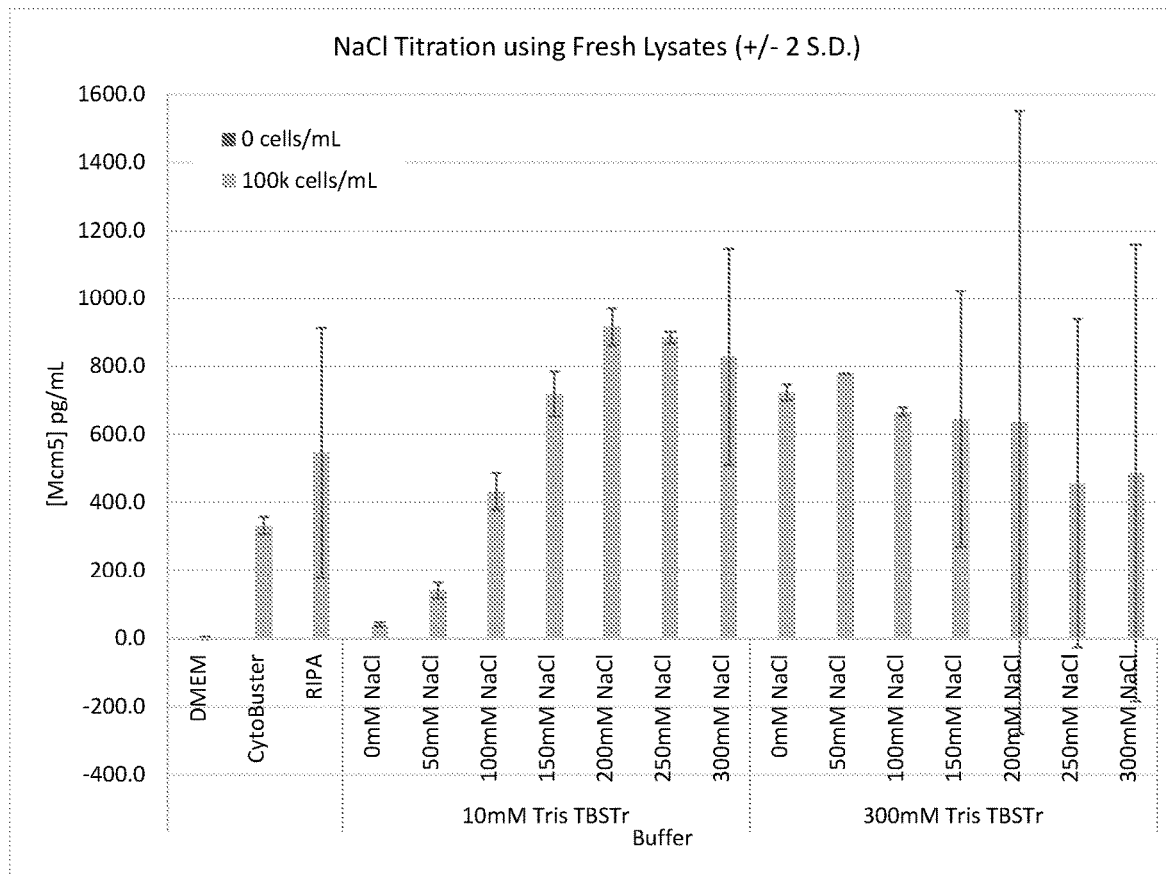
FIG. 12 shows a graph comparing TBS-T buffers having altered NaCl strength, using Freeze-Thawed Lysates.

The data presented in Example 8 suggests buffers having around 10 mM tris are most effective, so buffers having 10 mM tris and different NaCl concentrations were investigated. The results are presented in FIG. 12.

The titration of NaCl shows the best candidate to be the 101 mM Tris with 200 mM NaCl. The data also seems to show that when the ionic strength reaches a certain point, precision is compromised. The chosen formulation of the buffer from this point was 10 mM Tris, 200 mM NaCl & 0.1% TRITON™ X-100, to which stabilising compounds were then added to find a suitable final formulation.

Example 13

Various stabilisers were tested for tested for their effectiveness in stabilising the Mcm5 samples when combined with TBS-T.

Figure 13A:
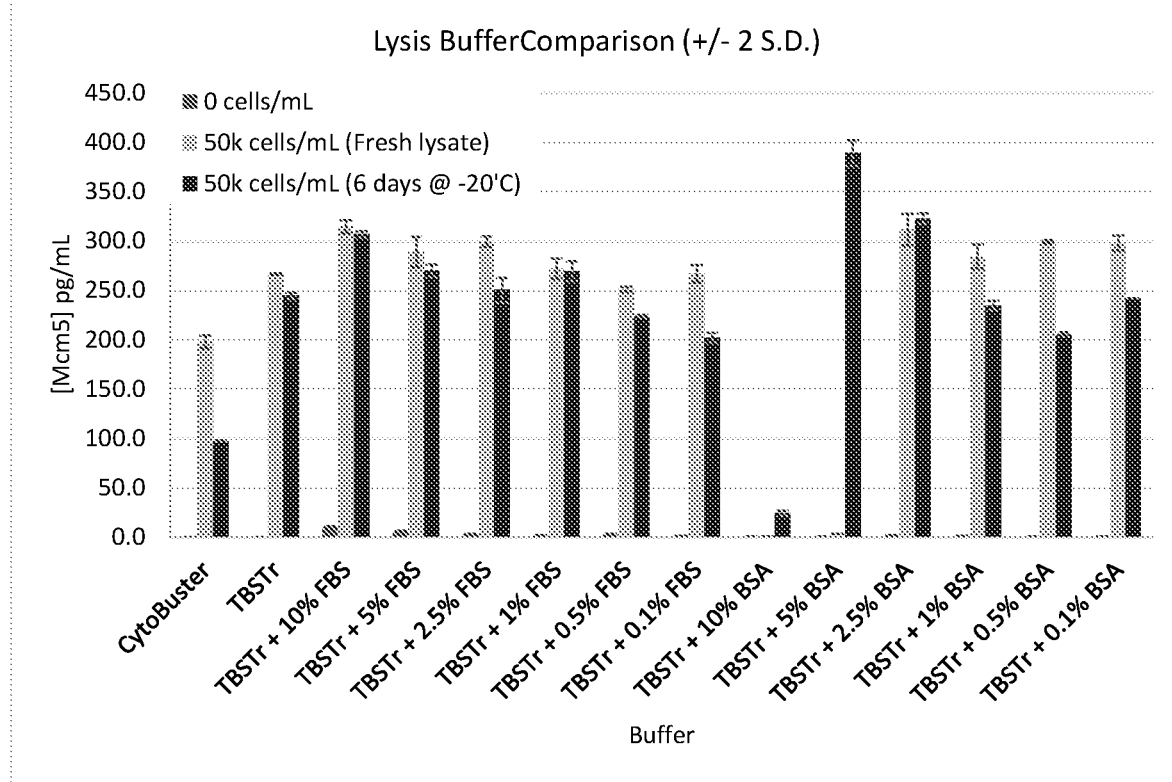
FIGS. 13A and 13B show graphs comparing TB S-T buffers which further comprise various stabilising agents.
Figure 13B:
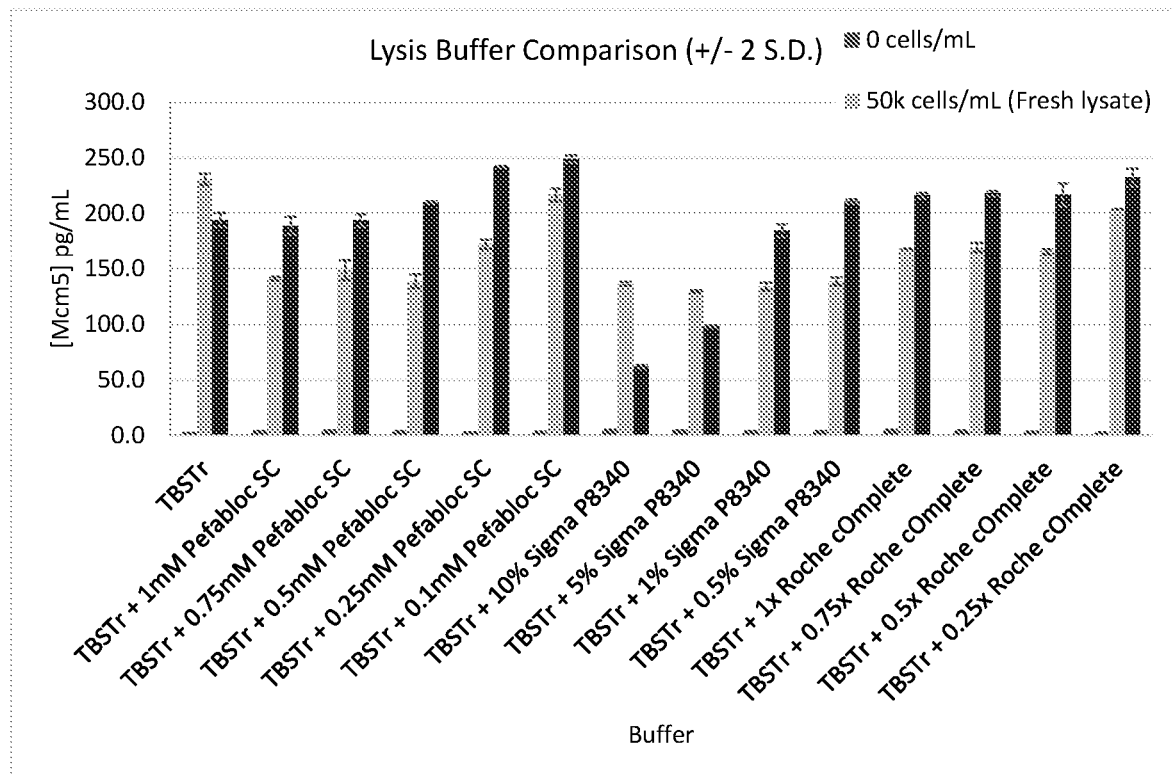

In terms of potential candidates, the 1% FBS (foetal bovine serum), 2.5% BSA (bovine serum albumin), 0.25 mM Pefabloc SC, 0.1 mM Pefabloc SC, 0.5% Sigma P8340 protease inhibitor cocktail and the 0.25× Roche cOmplete protease inhibitor cocktail all had encouraging data without compromising the background or positive sample signal compared to the buffer without stability additives. These data are presented in FIGS. 13A and 13B.

Figure 14:
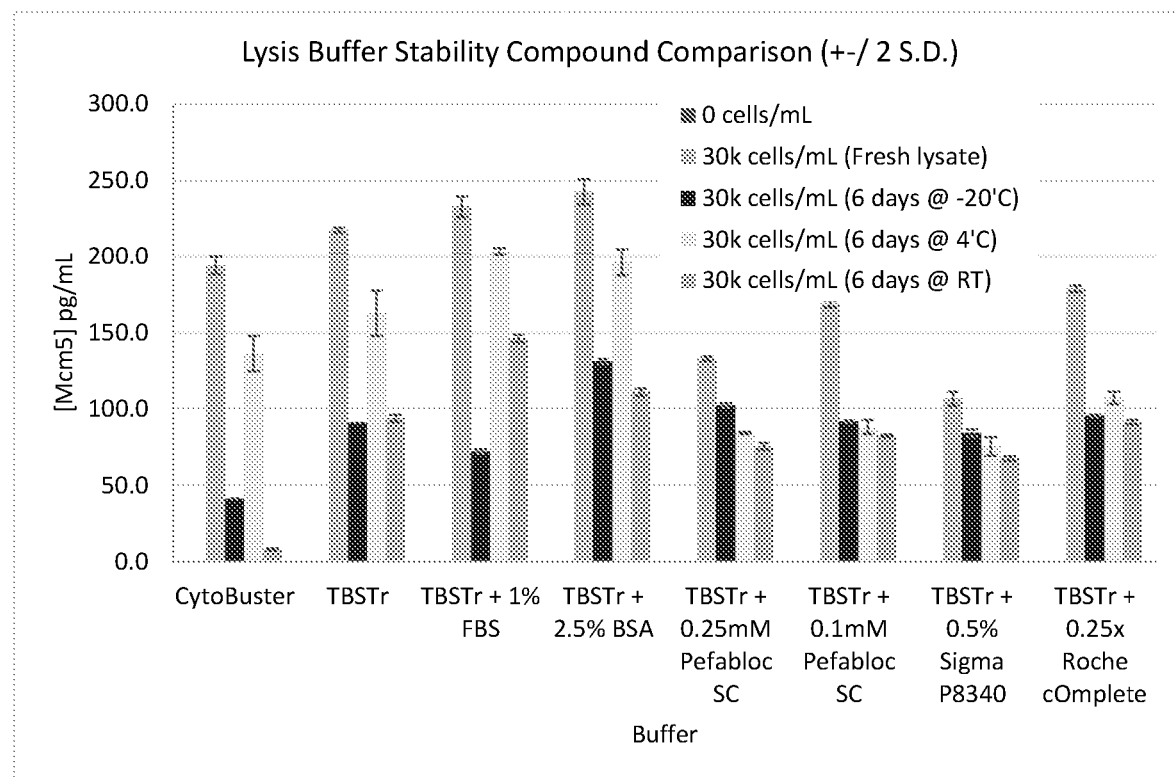
FIG. 14 shows a graph comparing TBST buffers comprising different concentrations of Stabilising Agents, after 6 Days Storage.

These compounds were tested with various storage temperatures after 6 days to see how they compared to the additive-free TBST and the CytoBuster. These data are presented in FIG. 14.

All the stabilisers were effective at stabilising the compositions. The commercially produced protease inhibitor cocktails (Pefabloc, Sigma P3840 & Roche cOmplete) were stable, but reduced the Mcm5 signal. The 2.5% BSA performed better than the 1% FBS at −20° C. Performance at 4° C. and fresh were equivalent for 1% FBS and 2.5% BSA, and both seem to increase signal comparison to standard TBST buffer. As there was a loss at −20° C. for the BSA, a repeat experiment was performed using additional cell lines to confirm the improvement to stability.

Example 14

Figure 15A:
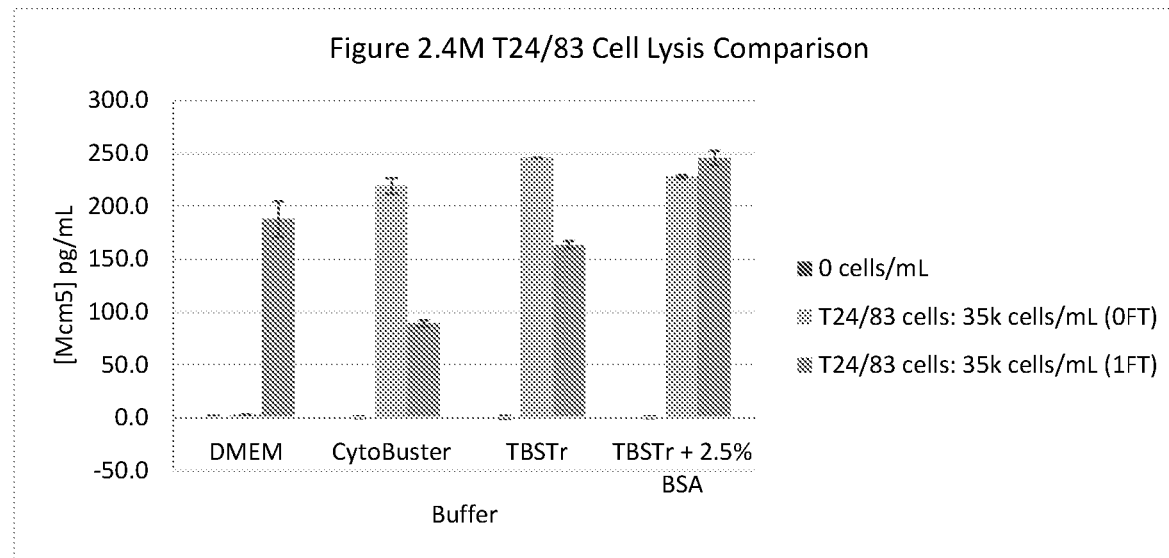
FIGS. 15A, 15B and 15C show graphs assessing the efficacy of TBST Buffer+/−2.5% BSA in various cell lines.
Figure 15B:
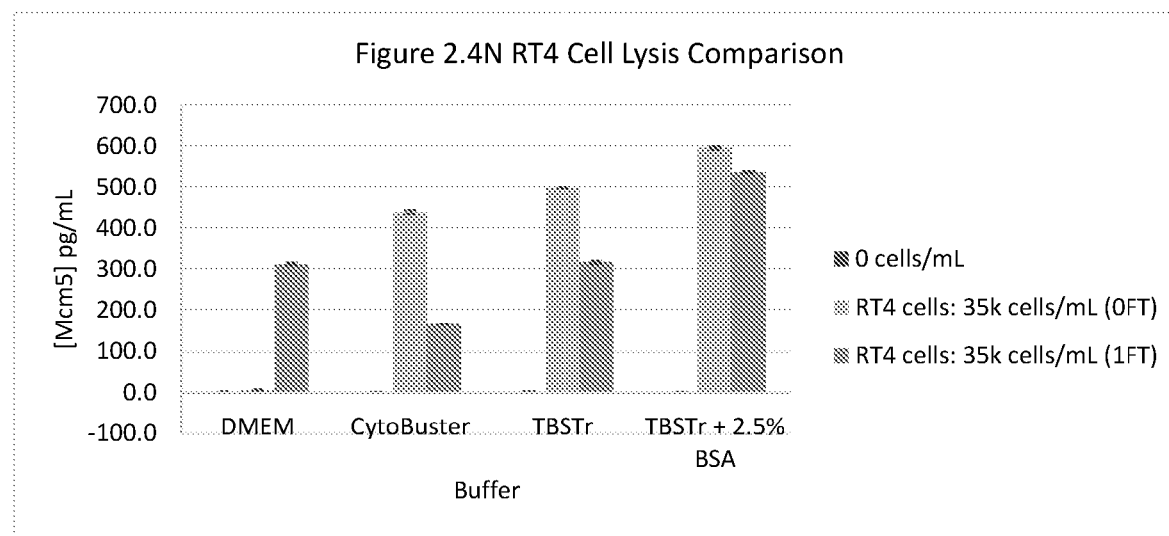
Figure 15C:
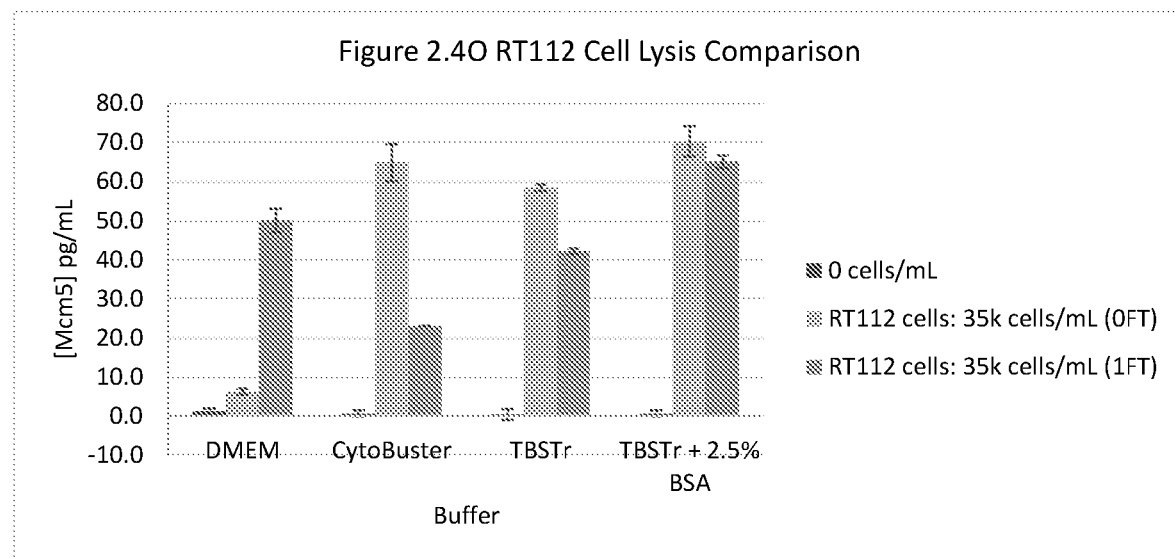

A TBSTr+2.5% BSA composition was compared with TBSTr and CytoBuster. The results are presented in FIGS. 15A, 15B and 15C.

With all cell lines, the TBST+2.5% BSA has proven to be both stable (concentration within 10% of fresh lysate) and to have the highest signal after 1 FT cycle than both Cyto-Buster and TBST. Generally speaking, CytoBuster appears to give very variable results with fresh lysates, but there is always a pronounced loss of potency when freeze-thawing is performed.

Example 15

Figure 16:
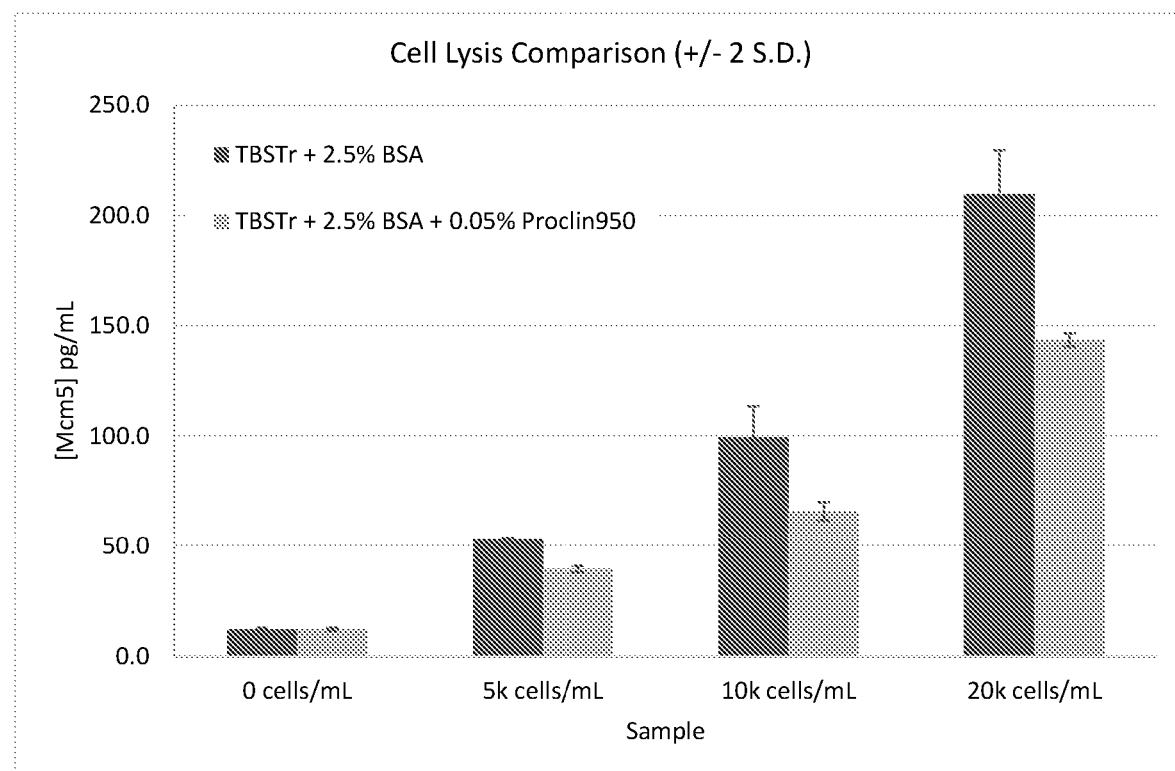
FIG. 16 shows a graph comparing TBST+2.5% BSA buffers with or without ProClin950.
Figure 17:
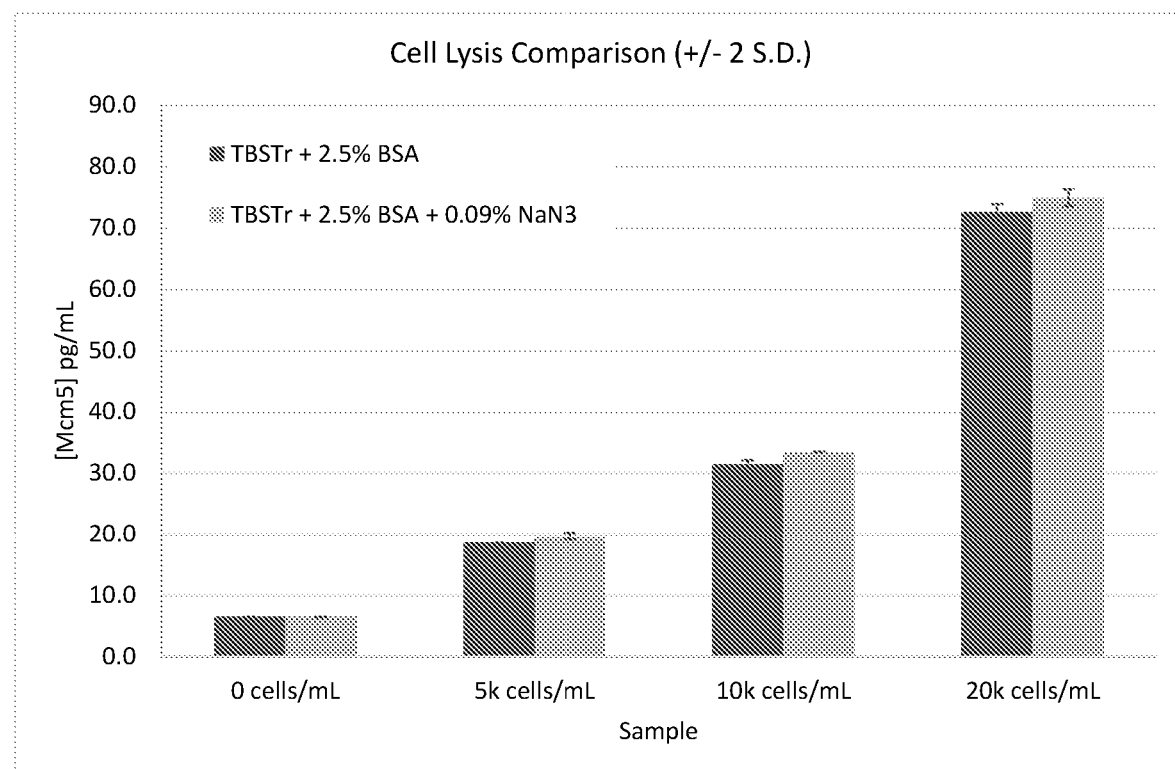
FIG. 17 shows a graph comparing TBST+2.5% BSA buffers with or without Sodium Azide (NaN3).

As BSA containing buffers tend to be prone to microbial growth, the two anti-microbial agents ProClin950 and sodium azide (NaN3) were tested with the TBST+2.5% BSA formulation. The results are presented in FIGS. 16 and 17.

The 0.09% sodium azide is the best candidate for anti-microbial agent as there is less than 10% deviation from the reference buffer.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

Sequence listing

SEQ ID NO: 1
WDETKGE

SEQ ID NO: 2
DDRVAIH

SEQ ID NO: 3
QNLVQSNGNTY

SEQ ID NO: 4
CAGAACCTTGTACAAAGTAATGGAAACACCTATTTA

SEQ ID NO: 5
KVS

SEQ ID NO: 6:
AAGTTTCCAA

SEQ ID NO: 7:
SQSTRVPYT

SEQ ID NO: 8:
TCTCAAAGTACACGTGTTCCGTACACA

SEQ ID NO: 9:
GFSLSTSGMG

SEQ ID NO: 10:
GGGTTTTCACTGAGCACTTCTGGTATGGGT

SEQ ID NO: 11:
IFWDDDK

SEQ ID NO: 12:
ATTTTCTGGGATGATGACAAG

SEQ ID NO: 13:
ARRSDYNYYSMDY

SEQ ID NO: 14:
GCGCGGCGAAGTGACTACAATTACTACTCTATGGACTAC

SEQ ID NO: 15:
QDIGSS

SEQ ID NO: 16:
CAGGACATTGGTAGTAGC

SEQ ID NO: 17:
ATS

SEQ ID NO: 18:
GCCACATCC

SEQ ID NO: 19:
LQYASSPPT

SEQ ID NO: 20:
CTACAATATGCTAGTTCTCCTCCGACG

SEQ ID NO: 21:
GFTFSNYA

SEQ ID NO: 22:
GGATTCACTTTCAGTAACTATGCC

SEQ ID NO: 23:
ISRGGSYT

SEQ ID NO: 24:
ATTAGTCGTGGTGGTAGTTACACC

SEQ ID NO: 25:
ARHGYNYDDGAWFAN

SEQ ID NO: 26:
GCAAGACATGGATATAATTACGACGACGGGGCCTGGTTTGCTAAC

Sequence listing

SEQ ID NO: 27:
DIMLTQSPLSLSVTLGDQASISCRSSQNLVQSNGNTYLTWYLQKPGQSPKVLINKVSNRFYGVPDRFSGSGS
GTDFTLRISRVEAEDLGIYFCSQSTRVPYTFGGGTKLEIRR

SEQ ID NO: 28:
GATATCATGCTGACCCAATCTCCACTCTCCCTGTCTGTCACTCTTGGAGATCAGGCCTCCATCTCTTGCAGA
TCTAGTCAGAACCTTGTACAAAGTAATGGAAACACCTATTTAACTTGGTACCTGCAGAAGCCAGGCCAGTCT
CCAAAGGTCCTGATCAACAAAGTTTCCAACCGATTTTATGGGGTCCCAGACAGGTTCAGTGGCAGTGGATCA
GGGACAGATTTCACACTCAGGATCAGCAGAGTGGAGGCTGAGGATCTGGGAATTTATTTCTGCTCTCAAAGT
ACACGTGTTCCGTACACATTCGGAGGGGGGACCAAGCTGGAAATAAGACG

SEQ ID NO: 29:
QQDLQQSGPGILQPTQTLSLTCSFSGFSLSTSGMGVSWIRQSSNMGLEWLAHIFWDDDKRYNPSLRSRLTLS
KDTSSSQVFLMITSVSTADSATYYCARRSDYNYYSMDYWGQGTAVTVSS

SEQ ID NO: 30:
CAGCAAGATCTGCAGCAGTCTGGCCCTGGGATATTGCAGCCCACCCAGACCCTCAGTCTGACTTGTTCTTTC
TCTGGGTTTTCACTGAGCACTTCTGGTATGGGTGTGAGTTGGATTCGTCAATCTTCAAATATGGGTCTGGAG
TGGCTGGCACACATTTTCTGGGATGATGACAAGCGCTATAATCCCTCCCTGAGGAGCCGACTCACGCTCTCC
AAGGATACCTCCAGTAGCCAGGTATTTCTCATGATCACCAGTGTGAGTACTGCAGATTCTGCCACATACTAC
TGTGCGCGGCGAAGTGACTACAATTACTACTCTATGGACTACTGGGGTCAAGGAACCGCAGTCACCGTCTCC
TCA

SEQ ID NO: 31:
DIMLTQSPSSLSASLGERVSLTCRASQDIGSSLNWLQQEPDGTIKRLIYATSSLDSGVPKRFSGSRSGSDYS
LTISSLESEDFVDYYCLQYASSPPTFGGGTKLEIK

SEQ ID NO: 32:
GATATCATGCTGACCCAATCTCCATCCTCCTTATCTGCCTCTCTGGGAGAAAGAGTCAGTCTCACTTGTCGG
GCAAGTCAGGACATTGGTAGTAGCTTAAACTGGCTTCAACAGGAACCAGATGGAACTATTAAACGCCTAATC
TACGCCACATCCAGTTTAGATTCTGGTGTCCCCAAAAGGTTCAGTGGCAGTAGGTCTGGGTCAGATTATTCT
CTCACCATCAGCAGCCTTGAGTCTGAAGATTTTGTAGACTATTACTGTCTACAATATGCTAGTTCTCCTCCG
ACGTTCGGTGGAGGCACCAAGCTGGAAATCAAAC

SEQ ID NO: 33:
VKLQESGGGLVKPGGSLKLSCAASGFTFSNYAMSWVRQNPEKRLEWVATISRGGSYTYYPDSVKGRFTISRD
NAKNTLYLQMNSLRSEDTAMYFCARHGYNYDDGAWFANWGQGTLVTVSA

SEQ ID NO: 34:
TAGGTGAAACTGCAGGAGTCTGGGGGAGGCTTAGTGAAGCCTGGAGGGTCCCTGAAACTCTCCTGTGCAGCC
TCTGGATTCACTTTCAGTAACTATGCCATGTCTTGGGTTCGCCAGAATCCGGAGAAGAGGCTGGAGTGGGTC
GCAACCATTAGTCGTGGTGGTAGTTACACCTACTATCCAGACAGTGTGAAGGGTCGATTCACCATCTCCAGA
GACAATGCCAAGAACACCCTGTATCTGCAAATGAACAGTCTGAGGTCTGAGGACACGGCCATGTATTTCTGT
GCAAGACATGGATATAATTACGACGACGGGGCCTGGTTTGCTAACTGGGGCCAAGGGACTCTGGTCACTGTC
TCTGCA

SEQ ID NO: 35:
```
        10         20         30         40         50         60
MSGFDDPGIF YSDSFGGDAQ ADEGQARKSQ LQRRFKEFLR QYRVGTDRTG FTFKYRDELK
        70         80         90        100        110        120
RHYNLGEYWI EVEMEDLASF DEDLADYLYK QPAEHLQLLE EAAKEVADEV TRPRPSGEEV
       130        140        150        160        170        180
LQDIQVMLKS DASPSSIRSL KSDMMSHLVK IPGIIIAASA VRAKATRISI QCRSCRNTLT
       190        200        210        220        230        240
NIAMRPGLEG YALPRKCNTD QAGRPKCPLD PYFIMPDKCK CVDFQTLKLQ ELPDAVPHGE
       250        260        270        280        290        300
MPRHMQLYCD RYLCDKVVPG NRVTIMGIYS IKKFGLTTSR GRDRVGVGIR SSYIRVLGIQ
       310        320        330        340        350        360
VDTDGSGRSF AGAVSPQEEE EFRRLAALPN VYEVISKSIA PSIFGGTDMK KAIACLLFGG
       370        380        390        400        410        420
SRKRLPDGLT RRGDINLLML GDPGTAKSQL LKFVEKCSPI GVYTSGKGSS AAGLTASVMR
       430        440        450        460        470        480
DPSSRNFIME GGAMVLADGG VVCIDEFDKM REDDRVAIHE AMEQQTISIA KAGITTTLNS
       490        500        510        520        530        540
RCSVLAAANS VFGRWDETKG EDNIDFMPTI LSRFDMIFIV KDEHNEERDV MLAKHVITLH
       550        560        570        580        590        600
VSALTQTQAV EGEIDLAKLK KFIAYCRVKC GPRLSAEAAE KLKNRYIIMR SGARQHERDS
       610        620        630        640        650        660
DRRSSIPITV RQLEAIVRIA EALSKMKLQP FATEADVEEA LRLFQVSTLD AALSGTLSGV
       670        680        690        700        710        720
EGFTSQEDQE MLSRIEKQLK RRFAIGSQVS EHSIIKDFTK QKYPEHAIHK VLQLMLRRGE
       730
IQHRMQRKVL YRLK
```

-continued

Sequence listing

SEQ ID NO: 36
*Homo sapiens* minichromosome maintenance complex component 5 (MCM5), mRNA
NCBI Reference Sequence: NM_006739.3

```
   1 ggaaaaccag aggcgcagtc atgtcgggat tcgacgatcc tggcattttc tacagcgaca
  61 gcttcggggg cgacgcccag gccgacgagg ggcaggcccg caaatcgcag ctgcagaggc
 121 gcttcaagga gttcctgcgg cggtaccgag tgggcaccga ccgcacgggc ttcaccttca
 181 aatacaggga tgaactcaag cggcattaca acctgggga gtactggatt gaggtggaga
 241 tggaggatct ggccagcttt gatgaggacc tggccgacta cttgtacaag cagccagccg
 301 agcacctgca gctgctggag gaagctgcca aggaggtagc tgatgaggtg acccggcccc
 361 ggccttctgg ggaggaggtg ctccaggaca tccaggtcat gctcaagtcg gacgccagcc
 421 cttccagcat tcgtagcctg aagtcggaca tgatgtcaca cctggtgaag atccctggca
 481 tcatcatcgc ggcctctgcg gtccgtgcca aggccacccg catctctatc cagtgccgca
 541 gctgccgcaa caccctcacc aacattgcca tgcgcccctgg cctcgagggc tatgccctgc
 601 ccaggaagtg caacacagat caggctgggc gccccaaatg cccattggac ccgtacttca
 661 tcatgcccga caaatgcaaa tgcgtggact tccagaccct gaagctgcag gagctgcctg
 721 atgcagtccc ccacggggag atgcccagac acatgccagt ctactgcgca aggtacctgt
 781 gtgacaaggt cgtccctggg aacagggtta ccatcatggg catctactcc atcaagaagt
 841 ttggcctgac taccagcagg ggccgtgaca gggtgggcgt gggcatccga agctcctaca
 901 tccgtgtcct gggcatccag gtggacacag atggctctgg ccgcagcttt gctggggccg
 961 tgagccccca ggaggaggag gagttccgtc gcctggctgc cctcccaaat gtctatgagg
1021 tcatctccaa gagcatcgcc cctccatct tggggcac agacatgaag aaggccattg
1081 cctgcctgct ctttgggggc tcccgaaaga ggctccctga tggacttact cgccgaggag
1141 acatcaacct gctgatgcta ggggaccctg gacagccaa gtcccagctt ctgaagtttg
1201 tggagaagtg ttctcccatt gggtataca cgtctgggaa aggcagcagc gcagctggac
1261 tgacagcctc ggtgatgagg gacccttcgt cccggaattt catcatggag ggcggagcca
1321 tggtcctggc cgatggtggg gtcgtctgta ttgacgagtt tgacaagatg cgagaagatg
1381 accgtgtggc aatccacgaa gccatggagc agcagaccat ctctatcgcc aaggctggga
1441 tcaccaccac cctgaactcc cgctgctccg tcctggctgc tgccaactca gtgttcggcc
1501 gctgggatga cgacaagggg gaggacaaca ttgacttcat gcccaccatc ttgtcgcgct
1561 tcgacatgat cttcatcgtc aaggatgagc acaatgagga gagggatgtg atgctggcca
1621 agcatgtcat cactctgcac gtgagcgcac tgacacagac acaggctgtg gagggcgaga
1681 ttgacctggc caagctgaag aagtttattg cctactgccg agtgaagtgt ggccccggc
1741 tgtcagcaga ggctgcagag aaactgaaga accgctacat catcatgcgg agcgggcgc
1801 gtcagcacga gagggacagt gaccgccgct ccagcatccc catcactgtg cggcagctgg
1861 aggccattgt cgcatcgcg gaagccctca gcaagatgaa gctgcagccc ttcgccacag
1921 aggcagatgt ggaggaggcc ctgcggctct tccaagtgtc cacgttggat gctgccttgt
1981 ccggtaccct gtcaggggtg gagggcttca ccagccagga ggccagcccc atgctgagcc
2041 gcatcgagaa gcagctcaag cgccgctttg ccattggctc ccaggtgtct gagcacagca
2101 tcatcaagga cttcaccaag cagaaatacc cggagcacgc catccacaag gtgctgcagc
2161 tcatgctgcg gcgcggcgag atccagcatc gcatgcagcg caaggttctc taccgcctca
2221 agtgagtcgc gccgcctcac tggactcatg gactcgccca cgcctcgccc ctcctgccgc
2281 tgcctgccat tgacaatgtt gctgggacct ctgcctcccc actgcagccc tcgaacttcc
2341 caggcaccct cctttctgcc ccagaggaag gagctgtagt gtcctgctgc ctctgggcgc
2401 ccgcctctag cgcggttctg ggaagtgtgc ttggcatcc cgttaataat aaagccacgg
2461 tgtgttcagg taaaaaaaaa aaaaaaaaaa aaaaaaaaaa aaaaaaaaaa aaaaaaaaaa
2521 aaaaaaaaaa aaaa
```

The invention claimed is:

1. A method for detecting the presence of Mcm5 (minichromosome maintenance 5) in a subject, the method comprising:
   (a) preparing a sample from said subject wherein preparing the sample comprises exposing the sample to a lysis buffer, wherein the lysis buffer is capable of releasing Mcm5 from cells in the sample and wherein the lysis buffer comprises a detergent which comprises or consists of polyethylene glycol p-(1,1,3.3,-tetramethyl-butyl)-phenyl ether:
   (b) performing an assay to determine the concentration of Mcm5 by exposing the sample to a first monoclonal antibody and a second monoclonal antibody and measuring the amount of Mcm5 that binds to the first monoclonal antibody and the second monoclonal antibody; and
   (c) comparing the concentration of Mcm5 determined in step (b) to reference values;
   wherein the first monoclonal antibody and the second monoclonal antibody bind to Mcm5,
   wherein the first monoclonal antibody binds to a polypeptide comprising an amino acid sequence of SEQ ID NO: 1 and comprises the following Complementary Determining Regions (CDRs):
   (a) 12A7 CDRH1 which has a sequence consisting of SEQ ID NO: 9;
   (b) 12A7 CDRH2 which has a sequence consisting of SEQ ID NO: 11;
   (c) 12A7 CDRH3 which has a sequence consisting of SEQ ID NO: 13;
   (d) 12A7 CDRL1 which has a sequence consisting of SEQ ID NO: 3;
   (e) 12A7 CDRL2 which has a sequence consisting of SEQ ID NO: 5; and
   (f) 12A7 CDRL3 which has a sequence consisting of SEQ ID NO: 7,
   and wherein the second monoclonal antibody binds to a polypeptide comprising an amino acid sequence of SEQ ID NO: 2 and comprises the following Complementary Determining Regions (CDRs):
   (a) 4B4 CDRH1 which has a sequence consisting of SEQ ID NO: 21,
   (b) 4B4 CDRH2 which has a sequence consisting of SEQ ID NO: 23;
   (c) 4B4 CDRH3 which has a sequence consisting of SEQ ID NO: 25;
   (d) 4B4 CDRL1 which has a sequence consisting of SEQ ID NO: 15;
   (e) 4B4 CDRL2 which has a sequence consisting of SEQ ID NO: 17; and
   (f) 4B4 CDRL3 which has a sequence consisting of SEQ ID NO: 19.

2. The method of claim 1 wherein the first monoclonal antibody is an antibody which:
   (i) comprises a heavy chain variable region having a sequence at least 85%, 90%, 95%, 98%, 99% or 100% identical to SEQ ID NO: 29;
   (ii) comprises a light chain variable region sequence having a sequence at least 85%, 90%, 95%, 98%, 99% or 100% identical to SEQ ID NO: 27; or
   (iii) competes with the antibody of (i) or (ii); and/or
   the second monoclonal antibody is an antibody which:
   (i) comprises a heavy chain variable region having a sequence at least 85%, 90%, 95%, 98%, 99% or 100% identical to SEQ ID NO: 33;
   (ii) comprises a light chain variable region sequence having a sequence at least 85%, 90%, 95%, 98%, 99% or 100% identical to SEQ ID NO: 31; or
   (iii) competes with the antibody of (i) or (ii).

3. The method of claim 1 wherein the first monoclonal antibody and/or the second monoclonal antibody is Fab'$_2$ (fragment antigen-binding'$_2$), F'(ab)$_2$, Fv (variable domain), a single chain antibody or a diabody.

4. The method of claim 1 wherein
   (a) the first monoclonal antibody comprises a 12A7 CDRH1 which has a sequence consisting of SEQ ID NO: 9, a 12A7 CDRH2 which has a sequence consisting of SEQ ID NO: 11, and a 12A7 CDRH3 which has a sequence consisting of SEQ ID NO: 13; and/or
   (b) the first monoclonal antibody comprises a 12A7 CDRL1 which has a sequence consisting of SEQ ID NO: 3, a 12A7 CDRL2 which has a sequence consisting of SEQ ID NO: 5 and a 12A7 CDRL3 which has a sequence consisting of SEQ ID NO: 7.

5. The method of claim 1 wherein
   (a) the second monoclonal antibody comprises a 4B4 CDRH1 which has a sequence consisting of SEQ ID NO: 21, a 4B4 CDRH2 which has a sequence consisting of SEQ ID NO: 23, and a 4B4 CDRH3 which has a sequence consisting of SEQ ID NO: 25; and/or
   (b) the second monoclonal antibody has a 4B4 CDRL1 which has a sequence consisting of SEQ ID NO: 15, a 4B4 CDRL2 which has a sequence consisting of SEQ ID NO: 17 and a 4B4 CDRL3 which has a sequence consisting of SEQ ID NO: 19.

6. The method of claim 1 wherein
   (a) the first monoclonal antibody comprises a heavy chain variable region having a sequence at least 95% identical to SEQ ID NO: 29;
   (b) the first monoclonal antibody comprises a heavy chain variable region having a sequence at least 98% identical to SEQ ID NO: 29;
   (c) the first monoclonal antibody comprises a light chain variable region having a sequence at least 95% identical to SEQ ID NO: 27;
   (d) the first monoclonal antibody comprises a light chain variable region having a sequence at least 98% identical to SEQ ID NO: 27;
   (e) the second monoclonal antibody comprises a heavy chain variable region having a sequence at least 95% identical to SEQ ID NO: 33;
   (f) the second monoclonal antibody comprises a heavy chain variable region having a sequence at least 98% identical to SEQ ID NO: 33;
   (g) the second monoclonal antibody comprises a light chain variable region having a sequence at least 95% identical to SEQ ID NO: 31; and/or (h) the second monoclonal antibody comprises a light chain variable region having a sequence at least 98% identical to SEQ ID NO: 31.

7. The method of claim 1 wherein
(a) an abnormal value for the concentration of Mcm5 indicates an increased likelihood of a urological cancer in said subject;
(b) the assay to determine the concentration of Mcm5 is an ELISA assay (enzyme-linked immunosorbent assay);
(c) the assay to determine the concentration of Mcm5 wherein the ELISA assay is a sandwich ELISA assay;
(d) the assay to determine the concentration of Mcm5 comprises capturing the Mcm5 in the sample using a capture antibody and detecting the concentration of the Mcm5 using a detection antibody, wherein the capture antibody is the first monoclonal antibody and the detection antibody is the second monoclonal antibody or the capture antibody is the second monoclonal antibody and the detection antibody is the first monoclonal antibody;
(e) the assay to determine the concentration of Mcm5 comprises capturing the Mcm5 in the sample using a capture antibody and the capture antibody is immobilised on an ELISA plate; and/or
(f) the assay to determine the concentration of Mcm5 comprises detecting the concentration of the Mcm5 using a detection antibody and the detection antibody is conjugated to Horse Radish Peroxidase.

8. The method of claim 1 wherein
(a) the first monoclonal antibody is a capture antibody and the second antibody is a detection antibody; or
(b) the second monoclonal antibody is a capture antibody and the first antibody is a detection antibody.

9. The method of claim 8 wherein
(a) the capture antibody is bound to an ELISA plate; and/or
(b) the detection antibody is conjugated to horseradish peroxidase.

10. The method of claim 8 wherein
(a) the lysis buffer comprises a detergent and the detergent comprises or consists of polyethylene glycol p-(1,1,3,3-tetramethylbutyl)-phenyl ether at a concentration between 0.01% and 25%, between 0.01% and 10%, between 0.05% and 5%, between 0.05% and 1%, between 0.05% and 0.5% or around 0.1%;
(b) the lysis buffer comprises a detergent and the detergent comprises sodium deoxycholate or sodium dodecylsulphate; and/or
(c) the lysis buffer comprises a detergent and the detergent comprises sodium deoxycholate or sodium dodecylsulphate at a concentration between 0.1% and 20%, between 0.5% and 10%, between 0.5% and 5% or around 1%.

11. The method of claim 1 wherein the method does not comprise centrifuging the sample at 15,000 g for 10 minutes.

12. The method of claim 1 wherein
(a) the sample comprises urine;
(b) the sample or the urine sample comprises urinary sediment; and/or
(c) the sample or urine sample comprises urinary sediment obtained from first catch urine collected after prostatic massage.

13. The method of claim 1 wherein an abnormal value for the concentration of Mcm5 indicates an increased likelihood of a urological cancer in said subject and said urological cancer comprises transitional cell carcinoma; wherein said transitional cell carcinoma comprises:
(i) bladder cancer;
(ii) prostate cancer; or
(iii) cancer of the pelvis or the kidney.

14. The method of claim 1 wherein preparing the sample comprises a step of exposing the sample to a lysis buffer and:
(i) the lysis buffer is not PBS (phosphate-buffered saline) containing 0.4% sodium deoxycholate and 0.02% sodium azide;
(ii) the method does not comprise incubation of the sample at a temperature greater than 95° C. for around 45 minutes;
(iii) the method does not comprise shearing the nucleic acids by passing the sample through a 21 gauge needle;
(iv) the method does not comprise digesting the nucleic acids by exposing the sample to Dnase I or Rnase A; and/or
(v) the method does not comprise centrifuging the sample at 15,000 g for) minutes.

15. The method of claim 1 wherein
(a) preparing the sample comprises a step of concentrating cells in the urine sample; and/or
(b) the sample comprises cells and preparing the sample consists of the following steps:
(i) centrifugation of the sample; and
(ii) resuspension of the pelleted cells from the sample in the lysis buffer.

16. The method of claim 8 wherein
(a) the lysis buffer comprises a buffer component;
(b) the lysis buffer comprises a buffer component and the buffer component is, comprises or consists of 1,3-Propanediol, 2-amino-2-(hydroxymethyl)-, hydrochloride or tris(hydroxymethyl)methylamine (Tris) buffer;
(c) the lysis buffer comprises a buffer component and the buffer component comprises or consists of Tris buffer at a concentration greater than 5 mM, between 5 mM and 350 mM between 200 mM and 300 mM, between 10 mM and 25 mM, around 10 mM or around 250 mM; and/or
(d) the lysis buffer comprises a buffer component and the buffer component maintains the pH of the buffer between pH 4 and pH 9, between pH 5 and pH 8, between pH 6 and pH 8 or around pH 7.6.

17. The method of claim 8 wherein
(a) the lysis buffer comprises sodium chloride at a concentration between 20 mM and 300 mM, between 150 mM and 300 mM, between 100 mM, and 200 mM or around 200 mM; and/or;
(b) the lysis buffer has an ionic strength of between 1 mM and 500 mM, between 50 mM and 450 mM, between 100 mM and 250 mM, or between 100 mM and 175 mM.

18. The method of claim 1 wherein;
(a) the method does not comprise incubation of the sample at a high temperature; or
(b) the method does not comprise incubation of the sample at a temperature greater than 50° C., greater than 60° C., greater than 70° C., greater than 80° C., greater than 90° C., between 50° C. and 120° C., between 60° C. and 110° C., between 70° C. and 100° C. or between 80° C. and 100° C.

19. The method of claim 1 wherein the method does not comprise incubation of the sample at a high temperature for more than 30 minutes, more than 35 minutes, more than 40 minutes, more than 45 minutes, between 30 minutes and 2 hours, between 35 minutes and 2 hours, or between 40 minutes and 2 hours.

20. The method of claim 1 wherein the method does not comprise shearing nucleic acids in the sample by mechanical shearing.

21. The method of claim 1 wherein the method does not comprise exposing the sample to enzymes which digest nucleic acids.

* * * * *